US006586452B1

(12) United States Patent
Shih et al.

(10) Patent No.: US 6,586,452 B1
(45) Date of Patent: Jul. 1, 2003

(54) C₁ TO C₄ SIDE CHAIN MODIFIED NODULISPORIC ACID ANALOGS

(75) Inventors: Thomas Shih, Jackson, NJ (US); Steven L. Colletti, Princeton Junction, NJ (US); Michael H. Fisher, Ringoes, NJ (US); Peter T. Meinke, Plainfield, NJ (US); Howard C. H. Kuo, South Plainfield, NJ (US); Prasun K. Chakravarty, Edison, NJ (US); Matthew J. Wyvratt, Mountainside, NJ (US); Sriram Tyagarajan, Edison, NJ (US); Richard Berger, Cranford, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/901,266

(22) Filed: Jul. 9, 2001

Related U.S. Application Data

(60) Provisional application No. 60/218,398, filed on Jul. 14, 2000.

(51) Int. Cl.⁷ .................... C07D 487/16; C07D 519/00; A61K 31/407; A61P 33/10; A61P 33/14
(52) U.S. Cl. ........................... 514/358; 544/92; 544/96; 544/142; 544/281; 544/350; 546/84; 546/121; 546/174; 546/198; 546/276.7; 548/154; 548/181; 548/216; 548/218; 548/221; 548/231; 548/236; 548/238; 548/247; 548/324.1; 514/374; 514/375; 514/376; 514/365; 514/368; 514/378; 514/392; 514/410

(58) Field of Search ................. 548/417, 218, 548/154, 238, 236, 181, 247, 216, 221, 231, 324.1; 544/281, 350, 142, 92, 96; 546/121, 84, 276.7, 174, 198; 514/375, 410, 300, 258, 292, 229.5, 249, 368, 374, 228.8, 376, 365, 233.2, 343, 392, 314, 378, 321, 358

(56) References Cited

U.S. PATENT DOCUMENTS

| 5,399,582 | A |   | 3/1995  | Dombrowski et al.     |
|-----------|---|---|---------|-----------------------|
| 5,595,991 | A | * | 1/1997  | Shoop et al. ............ 514/233.2 |
| 5,962,499 | A |   | 10/1999 | Meinke et al.         |
| 6,221,894 | B1|   | 4/2001  | Meinke et al.         |
| 2002/0045653 | A1 | * | 4/2002 | Shih et al. ................... 514/410 |

OTHER PUBLICATIONS

CAS Registry printout for RN 183287–42–5.*

* cited by examiner

Primary Examiner—Mark Berch
(74) Attorney, Agent, or Firm—Mollie M. Yang; David L. Rose

(57) ABSTRACT

The present invention relates to novel nodulosporic acid derivatives, which are acaricidal, antiparasitic, insecticidal and anthelmintic agents.

10 Claims, No Drawings

$C_1$ TO $C_4$ SIDE CHAIN MODIFIED NODULISPORIC ACID ANALOGS

CROSS REFERENCE TO RELATED APPLICATIONS

This application is based on, and claims priority from, U.S. Provisional Application Ser. No. 60/218,398 filed on Jul. 14, 2000, which is hereby incorporated by reference in its entirety.

BACKGROUND OF THE INVENTION

Nodulosporic acid and related component nodulisporic acid A1 are antiparasitic agents and ectoparasiticidal agents isolated from the fermentation culture of Nodulisporiuim sp. MF-5954 (ATCC 74245). These three compounds have the following structures as disclosed in U.S. Pat. No. 5,399,582 and J. G. Ondeyka et al. *J. Am. Chem. Soc.* 1997, 119(38), 8809–8816.

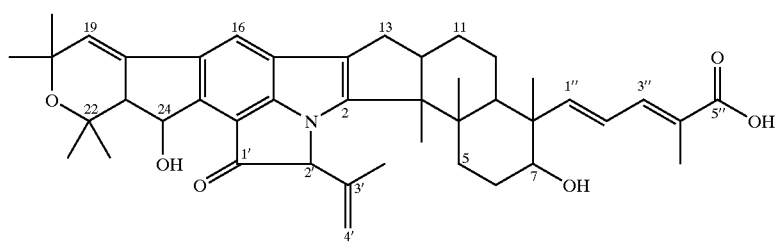

nodulisporic acid A (compound A)

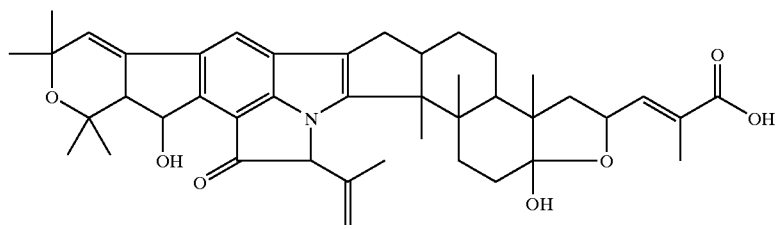

nodulisporic acid A1 (compound B)

Derivatives of nodulisporic acid are disclosed in U.S. Pat. No. 5,962,499.

SUMMARY OF THE INVENTION

This invention relates to new acaricidal, antiparasitic, insecticidal and anthelmintic agents related to the nodulisporic acids, to processes for their preparation, compositions thereof, their use in the treatment of parasitic infections, including helminthiasis, in human and animals, and their use in the treatment of parasitic infections in plants or plant products.

DETAILED DESCRIPTION OF THE INVENTION

The present invention provides compounds having the formula I:

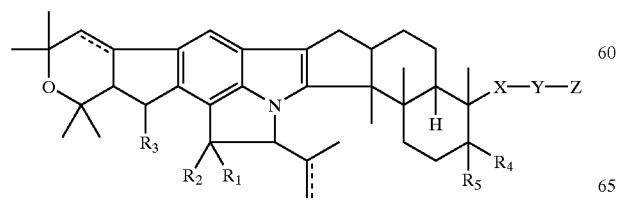

I wherein ══ represents a single or a double bond;

X is (1) a bond, or
  (2) $C(R^x)(R^y)$;

Y is (1) a bond, or
  (2) $C(R^x)(R^y)$;

Z is (1) H,
  (2) $C(R^x)(R^y)(R^z)$,
  (3) a group selected from $R^z$; or

X—Y is (1) $C(R^x)$═$C(R^x)$ or
  (2) C≡C, or

Y—Z is (1) $C(R^x)$═$C(R^x)(R^z)$ or
  (2) C≡$C(R^z)$;

$R_1$ is (1) hydrogen,
  (2) optionally substituted $C_1$–$C_{10}$ alkyl,
  (3) optionally substituted $C_2$–$C_{10}$ alkenyl,
  (4) optionally substituted $C_2$–$C_{10}$ alkynyl,
  (5) optionally substituted $C_3$–$C_8$ cycloalkyl,
  (6) optionally substituted $C_5$–$C_8$ cycloalkenyl,
  (7) optionally substituted aryl,
  (8) optionally substituted 5- or 6-membered heterocycle containing from 1 to 4 heteroatoms independently selected from O, S and $NR^c$, where the substitutents on the alkyl, alkenyl, alkynyl are 1 to 3 groups selected from R', the substituents on aryl is 1 to 3 groups selected from R", and the substituents on cycloalkyl and cycloalkenyl are 1 to 3 groups independently selected from R", oxo and thiono;

$R_2$, $R_3$, and $R_4$ are independently $OR^a$, $OCO_2R^b$, $OC(O)NR^cR^d$; or $R_1+R_2$ represent ═O, ═$NOR^a$, ═N—$NR^cR^d$, ═$CR^aCO_2R^a$, ═$CR^aC(O)NR^cR^d$, ═$CR^aCN$, ═$CR^aC(O)R^a$, or ═$CR^aR^a$;

$R_5$ is (1) hydrogen,
  (2) $OR^a$ or $R_4+R_5$ represent ═O, ═$NOR^a$, ═N—$NR^cR^d$ or ═$CR^aR^a$;

$R^a$ is (1) H,
  (2) optionally substituted $C_1$–$C_{10}$ alkyl,
  (3) optionally substituted $C_3$–$C_{10}$ alkenyl,
  (4) optionally substituted $C_3$–$C_{10}$ alkynyl,
  (5) optionally substituted $C_3$–$C_{15}$ cycloalkyl,
  (6) optionally substituted $C_5$–$C_{10}$ cycloalkenyl,
  (7) optionally substituted aryl, (8) optionally substituted heteroaryl,
(9) optionally substituted 3- to 10-membered heterocycle containing 1 to 4 heteroatoms selected from O, S and $NR^g$,
(10) a benzene ring fused to a 4- to 8-membered heterocyclic ring with from 1 to 4 heteroatoms selected from oxygen, sulfur and $NR^g$,
(11) a 4- or 8-membered heterocyclic ring with from 1 to 4 heteroatoms selected from O, S and $NR^g$ fused to a 4- or 8-membered heterocyclic ring with from 1 to 4 heteroatoms selected from O, S and $NR^g$, and where the substituents on the aryl, alkyl, alkenyl, alkynyl groups are 1 to 10 groups selected from R'; the substituents on aryl, heteroaryl and benzene are 1 to 5 groups selected from R"; and the substituents on cycloalkyl, cycloalkenyl and heterocycle are 1 to 10 groups selected from R", oxo and thiono;

$R^b$ is (1) a group selected from $R^a$,
(2) optionally substituted $C_2-C_6$ alkanoyl, $R^c$ and $R^d$ are independently selected from $R^b$, hydroxy, $C_1-C_5$alkoxy, $C_1-C_5$alkoxycarbonyl, aminocarbonyl, $C_1-C_5$alkylaminocarbonyl and $C_1-C_5$dialkylaminocarbonyl; or $R^c$ and $R^d$ together with the N to which they are attached form a 3- to 10-membered ring containing 0 to 2 additional heteroatoms selected from O, $S(O)_m$, and $NR^g$, said ring is optionally substituted with 1 to 5 groups independently selected from R", thiono and oxo; said ring is further optionally fused to a benzene ring optionally substituted with 1 to 3 groups selected from $R^e$; said ring is further optionally spirofused to a $C_3-C_7$cycloalkyl ring:

$R^e$ is (1) halogen,
(2) $C_1-C_7$ alkyl,
(3) $C_1-C_3$ perfluoroalkyl,
(4) $S(O)_mR^i$,
(5) cyano,
(6) nitro,
(7) $R^iO(CH_2)_v-$,
(8) $R^iCO_2(CH_2)_v-$,
(9) $R^iOCO(CH_2)_v$,
(10) optionally substituted aryl where the substituents are from 1 to 3 of halogen, $C_1-C_6$ alkyl, $C_1-C_6$ alkoxy, or hydroxy,
(11) $SO_2NR^iR^i$, or
(12) amino;

$R^f$ is (1) H,
(2) $C_1-C_5$alkyl optionally substituted with 1 to 5 groups selected from halogen, cyano, hydroxy, $C_1-C_3$alkoxy, $NR^gR^h$, $CO_2R^i$ and $CONR^gR^h$,
(3) $C_{2-6}$alkenyl,
(4) $C_{2-6}$alkynyl,
(5) $C_3-C_6$cycloalkyl,
(6) aryl optionally substituted with 1 to 4 groups independently selected from $R^e$, or 2 adjacent substituents together form methylenedioxy, or
(7) aryl-$C_1-C_3$alkyl optionally substituted with 1 to 4 groups independently selected from $R^e$, or 2 adjacent substituents together form methylenedioxy, or two Rf groups together with the nitrogen atom to which they are attached form a a 3-to 10-membered ring containing 0 to 2 additional heteroatoms selected from O, $S(O)_m$, and $NR^g$, said ring is optionally substituted with 1 to 5 groups independently selected from R", thiono and oxo; said ring is further optionally fused to a benzene ring optionally substituted with 1 to 3 groups selected from $R^e$; said ring is further optionally spirofused to a $C_3-C_7$cycloalkyl ring;

$R^g$ and $R^h$ are independently
(1) hydrogen,
(2) $C_1-C_{10}$ alkyl optionally substituted with 1 to 10 groups selected from hydroxy, amino, $C(O)R^i$, and $CO_2R^i$,
(3) aryl optionally substituted with 1 to 5 groups selected from halogen, amino, 1,2-methylenedioxy, $C_1-C_7$ alkoxy, $C_1-C_7$ alkyl and $C_1-C_3$ perfluoroalkyl,
(4) aryl $C_1-C_6$ alkyl, wherein the aryl is optionally substituted with 1 to 5 groups selected from halogen, amino, 1,2-methylenedioxy, $C_1-C_7$ alkoxy, $C_1-C_7$ alkyl and $C_1-C_3$ perfluoroalkyl,
(5) $C_3-C_7$cycloalkyl optionally substituted with phenyl,
(6) $C_1-C_5$ alkanoyl,
(7) $C_1-C_5$ alkoxycarbonyl,
(8) aryl $C_1-C_5$ alkoxycarbonyl,
(9) aminocarbonyl,
(10) $C_1-C_5$ monoalkylaminocarbonyl
(11) $C_1-C_5$ dialkylaminocarbonyl; or $R^g$ and $R^h$ together with the N to which they are attached form a 3- to 7-membered ring containing 0 to 2 additional heteroatoms selected from O, $S(O)_m$, and $NR^i$, optionally substituted with 1 to 3 groups independently selected from $R^e$ and oxo;

$R^i$ is (1) hydrogen,
(2) $C_1-C_3$ perfluoroalkyl,
(3) $C_1-C_6$ alkyl,
(4) optionally substituted aryl $C_0-C_6$ alkyl, where the aryl substituents are from 1 to 3 groups independently selected from halogen, $C_1-C_6$ alkyl, $C_1-C_6$ alkoxy, and hydroxy;

$R^x$ and $R^y$ are independently selected from the group consisting of
(1) hydrogen
(2) optionally substituted $C_1-C_{10}$ alkyl,
(3) optionally substituted $C_2-C_{10}$ alkenyl,
(4) optionally substituted $C_2-C_{10}$ alkynyl, wherein the substituents on alkyl, alkenyl and alkynyl are 1 to 5 groups independently selected from R',
(5) a group selected from $R^z$, or $R^x+R^y$ is (1) $=NOR^a$,
(2) $=NNR^cR^d$,
(3) $=NNR^cSO_2R^a$,
(4) $=CR^aCO_2R^a$, or
(5) $=O$, $R^z$ is (1) optionally substituted aryl,
(2) optionally substituted heterocyclyl,
(3) optionally substituted $C_3-C_8$ cycloalkyl,
(4) optionally substituted $C_5-C_8$cycloalkenyl,
(5) $(CHR^a)_nOR^a$,
(6) $(CHR^a)_nOC(O)R^a$,
(7) $(CHR^a)_nOC(O)OR^b$,
(8) $(CHR^a)_nOC(O)NR^cR^d$,
(9) $(CHR^a)_nOSO2R^a$,
(10) $(CHR^a)_nS(O)mR^a$,
(11) $(CHR^a)_nSC(O)R^a$,
(12) $(CHR^a)_nNR^cR^d$,
(13) $(CHR^a)_nNR^cC(O)R^a$,
(14) $(CHR^a)_nNR^cC(O)OR^a$,
(15) $(CHR^a)_nNR^cC(O)C(O)OR^a$,
(16) $(CHR^a)_nNR^cC(O)NR^cR^d$,
(17) $(CHR^a)_nNR^cSO2R^a$,

(18) $(CHR^a)_nNR^cC(O)P(O)R^a$,
(19) $(CHR^a)_nNR^cC(O)SR^a$,
(20) $C(O)R^a$,
(21) $C(O)OR^b$,
(22) $C(O)NR^cR^d$,
(23) $C(O)N(OR^a)R^c$,
(24) $C(O)NR^cNR^cR^d$,
(25) $C(O)NR^cSO2R^a$,
(26) halogen,
(27) CN,
(28) $N_3$,
(29) perfluoroalkyl,
(30) N=C=O,
(31) $P(O)(OR^a)_2$, wherein the substituents on alkyl, alkenyl and alkynyl are 1 to 5 groups independently selected from R'; the substituents on aryl are 1 to 3 groups independently selected from R"; and the substituents on cycloalkyl and heterocyclyl are 1 to 5 groups independently selected from R", oxo and thiono;

R' is (1) halogen,
(2) cyano,
(3) nitro,
(4) $C(O)R^f$,
(5) $CO_2R^f$,
(6) $C(O)NR^gR^h$,
(7) $OR^f$,
(8) $OC(O)R^f$,
(9) $OC(O)NR^gR^h$,
(10) $OC(O)OR^f$,
(11) $SR^f$,
(12) $S(O)m\ R^f$,
(13) $SO_2NR^gR^h$,
(14) $NR^gR^h$,
(15) $NR^gC(O)R^f$,
(16) $NR^gCO_2R^f$,
(17) $NR^gC(S)OR^f$,
(18) $NR^gC(O)NR^gR^h$,
(19) $C_3$–$C_7$ cycloalkyl optionally substituted with 1 to 4 groups independently selected from $R^e$,
(20) $C_5$–$C_7$ cycloalkenyl optionally substituted with 1 to 4 groups independently selected from $R^e$,
(21) aryl optionally substituted with 1 to 4 groups independently selected from $R^e$, or 2 adjacent substituents together form methylenedioxy,
(22) heteroaryl optionally substituted with 1 to 4 groups independently selected from $R^e$,
(23) 5 to 9-membered heterocycle containing from 1 to 4 heteroatoms independently selected from O, S and $NR^g$, and optionally substituted with 1 to 4 groups independently selected from $R^e$, R" is (1) a group selected from R',
(2) $C_1$–$C_6$ alkyl, optionally substituted with halogen, aryl, $OR^f$ and $NR^gR^h$,
(3) $C_{2-6}$alkenyl,
(4) $C_{2-6}$alkynyl;

m is 0 to 2;
n is 0 or 1; and
v is 0 to 3; or a pharmaceutically acceptable salt thereof; and with the proviso that when X—Y is CH=CH or $CH_2$—$CH_2$, then Z is not C(O)H.

In one subset of the present invention are compounds of formula Ia:

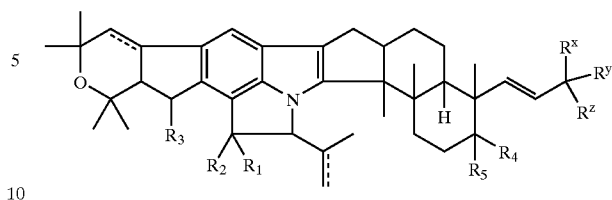

wherein Rx, Ry and Rz are as defined under formula I. In one embodiment, Rx is H, Ry is selected from H, CONRcRd, optionally subsituted aryl and optionally substituted C1–C6alkyl, and Rz is selected from the group consisting of $(CHR^a)_nOR^a$, $(CHR^a)_nOC(O)R^a$, $(CHR^a)_nOC(O)OR^b$, $(CHR^a)_nOC(O)NR^cR^d$, $(CHR^a)_nOSO2R^a$, $(CHR^a)_n\ S(O)mR^a$, $(CHR^a)_nSC(O)R^a$, $(CHR^a)_nNR^cR^d$, $(CHR^a)_nNR^cC(O)R^a$, $(CHR^a)_nNR^cC(O)OR^a$, $(CHR^a)_nNR^cC(O)C(O)OR^a$, $(CHR^a)_nNR^cC(O)NR^cR^d$, $(CHR^a)_nNR^cSO2R^a$, $(CHR^a)_nNR^cC(O)P(O)R^a$, $(CHR^a)_nNR^cC(O)SR^a$, $C(O)R^a$, $C(O)OR^b$, $C(O)NR^cR^d$, $C(O)N(OR^a)R^c$, $C(O)NR^cNR^cR^d$, $C(O)NR^cSO2R^a$ wherein Ra, Rb, Rc, Rd and n are as defined under formula I. In another embodiment, Rx+Ry is oxo, and Rz is selected from $C(O)R^a$, $C(O)OR^b$, $C(O)NR^cR^d$, $C(O)N(OR^a)R^c$, $C(O)NR^cNR^cR^d$, $C(O)NR^cSO2R^a$ wherein Ra, Rb, Rc and Rd are as defined under formula I.

Within formula Ia, there is a subset of compounds having the formula Ia(1):

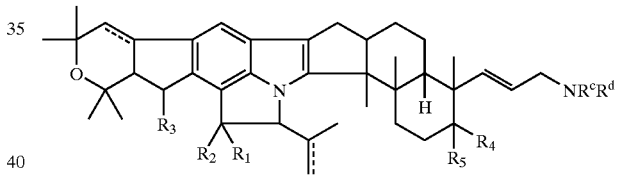

wherein Rc and Rd are as defined under formula I. In one embodiment Rc and Rd are independently H, C1–C6 alkyl or C3–C6alkenyl. In another embodiment Rc and Rd together complete a 5- or 6-membered ring containing one other heteroatom selected from O, S and $NR^g$, and substituted by one or two oxo or thioxo groups, wherein said ring is optionally substituted by 1 to 3 groups selected from aryl and $C_1$–$C_6$alkyl, and is optionally benzofused or spirofused to a $C_3$–$C_7$cycloalkane, wherein said benzo and cycloalkane are optionally substituted with $C_1$–$C_3$alkylalkyl or aryl. More preferably the ring is represented as follows:

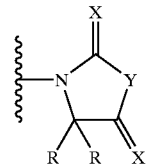

wherein X is O or S, Y is O, S or $NR^g$, $R^g$ is as defined under formula I, and the two R groups are independently H or $C_1$–$C_5$alkyl, or together complete a $C_3$–$C_6$ ring.

Anothere subset within formula Ia are compounds having the formula Ia(2):

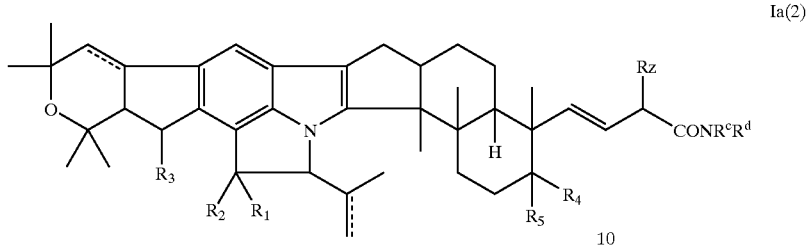

Ia(2)

wherein Rz is OR$^a$, OC(O)R$^a$, OC(O)OR$^b$, OC(O)NR$^c$R$^d$, NR$^c$C(O)R$^a$, NR$^c$C(O)OR$^a$, NR$^c$C(O)NR$^c$R$^d$, NR$^c$SO2R$^a$.

In another subset of formula I are compounds of formula Ib:

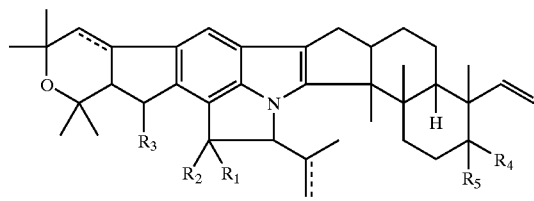

Ib wherein R$^z$ is as defined under formula I. In one embodiment R$^z$ is selected from optionally substituted heterocycle, optionally substituted aryl, CO$_2$R$^b$, CONR$^c$R$^d$, NR$^c$C(O)R$^a$, NR$^c$C(O)OR$^a$, NR$^c$C(O)NR$^c$R$^d$. In another embodiment R$^z$ is selected from optionally substituted oxazolinyl, thiazolinyl, thiazoly and oxazolyl.

One subset of formula Ib are compounds of formula Ib(1)

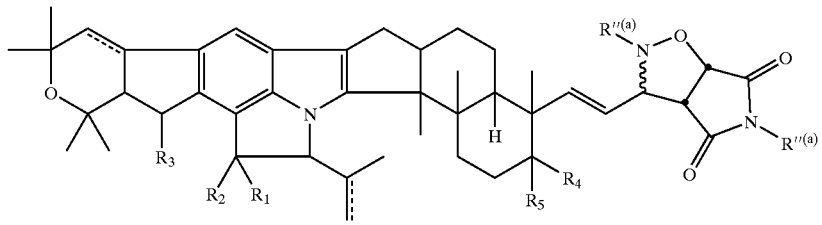

Ib(1)

wherein R"(a) is selected from H, C$_1$–C$_6$alkyl optionally substituted with halogen, aryl, OR$^f$, or NR$^g$R$^h$, C$_3$–C$_7$cycloalkyl optionally substituted with 1 or 2 groups independently selected from R$^e$, and aryl optionally substituted with 1 or 2 groups independently selected from R$^e$.

Another subset of formula Ib are compounds of formula Ib(2)

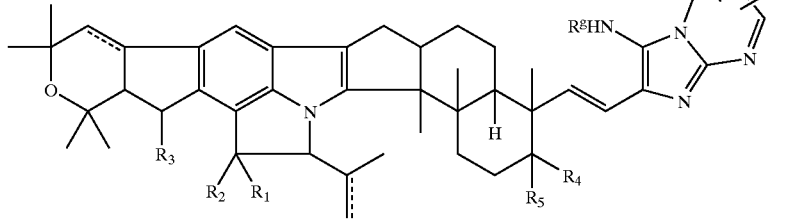

Ib(2)

wherein R$^g$ is as defined under formula I, and the two R"(b) groups are independently H or R" as defined under formula I.

In a preferred embodiment compounds of formula I have the following stereoconfiguration and substituent:

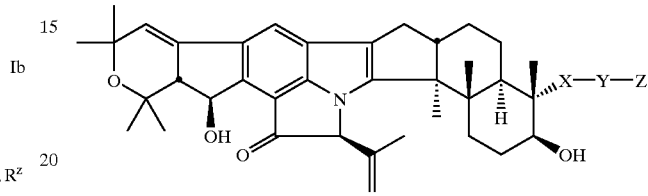

wherein X, Y and Z are as defined under formula I.

The present invention provides in another aspect pharmaceutical compositions comprising a compound of Formula I and a pharmaceutically acceptable carrier. Such compositions may further comprise one or more other active ingredients such as anthelmintic agents, insect regulators, ecdosyne agonists and fipronil.

The present invention provides in another aspect a method for treating parasitic diseases in a mammal which comprises administering an antiparasitic amount of a compound of Formula I. The treatment may further comprise co-administering one or more other active ingredients such as anthelmintic agents, insect regulators, ecdosyne agonists and fipronil.

"Alkyl" as well as other groups having the prefix "alk", such as alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as benzofused carbocycles. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "halogen" is intended to include the halogen atoms fluorine, chlorine, bromine and iodine.

The term "heterocycle", unless otherwise specfied, means mono- or bicyclic compounds that are saturated or partly unsaturated, as well as benzo- or heteroaromatic ring fused saturated heterocycles or partly unsaturated heterocycles, and containing from 1 to 4 heteroatoms independently selected from oxygen, sulfur and nitrogen. Examples of saturated heterocycles include morpholine, thiomorpholine, piperidine, piperazine, tetrahydropyran, tetrahydrofuran, dioxane, tetrahydrothiophene, oxazolidine, pyrrolidine; examples of partly unsaturated heterocycles include dihydropyran, dihydropyridazine, dihydrofuran, dihydrooxazole, dihydropyrazole, dihydropyridine, dihydropyridazine and the like. Examples of benzo- or heteroaromatic ring fused heterocycle include 2,3-dihydrobenzofuranyl, benzopyranyl, tetrahydroquinoline, tetrahydroisoquinoline, benzomorpholinyl, 1,4-benzodioxanyl, 2,3-dihydrofuro(2,3-b)pyridyl and the like.

The term "aryl" is intended to include mono-, bi- and tricyclic aromatic and heteroaromatic rings containing from 0 to 5 heteroatoms independently selected from nitrogen, oxygen and sulfur. The term "aryl" is also meant to include benzofused cycloalkyl, benzofused cycloalkenyl, and benzofused heterocyclic groups. Examples of "aryl" groups include phenyl, pyrrolyl, isoxazolyl, pyrazinyl, pyridinyl, oxazolyl, thiazolyl, imidazolyl, triazolyl, tetrazolyl, furanyl, triazinyl, thienyl, pyrimidinyl, pyridazinyl, pyrazinyl, naphthyl, benzoxazolyl, benzothiazolyl, benzimidazolyl, benzofuranyl, furo(2,3-B)pyridyl, 2,3-dihydrofuro(2,3-b) pyridyl, benzoxazinyl, benzothiophenyl, quinolinyl, indolyl, 2,3-dihydrobenzofuranyl, benzopyranyl, 1,4-benzodioxanyl, indanyl, indenyl, fluorenyl, 1,2,3,4-tetrahydronaphthalene and the like.

Examples of $NR^cR^d$ or $NR^gR^h$ forming a 3- to 10-membered ring containing 0 to 2 additional heteroatoms selected from O, $S(O)_m$ and N are aziridine, azetidine, pyrrolidine, piperidine, thiomorpholine, morpholine, piperazine, octahydroindole, tetrahydroisoquinoline and the like.

The term "optionally substituted" is intended to include both substituted and unsubstituted; thus, for example, optionally substituted aryl could represent a pentafluorophenyl or a phenyl ring.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Certain of the above defined terms may occur more than once in the above formula and upon such occurrence each term shall be defined independently of the other, thus, for example, $OR^a$ at C7 may represent OH and at C24 represent O-acyl.

Compounds described herein contain one or more asymmetric centers and may thus give rise to diastereomers and optical isomers. The present invention is intended to include all possible diastereomers as well as their racemic and resolved, enantiomerically pure forms and all possible geometric isomers. In addition, the present invention includes all pharmaceutically acceptable salts thereof. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Compounds of the present invention are named based on the trivial name of the parent compound, nodulisporic acid (compound A), and their position numbers are those as indicated for nodulisporic acid A.

Compounds of the present invention are prepared from nodulisporic acids A and A1 (Compounds A and B), which in turn are obtained from the fermentation culture of Nodulisporium sp. MF-5954 (ATCC 74245). The description of the producing microorganism, the fermentation process, and the isolation and purification of the three nodulisporic acids are disclosed in U.S. Pat. 5,399,582, issued Mar. 21, 1995, which is hereby incorporated by reference in its entirety.

The above structural formula is shown without a definitive stereochemistry at certain positions. However, during the course of the synthetic procedures used to prepare such compounds, or using racemization or epimerization procedures known to those skilled in the art, the products of such procedures can be a mixture of stereolsomers. In particular, the stereoisomers at C7, C24, C1', $C_2'$, C1", $C_2''$, $C_3''$, $C_4''$ and $C_5''$ may be oriented in either the alpha- or beta-position, representing such groups oriented below or above the plane of the molecule, respectively. In each such case, and at other positions in the molecule, both the alpha- and beta-configurations are intended to be included within the ambit of this invention.

Compounds of formula I wherein the allyl group at position 2' is in the epi configuration may be obtained by treatment of the appropriate precursor with a bases such as hydroxide, methoxide, imidazole, triethylamine, potassium hydride, lithium diisopropylamide and the like in protic or aprotic solvents (as appropriate) such as water, methanol, ethanol, methylene chloride, chloroform, tetrahydrofuran, dimethylformamide and the like. The reaction is complete at temperatures from −78° C. to the reflux temperature of the solution in from 15 minutes to 12 hours.

During certain reactions described below, it may be necessary to protect the groups at C24 and C7. With these positions protected, the reactions may be carried out at other positions without affecting the remainder of the molecule. Subsequent to any of the described reactions (vida infra), the protecting group(s) may be removed and the unprotected product isolated. The protecting groups employed at C24 and C7 are those which may be readily synthesized, not significantly affected by the reactions at the other positions, and may be removed without significantly affecting any other functionality of the molecule. One preferred type of protecting group is the tri-substituted silyl group, preferably the tri-loweralkyl silyl group or di-loweralkyl-aryl silyl group. Especially preferred examples are the trimethylsilyl, triethylsilyl, triisopropylsilyl, tert-butyldimethylsilyl and dimethylphenylsilyl groups.

The protected compound may be prepared with the appropriately substituted silyl trifluoromethanesulfonate, BSTFA, hexamethyldisilazane or silyl halide, preferably the silyl chloride. The reaction is carried out in an aprotic solvent such as methylene chloride, benzene, toluene, ethyl acetate, isopropyl acetate, tetrahydrofuran, dimethylformamide and the like. In order to minimize side reactions, there is included in the reaction mixture a base to react with the acid released during the course of the reaction. Preferred bases are amines such as imidazole, pyridine, triethylamine or dilsopropylethylamine and the like. The base is required in amounts equimolar to the amount of hydrogen halide liberated, however, generally several equivalents of the amine are employed. The reaction is stirred at from 0° C. to the reflux temperature of the reaction mixture and is complete from 1 to 24 hours.

The silyl group is removed by treatment of the silyl compound with anhydrous pyridine-hydrogen fluoride in tetrahydrofuran or dimethylsulfoxide or with tetraalkylammonium fluoride in tetrahydrofuran. The reaction is complete in from 1 to 24 hours at from 0° C. to 50° C. Alternatively, the silyl group may be removed by stirring the silylated compound in lower protic solvents such as methanol, ethanol, isopropanol and the like catalyzed by an acid, preferably a sulfonic acid monohydrate such as para-toluenesulfonic acid, benzenesulfonic acid, pyridinium para-toluenesulfonate or carboxylic acids such as acetic acid, propionic acid, monochloroacetic acid, dichloroacetic acid, trichloroacetic acid and the like. The reaction is complete in 1 to 24 hours at from 0° C. to 50° C.

Protecting groups that may also be suitably used in the preparation of compounds of the present invention may be found in standard textbooks such as Greene and Wutz, *Protective Groups in Organic Synthesis*, 1991, John Wiley & Sons, Inc.

Compounds of formula I where $R_1$ and $R_2$ together represent an oxime, $=NOR^a$, may be prepared by treating the appropriate oxo analog with $H_2NOR^a$ to produce the corresponding oxime. Oxime formation may be accomplished using techniques known to those skilled in the art, including, but not restricted to, the use of $H_2NOR^a$ either as the free base or as an acid addition salt such as the HCl salt, or an O-protected hydroxylamine such as O-trialkylsilylhydroxylamine, in a protic solvent such as methanol, ethanol, isopropanol and the like or aprotic solvents such as methylene chloride, chloroform, ethyl acetate, isopropyl acetate, tetrahydrofuran, dimethylformamide, benzene, toluene and the like, as appropriate. The reactions may by catalyzed by the addition of sulfonic acids, carboxylic acids or Lewis acids, including, but not limited to, benzenesulfonic acid monhydrate, para-toluenesulfonic acid monohydrate, acetic acid, zinc chloride and the like.

Similarly, compounds of formula I wherein $R_1$ and $R_2$ together represent $=NNR^cR^d$ may be prepared by treating the appropriate oxo analog with $H_2NNR^cR^d$ to give the corresponding hydrazones using conditions directly analogous to those described for oxime formation.

Compounds of formula I wherein one or both of the $===$ bonds represent a single bond may be prepared from the corresponding compound wherein $===$ is a double bond by conventional hydrogenation procedures. The double bonds may be hydrogenated with any of a variety of standard precious metal hydrogenation catalysts such as Wilkinson's catalyst, Pearlman's catalyst, 1–25% palladium on carbon, 1–25% platinum on carbon and the like. The reaction is generally carried out in a non-reducible solvents (either protic or aprotic) such as methanol, ethanol, isopropanol, tetrahydrofuran, ethyl acetate, isopropyl acetate, benzene, toluene, dimethylformamide and the like. The hydrogen source may be hydrogen gas from 1 to 50 atmospheres of pressure or other hydrogen sources such as ammonium formate, cyclohexene, cyclohexadiene and the like. The reduction also may be carried out using sodium dithionite and sodium bicarbonate in the presence of a phase transfer catalyst, in particular a tetraalkylammonium phase transfer catalyst, and the like. The reactions may be run from 0° C. to 100° C. and are complete in from 5 min to 24 hours.

Compounds of formula I wherein $R_2$ is OH and $R_1$ is H may be prepared from the corresponding ketone by treating the appropriate oxo analog with standard reducing agents including, but not restricted to, sodium borohydride, lithium borohydride, lithium aluminum hydride, potassium tri-sec-butyl borohydride, diisobutylaluminum hydride, diborane oxazaborolidines and alkylboranes (both achiral and chiral). These reactions are performed in a manner known to those skilled in the art and are carried out in non-reducible solvents such as methanol, ethanol, diethyl ether, tetrahydrofuran, hexanes, pentane, methylene chloride and the like. The reactions are complete in from 5 minutes to 24 hours at temperatures ranging from −78° C. to 60° C. Compounds of formula I wherein $R_2$ is OH, $R_1$ is H and $R^z$ contains $CH_2OH$ may be obtained by reacting the appropriate carboxylic acid or ester analog (e.g., where $R^z$ contains $CO_2H$ or $CO_2R^b$) with the more reactive reducing agents as described above, including lithium aluminum hydride, lithium borohydride and the like. Compounds of formula I wherein $R_2$ and $R_1$ together are oxo and $R^z$ contains $CH_2OH$ may be obtained by reacting the appropriate carboxylic acid (e.g., where $R^z$ contains $CO_2H$) with less reactive reducing agents such as diborane and the like.

Compounds of formula I wherein $R_2$ is OH and $R_1$ is other than H, may be prepared from the corresponding ketone by treating the appropriate oxo analog with a Grignard reagent $R_1MgBr$, or with a lithium reagent $R_1Li$. These reactions are performed in a manner known to those skilled in the art and preferably are performed in aprotic solvents such as diethyl ether, tetrahydrofuran, hexanes or pentanes. The reactions are complete in from 5 minutes to 24 hours at temperatures ranging from −78° C. to 60° C.

Preparation of 3"- or 1"-Aldehydes

The 3"- and/or 1"-aldehydes (compounds 1 and 2, respectively) may be prepared as described in Scheme I.

Thus, compound A may be treated with potassium permanganate under conditions known to those skilled in the art to yield the desired 3"- and 1"-aldehyde products. The potassium permanganate may be used stoichiometrically or in excess and in the presence of a solid support including but not restricted to, Celite, basic alumina, neutral alumina, acidic alumina, silica gel, clays and the like. Sodium permanganate or tetraalkylammonium permanganate (either preformed or generated in situ from a tetraalkylamonium salt and potassium permanganate) may be substituted for potassium permanganate. Suitable tetraalkylammonium salts include, but are not restricted to (n-Bu)$_4$NX, (PhCH$_2$)$_3$NMeX, (n-heptyl)$_4$NX, (PhCH$_2$)N(n-Bu)$_3$X, (n-dodecyl)$_3$NMeX, Adogen 464 and the like and where X=HO, SO$_4$, PF$_6$ and the like. The reaction to form aldehydes 1 and 2 may be performed in a variety of solvents or mixtures of solvents. These include both protic and aprotic solvents such as water, methylene chloride, chloroform, dichloroethane, +methanol, ethanol, tert-butanol, ether, tetrahydrofuran, benzene, pyridine, acetone and the like. The reactions may be performed at from −78° C. to 80° C. and are complete in from 5 minutes to 24 hours.

and di-substituted amides of compound 3 may be used in this reaction. These include, but are not restricted to, monosubstituted amides such as N-methyl, N-ethyl, N-propyl, N-butyl, tert-butyl, N-phenyl and the like or disubstituted amides such as N,N-dimethyl, N,N-diethyl, N-methyl-N-ethyl, N-methyl-N-phenyl and the like. Osmium tetroxide may be used either stoichiometrically or catalytically in the presence of an oxidant, including, but not restricted to, morpholine N-oxide, trimethylamine N-oxide, hydrogen peroxide, tert-butyl hydroperoxide and the like. The dihydroxylation reactions may be performed in a variety of solvents or mixtures of solvents. These include both protic and aprotic solvents such as water, methanol, ethanol, tertbutanol, ether, tetrahydrofuran, benzene, pyridine, acetone and the like. The reactions may be performed at from −78° C. to 80° C. and are complete in from 5 minutes to 24 hours. Diol product 4 may be converted into aldehydes 1 and 2 by treatment with an oxidizing agent, including, but restricted to, NaIO$_4$, HIO$_4$, MnO$_2$, Amberlite 904-NaIO$_4$ and the like, or preferably Pb(OAc)$_4$. These oxidative cleavage reactions may be performed in a variety of solvents or mixtures of solvents. These include both protic and aprotic solvents such

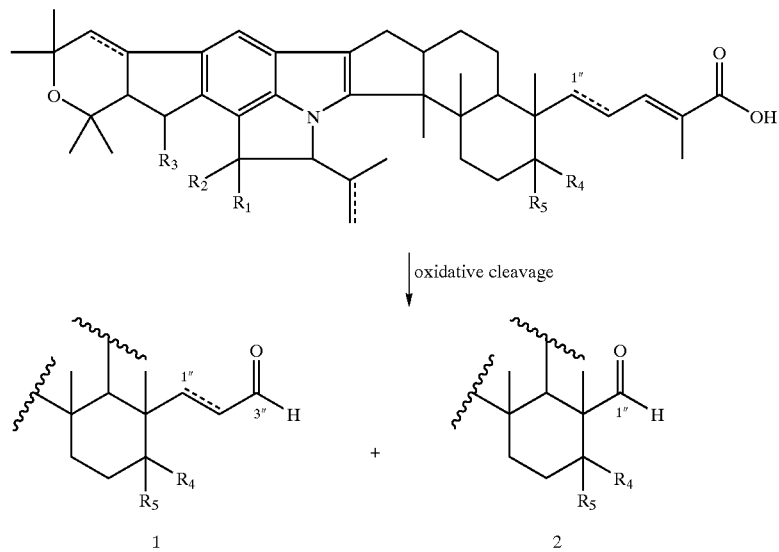

Aldehydes 1 and 2 may also be produced by treating compound 3 with osmium tetroxide under conditions known to those skilled in the art as shown in Scheme II below. Also produced during this reaction is the diol product 4. Monoas water, methanol, ethanol, tert-butanol, ether, tetrahydrofuran, benzene, pyridine, acetone and the like. The reactions may be performed at from −78° C. to 80° C. and are complete in from 5 minutes to 24 hours.

SCHEME II

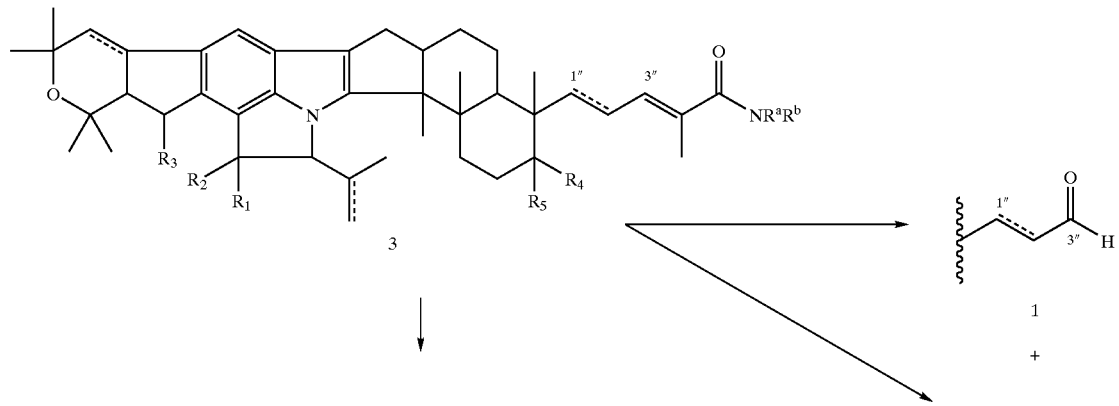

-continued

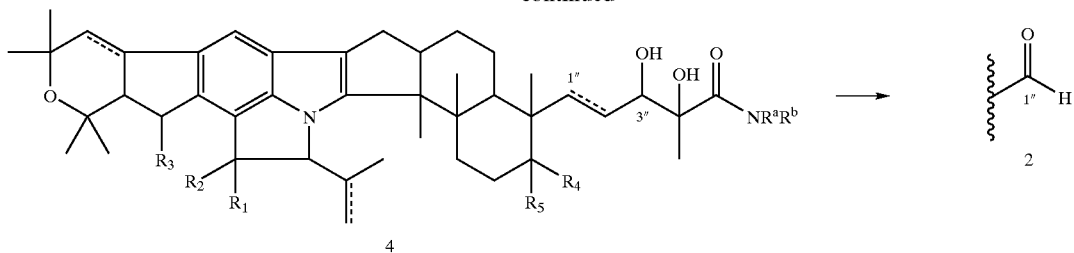

$R^a$ and $R^b$ are H or lower alkyl

Compounds of formula I where $R^z$ is $CO_2H$ are prepared from the 3'-aldehdye of compound 1. The 3"-aldehyde of compound 1 may be oxidized to generate the corresponding 3"-carboxylic acid (compound 5) using standard oxidizing conditions known to those skilled in the art. The reaction is carried out using at least one equivalent of an oxidant in protic or aprotic solvents. Oxidizing agents include, but are not restricted to, AgO/NaCN, NBS/$H_2O$, $NaClO_2$/isoprene, $MnO_2$, $MnO_2$/NaCN, $NaClO_2$/(K)$NaH_2PO_4$/isoprene, and the like. These oxidation reactions may be performed in solvents or mixtures of solvents including but not restricted to, chloroform, carbon tetrachloride, water, tetrahydrofuran, benzene, ethyl acetate, isopropyl acetate and the like, or most preferably methylene chloride and the reaction proceeds from temperatures of 0° C. to 75° C.

diphenylphosphoryl azide (DPPA), 2-(1H-benzotriazole-1-yl)-1,1,3,3-tetramethyluronium hexafluorophosphate (HBTU), O-benzotriazol-1-yl-N,N,N',N'-bis(pentamethylene)uronium hexafluorophosphate and 2-chloro-1-methyl-pyridinium iodide. The amide-forming reactions may be facilitated by the optional addition of N-hydroxybenzotriazole or N-hydroxy-7-aza-benzotriazole. The amidation reaction is generally performed using at least one equivalent (although several equivalents may be employed) of amine bases such as triethylamine, diisopropyl-ethylamine, pyridine, N,N-dimethylaminopyridine and the like. The carboxyl group may be activated for amide bond formation via its corresponding acid chloride or mixed anhydride, using conditions known to those skilled in the art. These amide-forming

SCHEME III

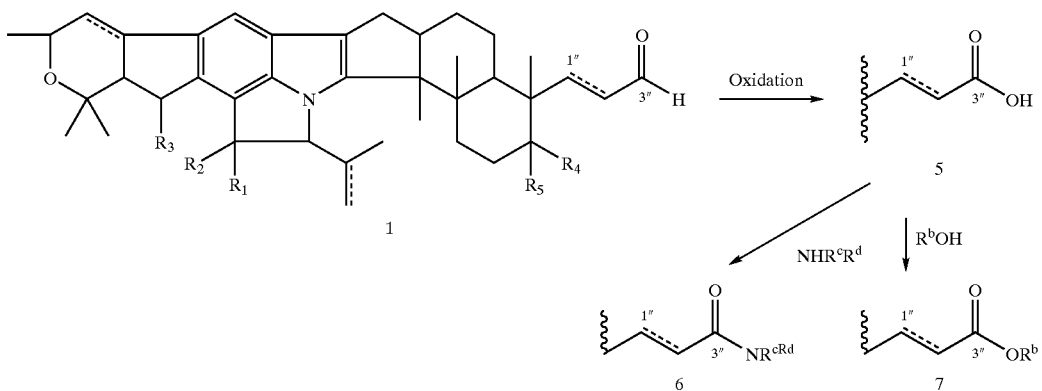

Compounds of formula I where $R^z$ contains $C(O)N(OR^b)R^c$ or $C(O)NR^cR^d$ (such as compound 6) are prepared from the corresponding carboxylic acid (such as compound 5) using standard amide-forming reagents known to those skilled in the art. The reaction is carried out using at least one equivalent of an amine nucleophile, $HN(OR^b)R^c$ or $HNR^cR^d$, although preferably ten to one hundred equivalents of amine nucleophiles are employed. Amide-forming reagents include, but are not restricted to, dicyclohexylcarbodiimide, 1-(3-dimethylaminopropyl)-3-ethyl-carbodiimide hydrochloride (EDC.HCl), diisopropylcarbodiimide, benzotriazol-1-yloxy-tris(dimethylamino)phosphonium hexafluorphosphate (BOP), bis(2-oxo-3-oxazolidinyl)phosphinic chloride (BOP-Cl), benzotriazole-1-yl-oxy-tris-pyrrolidino-phosphonium hexafluorophosphate (PyBOP), chloro-tris-pyrrolidino-phosphonium hexafluorophosphate (PyCloP), bromo-tris-pyrrolidino-phosphonium hexafluoro-phosphate (PyBroP), reactions are carried out in aprotic solvents such as methylene chloride, tetrahydrofuran, diethyl ether, dimethylformamide, N-methylpyrrolidine and the like at −20° C. to 60° C. and are complete in 15 minutes to 24 hours.

Compounds of formula I where $R^z$ contains $CO_2R^b$ (such as compound 7) are prepared from the corresponding carboxylic acid (such as compound 5) using standard ester-forming reagents known to those skilled in the art. The esterification reaction is carried out using at least one equivalent of an alcohol, $HOR^b$, although preferably ten to one hundred equivalents of alcohol are used; the esterification also may be carried out using the alcohol as solvent. Esterification reagents include, but are not restricted to, dicyclohexylcarbodiimide, 1-(3-dimethylaminopropyl)-3-ethylcarbodiimide hydrochloride (EDC.HCl), diisopropylcarbodiimide, benzotriazol-1-yloxy-tris(dimethylamino)phosphonium hexafluorphosphate (BOP), bis(2-oxo-3-oxazolidinyl)phosphinic chloride (BOP-Cl), benzotriazole-1-yl-oxy-tris-pyrrolidino-phosphonium hexafluorophosphate (PyBOP), chloro-tris-pyrrolidinophosphonium hexafluorophosphate (PyCloP), bromo-tris-pyrrolidino-phosphonium hexafluorophosphate (PyBroP), diphenylphosphoryl azide (DPPA), 2-(1H-benzotriazole-1-yl)-1,1,3,3-tetramethyluronium hexafluorophosphate (HBTU), O-benzotriazol-1-yl-N,N,N',N'-bis(pentamethylene)uronium hexafluorophosphate and 2-chloro-1-methylpyridinium iodide. The ester-forming reactions may be facilitated by the optional addition of N-hydroxybenzotriazole, N-hydroxy-7-aza-benzotriazole, 4-(N,N-dimethylamino)pyridine or 4-pyrrolidinopyridine. The reaction is generally performed using at least one equivalent (although several equivalents may be employed) of amine bases such as triethylamine, dilsopropylethylamine, pyridine and the like. The carboxyl group may be activated for ester bond formation via its corresponding acid chloride or mixed anhydride, using conditions known to those skilled in the art. These ester-forming reactions are carried out in aprotic solvents such as methylene chloride, tetrahydrofuran, diethyl ether, dimethylformamide, N-methylpyrrolidine and the like at temperatures ranging from −20° C. to 60° C. and are complete in 15 minutes to 24 hours.

Compounds of formula I wherein one or more of $R_2$, $R_3$, and $R_4$ is $OR^a$, $OCO_2R^b$ or $OC(O)NR^cR^d$, and/or where Z is $CH_2OR^a$, $CH_2OCO_2R^b$ or $CH_2OC(O)NR^cR^d$ may be prepared using known methods for acylation, sulfonylation and alkylation of alcohols. Thus, acylation may be accomplished using reagents such as acid anhydrides, acid chlorides, chloroformates, carbamoyl chlorides, isocyanates and amine bases according to general procedures known to those skilled in the art. Sulfonylations may be carried out using sulfonyl chlorides or sulfonic anhydrides. The acylation and sulfonylation reactions may be carried out in aprotic solvents such as methylene chloride, chloroform, pyridine, benzene, toluene and the like. The acylation and sulfonylation reactions are complete in from 15 minutes to 24 hours at temperatures ranging from −20° C. to 80° C. The degree of acylation, sulfonylation and alkylation will depend on the amount of the reagents used. Thus, for example, using one equivalent of an acylating reagent and one equivalent of nodulisporic acid results in a product mixture containg 4- and 20-acylated nodulisporic acid; such a mixture may be separated by conventional techniques such as chromatography.

Compounds of formula I wherein one or more of $R_2$, $R_3$, $R_4$ is $OR^a$ and/or where $R^x$ contains $CH_2OR^a$, may be prepared using methods known to those skilled in the art for the alkylation of alcohols. Thus, alkylation may be accomplished using reagents including, but not restricted to, halides $IR^a$, $BrR^a$, $ClR^a$, diazo reagents $N_2R^a$, trichloroacetimidates $R^aOC(NH)CCl_3$, sulfates $R^aOSO_2Me$, $R^aOSO_2CF_3$, and the like. The alkylation reactions may be facilitated by the addition of acid, base or Lewis acids, as appropriate. The reactions are performed in aprotic solvents such as methylene chloride, chloroform, tetrahydrofuran, benzene, toluene, dimethylformamide, N-methylpyrrolidine, dimethyl sulfoxide, hexamethylphosphoramide and are complete at from 0° C. to the reflux temperature of the solution from 15 minutes to 48 hours.

Compounds of formula I may be prepared where Z is $CH_2OH$ (e.g. compound 8) may be prepared by treatment of compound 1 with appropriate reducing agents (Scheme IV). Suitable hydride sources include, but are not limited to $NaBH_4$, $NaCNBH_3$, $LiBH_4$, $LiAlH_4$, $NaBH(OAc)_3$, DIBAL-H, $nBu_3SnH$, $Et_3SiH$, diborane, Alpine borane, $BH_3 \cdot Me_2S$, L-Selectride, alkyl borane reagents, or most preferably, 9-BBN. The reduction reaction may be performed in protic or aprotic solvents, or mixtures of solvents, and include, but are not limited to, methanol, ethanol, methylene chloride, toluene, diethyl ether, dioxane and the like, or most preferable, THF and the reactions are conducted from −78° C. to 100° C. and are complete in from 2 minutes to 24 hours. Starting compound 1 may have its C7- and C24-hydroxyl groups protected with silyl protecting groups. The newly formed 3"-hydroxyl of compounds of formula 8 may be acylated with suitable acylating agents including, but not restricted to, acid chlorides, carbamoyl chlorides, isocyanates, chloroformates, carboxylic acids, sulfonyl chlorides and the like as described previously.

SCHEME IV

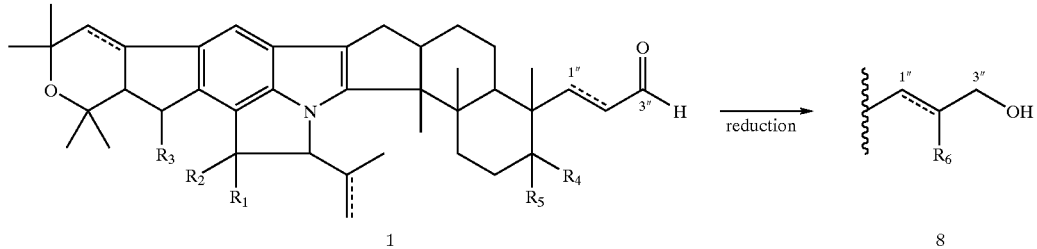

Compound 1 may be converted to compound 9 using appropriate olefin-forming reaction conditions known to those skilled in the art as shown in Scheme V. Reagents for these reactions include, but are not restricted to, the use of stabilized and unstabilized Wittig reagents, Horner-Emmons reagents, Tebbe reagent, Petassis reagent, aldol reactions, Knoevenagel reactions, Peterson olefinations and the like. Starting compound 1 may have its C7- and C24-hydroxyl groups protected with silyl protecting groups. The compounds of formula 9 shown below may be acyclic or cyclic, depending on the chain-extending reagents utilized. Alternatively, compounds of formula 9 may be acyclic but further modified to yield cyclic products. Wittig reagents may be readily prepared by reacting $Ph_3P$ with an appropriate halide under conditions known to those skilled in the art, such as those described by Ikuta, H. et al. (*J. Med. Chem.* 1987, 30, 1995–1998) or Larock, R. C. (Comprehensive Organic Transformations, VCH Publishers, Inc.: New York, N.Y., 1989, Chapter 4). Alternatively, stabilized Wittig reagents may be prepared as described by Bestmann, H. J. and Schulz, H. (*Chem. Ber.* 1964, 97, 11) wherein an appropriate unstabilized Wittig reagent $Ph_3P=C(R^a)_2$ is reacted with a suitable chloroformate to yield Ph$_3$P=C(R$^a$)$_2$CO$_2$R$^b$ or as described by the conjugate addition of Ph$_3$P to N—R$^c$ substituted maleimides. The olefination reactions may be performed in a variety of solvents or mixtures of solvents. These include both protic and aprotic solvents such as water, methanol, ethanol, tert-butanol, ether, acetonitrile, tetrahydrofuran, methylene chloride, chloroform, 1,2-dichloroethane, benzene, toluene, pyridine, acetone and the like. Suitable bases include, but are not limited to, NaOH, KOH, NaOEt, KOtBu, LDA, LHMDS, NaHMDS, KHMDS, pyridine, piperidine, morpholine, lutidine, DMAP, DBU and the like. The reactions may be performed at from −78° C. to 120° C. and are complete in from 5 minutes to 24 hours. The compounds of formula 9 may be further elaborated by Stille, Heck and Suzuki couplings where R$_6$ contains OTf, B(OH)$_2$, Sn(n-Bu)$_3$, SnMe$_3$, OP(O)(OPh)$_2$, I, Br, or Cl.

dimethylformamide, dimethylsulfoxide, benzene, toluene and the like. The urea-forming reactions may be performed from 0° C. to 100° C. and are complete in 15 minutes to 24 hours. Compounds of formula 11 may be reacted in an aprotic solvent such as benzene, toluene, methylene chloride, 1,2-dichloroethylene, dimethylformamide and the like, with an alcohol R$^b$OH, such as methanol, ethanol, benzyl alcohol, 2-trimethylsilylethanol, 2,2,2-trichloroethanol, methyl glycolate, phenol and the like to yield carbamates of formula 13. Similarly, compounds of formula 14 may be prepared by substituting HSR$^b$ for HOR$^b$ in the reaction. The addition of one or more equivalents of an amine base such as triethylamine, diisopropylethylamine, pyridine and the like may be employed to accelerate carbamate formation. The carbamate-forming reactions may be performed from 0° C. to 100° C. and are complete in 15

SCHEME V

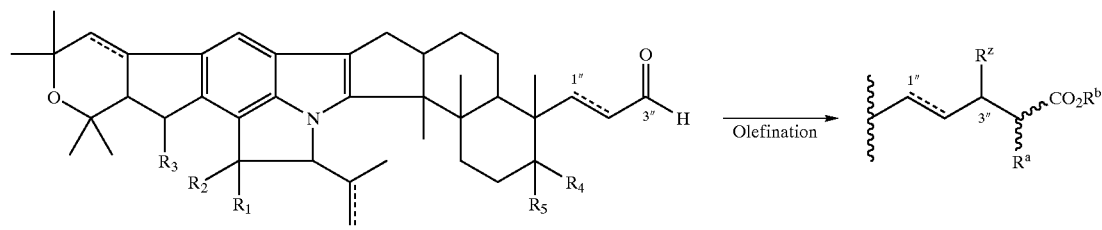

Compounds of formula 9 are useful as intermediates in the preparation of corresponding amides. The esters of compound 9 (where R$^b$≠H) may be hydrolyzed by treatment with hydroxide or ammonium hydroxide in a protic solvent such as methanol, ethanol, water, tetrahydrofuran/water or dimethylformamide/water and the like at from 0° C. to the reflux temperature of the solution. Alternatively, the resultant esters may be transesterified by treatment with a Lewis acid, including, but not restricted to, magnesium chloride, magnesium bromide, aluminum chloride, zinc chloride, Otera's catalyst, and the like, or preferably titanium tetraisopropoxide in a protic solvent such as methanol, ethanol, isopropanol, 2-trimethylsilylethyl alcohol and the like, or preferably allyl alcohol. The transesterification reactions are complete in from 1 to 24 hours at 0° C. to the reflux temperature of the solution, preferably 110° C. The allyl ester (e.g. R$^b$=—CH$_2$CH=CH$_2$) may be removed by treatment with Pd° using conditions known to those skilled in the are to generate the free carboxylic acid (e.g. R$^b$=H). Pd° reagents include, but are not restricted to, PdCl$_2$(PPh$_3$)$_2$, Pd(OAc)$_2$(PPh$_3$)$_2$, PdCl$_2$(PhCN)$_2$, Pd(OAc)$_2$, PdCl$_2$(P(o-tolyl)$_3$)$_2$, PdCl$_2$(DDPF), Pd$_2$(dba)$_3$, and the like, or preferably Pd(PPh$_3$)$_4$. The carboxylic acid of compound 9 may be converted into corresponding amides using conventional amide formation procedures as described (vida supra).

In Scheme VI, compound 9 (in which R$^b$ is H) is treated with diphenylphosphoryl azide to provide an intermediate acyl azide (compound 10). Heating of compound 10 in an aprotic solvent such as benzene, toluene, dimethylformamide and the like results in a rearrangement yielding an isocyanate, compound 11. The isocyanate-forming reactions may be performed from 0° C. to 120° C., preferably at 80° C., and are complete in 15 min to 24 hours. Compounds of formula 12 may be prepared when compounds of formula 11 are reacted with an appropriate amine HNR$^c$R$^d$ in an aprotic solvent such as methylene chloride, tetrahydrofuran, minutes to 24 hours. Compounds of formula 15 may be prepared by treatment of compounds of formula 11b with R$^a$MgI, R$^a$MgCl, R$^a$Li, (R$^a$)$_2$CuLi or preferably R$^a$MgBr, as illustrated below. Compounds of formula 11 may be reacted in an aprotic solvent, or mixture of solvents, such as including, but not restricted to, dioxane, pentane, hexane, DMSO, HMPA, or NMP, and the like, or preferably tetrahydrofuran. The reactions may be performed from −78° C. to 100° C. and is complete in from 5 minutes to 12 hours.

SCHEME VI

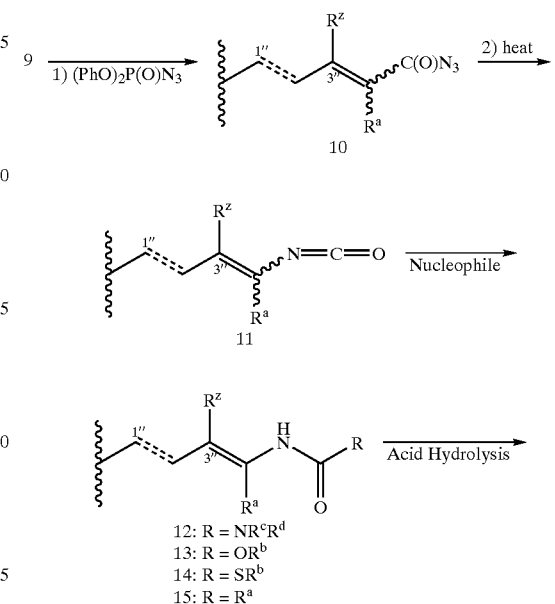

12: R = NR$^c$R$^d$
13: R = OR$^b$
14: R = SR$^b$
15: R = R$^a$

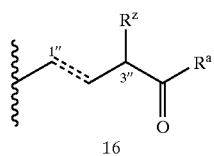

Compounds of formula 16 containing a ketone at C4" may be prepared as illustrated in Scheme VI by acid-catalyzed hydrolysis of compounds of formula 11, 12, 13 or 14. Suitable acids for the hydrolysis include, but are not restricted to, p-toluenesulfonic acid, benzene sulfonic acid, acetic acid, proprionic acid, citric acid, camphor sulfonic acid, hydrochloric acid, sulfuric acid, nitric acid, or preferably, pyridium.p-toluenesulfonate. Suitable solvents for this hydrolsis include solvents, or mixtures of solvents, such as water, ethanol, n-propanol, iso-propanol, acetone, methylethyl ketone, methylene chloride, chloroform, toluene, tetrahydrofuran or dioxane and the like, or preferably methanol. The reactions may be performed from −20° C. to 100° C. or preferably at room temperature and are complete in from 5 min to 24 hours.

As illustrated in Scheme VII the procedure described in Scheme VI may be used to prepare compound 18 from compound 5a may be performed at from −78° C. to 50° C., or most preferably −78° C. The hydroxyl at C3" of compounds of formula 19 may be sulfonylated directly or following isolation and/or purification using aryl- or alkylsulfonyl chlorides, aryl or alkylsulfonic anhydrides, trifluoromethanesulfonic anhydride, trifluoromethanesulfonyl chloride, or most preferably methanesulfonyl chloride in the presence of bases such as, but not limited to, pyridine, lutidine, DMAP, DIEA, DBU and the like, or most preferably $Et_3N$. The reaction may be performed at from −78° C. to 50° C., or most preferably 0° C. Formation of unsaturated compounds of formula 20 may be performed using by stirring compounds of formula 19 in lower protic solvents such as water, ethanol, isopropanol, propanol, allyl alcohol and the like or most preferably methanol, catalyzed by an acid, preferably a sulfonic acid monohydrate such as para-toluenesulfonic acid, benzenesulfonic acid, pyridinium para-toluenesulfonate or carboxylic acids such as acetic acid, propionic acid, monochloroacetic acid, dichloroacetic acid, trichloroacetic acid, or inorganic acids such as $HBF_4$, $H_2SO_4$ and the like or most preferably HCl. The reaction is complete in 1 to 24 hours at from 0° C. to 50° C. Compounds of formula 21a may be transesterification by heating 21a in an alcoholic solvent with a Lewis acid catalyst from 50° C. to 200° C., or most preferably 120° C. Suitable alcohols include methanol, ethanol, allyl alcohol, propanol, benzyl

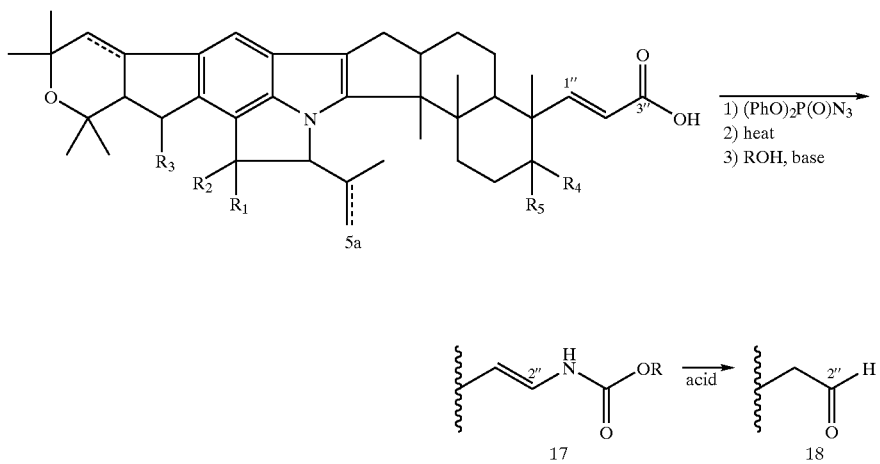

Scheme VII

As shown in Scheme VIII, compounds may be prepared containing $CO_2R^b$ (compound 21a) or $C(O)NR^cR^d$ (compound 21b) at C4". Treatment of compound 1 with $NCCH_2N=CPh_2$ and a base leads to the formation of compounds of formula 19. The reaction may be performed in solvents or mixtures of solvents including, but not limited to, diethyl ether, dioxane, dimethyl ether, NMP, DMSO, HMPA, methanol, ethanol, tert-butanol, water, benzene, toluene and the like, or most preferably tetrahydrofuran. Appropriate bases, or mixtures of bases, for performing the reaction include pyridine, piperidine, morpholine, $Et_3N$, $Et_2NiPr$, DBU, LDA, NaHMDS, KHMDS, NaOH, NaOEt, NaOtBu, KOtBu or most preferably LHMDS. The reaction alcohol, 2-trimethylsilylethylalcohol and the like. These reactions may also be performed using a co-solvent such as benzene or toluene. Suitable Lewis acids include $MgCl_2$, $MgBr_2$, $AlCl_3$, $ZnI_2$ and the like, or most preferably, $Ti(OiPr)_4$. Standard conditions for these reactions are described in Seebach, D. et al., Synthesis (1982), 138–141. Deprotection of compounds of formula 21a where $R^b$ is $-CH_2CH=CH_2$ will generate the corresponding carboxylic acid (e.g. compounds of formula 21a where $R^b$ is a hydrogen) proceeds as described previously. The resultant carboxylic acid may be converted into the corresponding amides (compound 21b) using conditions previously described.

SCHEME VIII

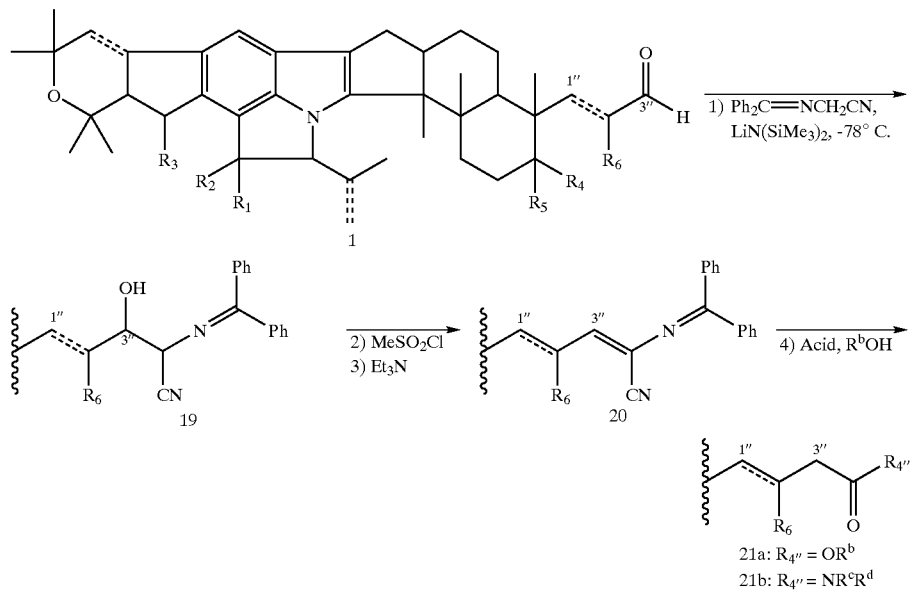

Scheme IX illustrates an alternative method for the preparation of compounds of formula 21a. Acylation of compounds of formula 8 containing unsaturation at C1"–2" leads to the formation of compounds of formula 22a and 22b. Suitable acylating agents include, but are not limited to, ethyl chloroformate, propylchloroformate, phenylchloroformate, para-nitrophenylchloroformate, dimethyl pyrocarbonate, diethyl pyrocarbonate, proprionyl chloride, acetic anhydride, proprionic anhydride, benzoyl chloride and the like, or most preferably acetyl chloride or methyl chloroformate. Treatment of compound 22a or 22b in the presence of a $Pd^0$ source, carbon monoxide and an alcohol ($HOR^b$), preferably methanol, will lead to the formation of 21a. Suitable $Pd^0$ sources include, but are not limited to, $PdCl_2(PPh_3)_2$, $Pd(OAc)_2(PPh_3)_2$, $PdCl_2(PhCN)_2$, $Pd(OAc)_2$, $PdCl_2(P(o\text{-tolyl})_3)_2$, $PdCl_2(DDPF)$, $Pd_2(dba)_3$, and the like, or most preferably $Pd(PPh_3)_4$. This reaction proceeds at temperatures from room temperature to 150° C. and is complete in from 15 min to 24 h.

SCHEME IX

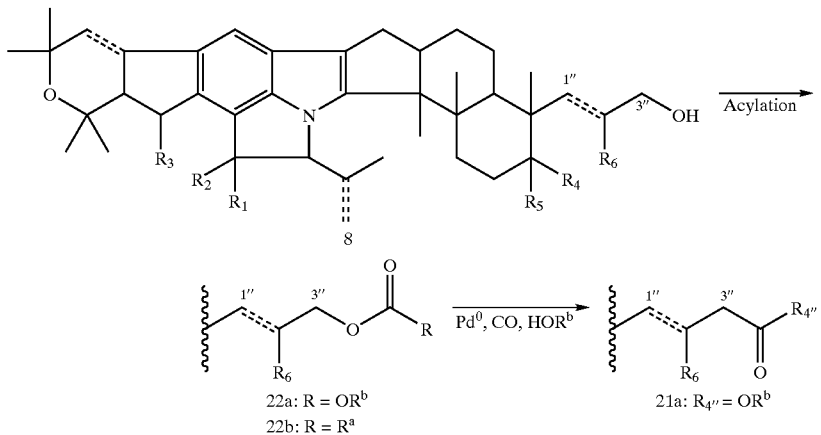

Compounds of formula 23 may be prepared using the Passerrini reaction wherein compound 1 is treated with a carboxylic acid, an isonitrile in a protic solvent as shown in Scheme X. Suitable isonitriles for the Passerrini reaction, include, but are not limited to, methyl isonitrile, ethyl isonitrile, isopropyl isonitrile, tert-butyl isonitrile, cyclohexenyl isonitrile, benzyl isonitriles and ethyl isonitriloacetate and the like. The Passerrini reaction may be performed in protic solvents or mixtures of solvents, including, but not limited to, methanol, ethanol, isopropanol, tert-butanol or water as well as aprotic solvents, including, but not limited to methylene chloride, DMSO, DMF, NMP, THF, chloroform, toluene and the like. The reaction proceeds at temperatures from 0° C. to 80° C. but most preferably at room temperature. Suitable carboxylic acids include, but are not limited to acetic acid, proprionic acid, formic acid, alpha-chloroacetic acid, alpha-methoxyacetic acid, butyric acid, benzoic acid and the like. Substitution of a sulfonic acid and an amine base for the carboxylic acid leads to the formation of compounds of formula 24. Suitable sulfonic acids include, but are not limited to benzene sulfonic acid or methane sulfonic acid, and the like or most preferably toluene sulfonic acid. Suitable amine bases include, but are not limited to, $Et_3N$, DIEA, DBU, lutidine, imidazole, quinoline and the like, or most preferably pyridine. Suitable protic solvents for the formation of compound 24 include, but are not limited to, water, methanol, ethanol, n-propanol, butanol, isopropanol, allyl alcohol, tert-butanol, 2,2,2-trifluoroethanol, phenol, benzyl alcohol, ethylene glycol, methyl glycolate and the like. The Passerrini reaction may form a mixture of stereoisomers at C3". The 3"-acylated alcohol of compounds of formula 23 may be deprotected by heating 23 in a protic or aprotic solvent with a Lewis acid catalyst (transesterification) to yield compounds of formula 24 where $R^b$=H. This is accomplished using conditions described for the tranesterification of compounds of formula 9 in Scheme V. The resultant 3"-alcohol may be acylated with suitable acylating agents including, but not restricted to, acid chlorides, carbamoyl chlorides, sulfonyl chlorides, isocyanates and the like, as described previously.

enyl isonitrile, benzyl isonitrile and ethyl isonitrilo-acetate and the like. The Ugi reaction may be performed in protic solvents or mixtures of solvents, including, but not limited to, methanol, ethanol, isopropanol, tert-butanol or water as well as aprotic solvents, including, but not limited to methylene chloride, DMSO, DMF, NMP, THF, chloroform, toluene and the like at temperatures from 0° C. to 80° C. but most preferably at room temperature. Suitable carboxylic acids include, but are not limited to acetic acid, proprionic acid, formic acid, alpha-chloroacetic acid, alpha-methoxyacetic acid, butyric acid, benzoic acid and the like. The Ugi reaction may be facilitated by the use of a drying agent in the reaction such as 4 Å molecular sieves. Performing the Ugi reaction employing an ortho-amino-heterocycle, an isonitrile and no carboxylic acid in a protic solvent leads to the formation of compounds of formula 26. Suitable ortho-amino-heterocycles include, but are not limited to, 2-aminopyridine, 2-aminopyrazine, 2-aminopyrimidine, 2-aminothiazole, 4-aminothiazole, 2-aminoimidazole, 2-aminooxazole, 2-amino-5-carboxamido-pyridine and the like. The ortho-amino-heterocycles may be additionally substituted with halogens, nitro groups, alkyl groups, alkoxy groups, mono-, di- and tri-fluouroalkyl groups, aryl and heteroaryl groups and the like. The Ugi reaction may form a mixture of stereolsomers at C3".

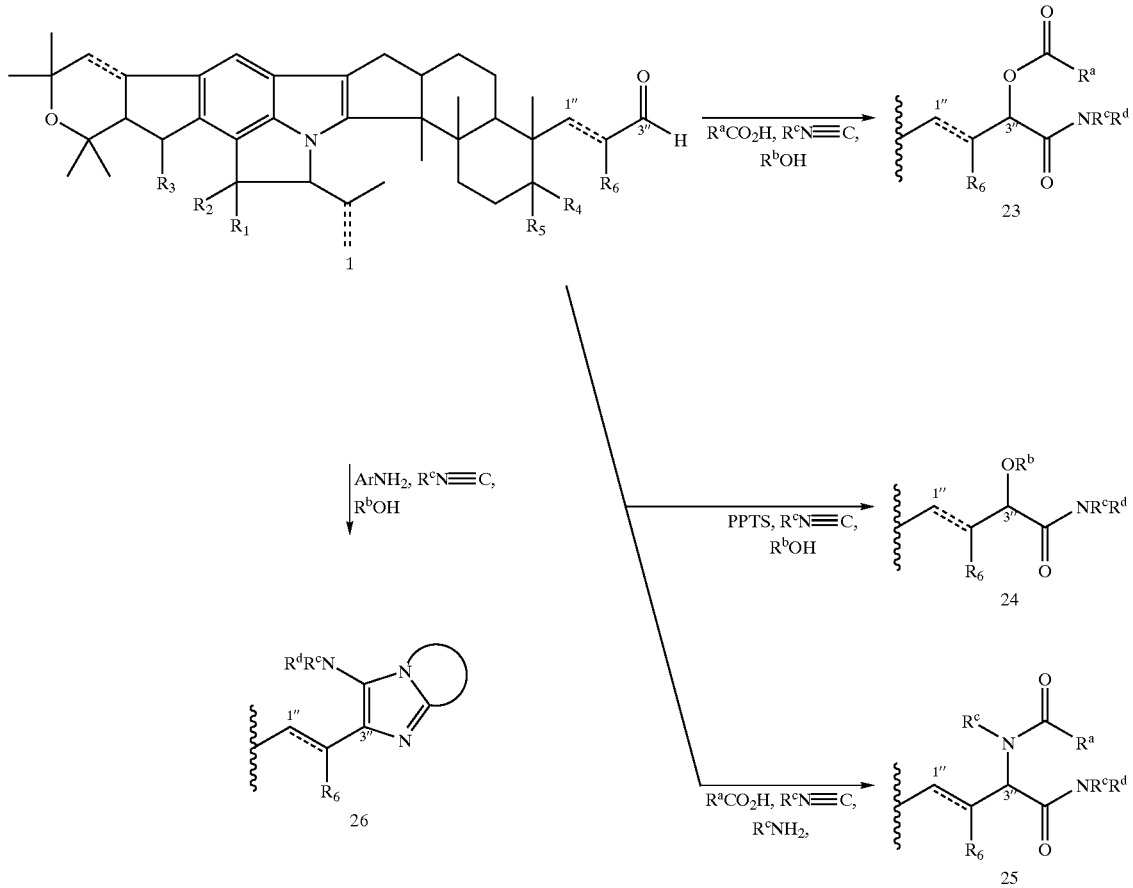

Compounds of formula 25 may be prepared using the Ugi reaction wherein compound 1 s treated with a carboxylic acid, an isonitrile and an amine in a protic solvent as shown in Scheme X. Suitable isonitriles for the Ugi reaction, include, but are not limited to, methyl isonitrile, ethyl isonitrile, isopropyl isonitrile, tert-butyl isonitrile, cyclohex- Heterocycles of formula 28 and 29 may be prepared as illustrated in Scheme XI. Protection of the C7 and C24 alcohols of compound 1 (not shown) followed by oxidation of the C3"-aldehyde yields silyl-protected compounds of formula 5. Suitable protecting groups for the C7 and C24-alcohols include, but are not limited to, $Me_3Si$—, tert-Bu (Me₂)Si—, (nPr)₃Si—, (iPr)₃Si—, Ph(Me₂)Si and the like or most preferably Et₃Si—. Suitable oxidizing agents include, but are not limited to, KMnO₄, NaMnO₄, CrO₃, AgO, Ag₂O, K₂Cr₂O₇, MnO₂/NaCN, MnO₂/Me₃SiCN and the like or most preferably NaClO₂. Amide generation using beta-hydroxy amines proceds as described previously to form 27. Cyclization was effected by treatment of 27 with dehydrating agents, such as Martin sulfurane or Burgess reagent to obtain compounds of formula 28. Aromatization of 28 to produce 29 was acheived using DBU and BrCCl₃. An additional method to prepare compounds of formula 29 was accomplished by oxidation of the beta-hydroxyl of compounds of formula 27 to the corresponding carbonyl using Dess-Martin reagent, followed by cyclo-dehydration using Ph₃P/BrCl₂CCCl₂Br/Et₂NiPr. For compounds of formula 28 or 29 where $R_\alpha$ or $R_\beta$ contains an ester functional, this moiety may be transesterified to the corresponding allyl ester and further elaborated via its to yield the corresponding carboxylic acids and amide derivatives as previously described. Substitution of 1,3-aminoalcohols for the beta-hydroxy amines in the reactions illustrated in this scheme would yield the 6-membered version of compounds of formula 28.

previously protected at the C7 and C24 hydroxyls with trialkyl silyl groups with trifluoromethanesulfonic anhydride in the presence of an amine base followed by addition of appropriately substituted beta-mercapto amines produces thiazolines 30. Suitable amine bases include, but are not limited to, Et₃N, DIEA, DBU, lutidine and the like or more preferably pyridine. Suitable protecting groups for the C7 and C24-alcohols include, but are not limited to, Me₃Si—, tert-Bu(Me₂)Si—, (nPr)₃Si—, (iPr)₃Si—, Ph(Me₂)Si and the like or most preferably Et₃Si—. This reaction proceeds in solvents such as MeCN, ClCH₂CH₂Cl, toluene, diethyl ether, THF, and the like or most preferably CH₂Cl₂. Aromatization of compounds of formula 30 to produce compounds of formula 31 was achieved using DBU and BrCCl₃ in the presence of a desiccant such as powdered 4Å molecular sieves. The oxidation (aromatization) reaction may be performed in solvents, including, but not limited to, MeCN, CH₂Cl₂, ClCH₂CH₂Cl, toluene, diethyl ether, THF, and the like, or more preferably, dioxane. This reaction proceeds at temperatures from −78° to 100° C. For compounds of formula 30 or 31 where $R_{60}$ or $R_{62}$ contains an ester functional, this moiety may be transesterified to the corre-

SCHEME XI

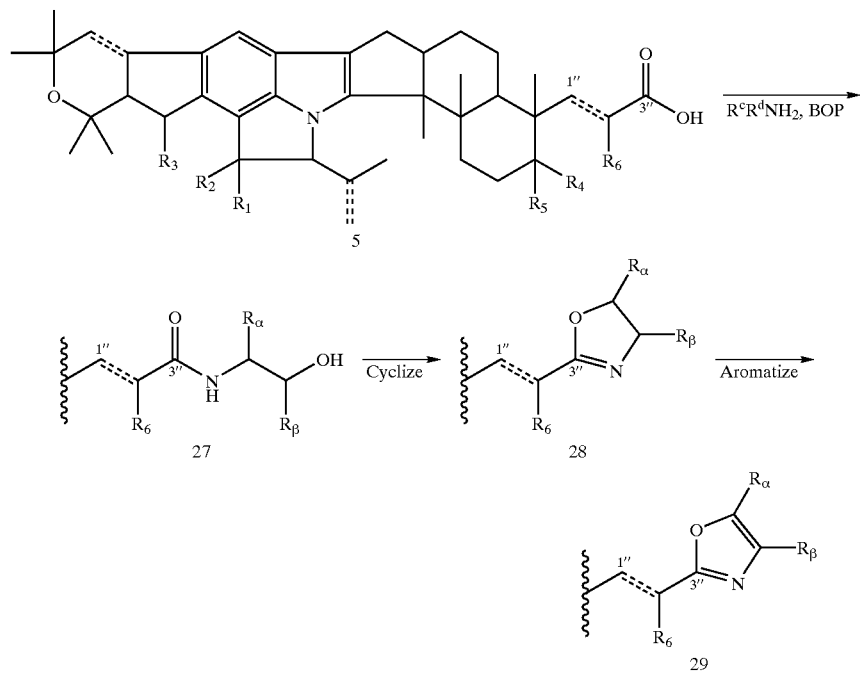

Compounds of formula 30 and 31 were prepared as illustrated in Scheme XII. Treatment of a C3"-dialkyl amide (e.g. compound 6 where both $R^c$ and $R^d$ are alkyl groups)

sponding allyl ester and further elaborated via its to yield the corresponding carboxylic acids and amide derivatives as previously described.

SCHEME XII

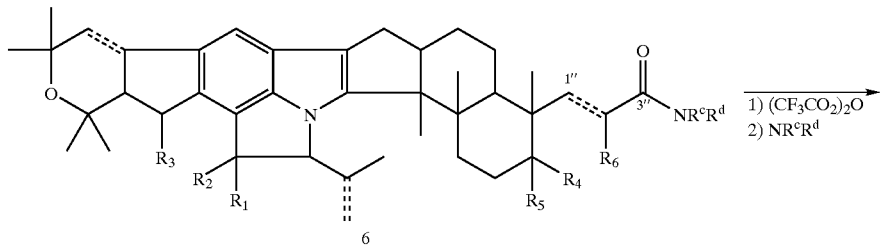

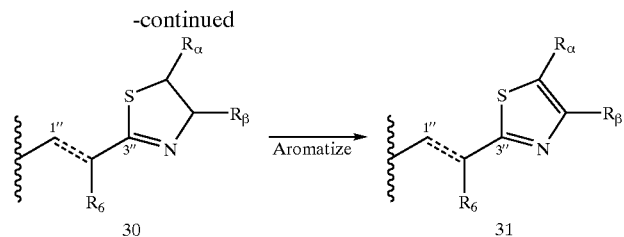

Compounds of formula 32 may be prepared from compounds of formula 1 as illustrated in Scheme XIII. Treatment of compound 1 with a suitable hydroxyl amine to form an intermediate 3"-nitonate (compound not shown) followed by N-substituted maleimides yields the 1,3-dipolar cycloaddition product 32. Suitable hydroxyl amines for this reaction include, but are not limited to, N-hydroxy-methyl-amine, N-hydroxy-ethylamine, N-hydroxy-benzylamine, N-hydroxyproylamine, N-hydroxyaniline, methyl N-hydroxy-glycinate and the like. Additional dipolarophiles may be substituted for the N-substituted maleimides used in this dipolar cycloaddition reaction. Suitable additional dipolaiophiles include, but are not restricted to, methyl vinyl ketone, cyclohexenone, cyclopentenone, methyl acrylate, dimethyl fumarate, butenyl lactone, methyl propenylate, methyl cinnamylate, and the like. Suitable solvents for nitronate formation in include protic and aprotic solvents or mixtures thereof and include, but are not restricted to, methylene chloride, chloroform, nitromethane, nitroethane, methanol, ethanol, toluene, benzene, acetonitrile, tetrahydrofuran and the like or most preferably pyridine. The nitronate forming reaction is complete in from 15 min to 24 h at temperatures from 0° C. to 120° C. Preferable solvents for the dipolar cycloaddition reaction include, but are not restricted to, methylene chloride, chloroform, nitromethane, nitroethane, toluene, tetrahydrofuran or most preferably acetonitrile. The dipolar cycloaddition reaction may form a mixture of stereoisomers at C3". The dipolar cycloaddition reaction with the N-substituted maleimide is complete in from 15 min to 24 h at temperatures from 0° C. to 120° C.

formula 1. The reductive amination may proceed using a variety of representative mono- and di-substituted amines, including but not limited to, ammonium hydroxide, methyl amine, ethyl amine, benzyl amine and substituted benzyl amines, dimethyl amine, ethylene diamine, N-ethylethylenediamine, 2-aminoethanol, D-alanine methyl ester, 2-amino-1-phenyl-propan-1-ol, 2-amino-2,2-dimethylethanol, ortho-hydroxy-aniline, 4-phenyl-2-hydroxy-aniline, piperidine, tert-butyl amine, aniline and substituted anilines, methyl glycinate, aminoacetonitrile, methoxyl amine, methoxylamine, bis(2,2,2-trifluoroethyl)amine and the like. Suitable solvents for this reaction include but are not restricted to ethanol, toluene, tert-butanol, tetrahydrofuran, benzene, acetonitrile, methylene chloride or most preferably methanol. The reductive amination reaction may be facilitated by the addition of a dehydrating agent such as 4 angstrom sieves or the like. Suitable hydride sources include, but are not limited to $NaCNBH_3$, $LiBH_4$, $LiAlH_4$, $NaBH(OAc)_3$, DIBAL-H, $nBu_3SnH$, $Et_3SiH$, diborane, 9-BBN, Alpine borane, $BH_3 \cdot Me_2S$, L-Selectride, alkyl borane reagents, or most preferably, $NaBH_4$. The reductive amination reaction yields a mixture of 1",2"-saturated and 1",2"-unsaturated products. The reaction proceeds at from 0° C. to 120° C. and is complete in from 15 min to 24 h. The preparation of compounds of formula 33c proceeded most preferrably via the intermediacy of compounds of formula 33b. Compounds of formula 33b could be deprotected to yield the primary 3"-amine using palladium-mediated deprotection reactions, including $PdCl_2(PPh_3)_2$, $Pd(OAc)_2$ $(PPh_3)_2$, $PdCl_2(PhCN)_2$, $Pd(OAc)_2$, $PdCl_2(P(o-tolyl)_3)_2$,

SCHEME XIII

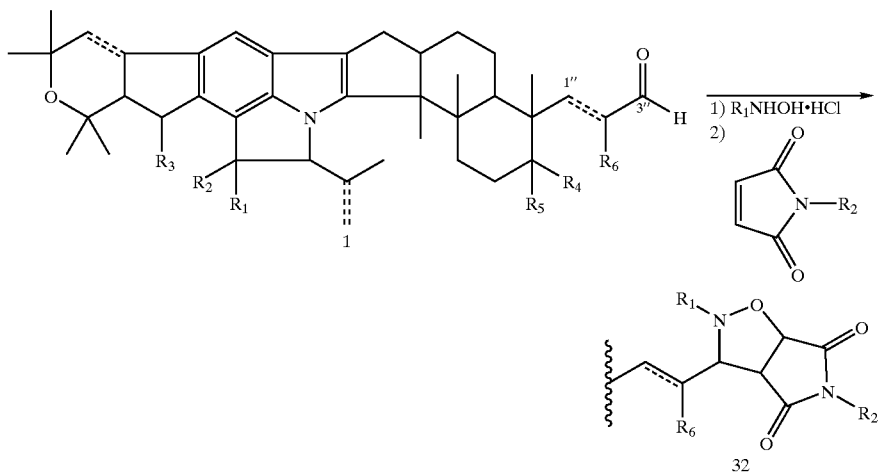

Compounds of formula 33a may be prepared as illustrated in Scheme XIV by reductive amination of compounds of $PdCl_2(DDPF)$, $Pd_2(dba)_3$, and the like, or most preferably $Pd(PPh_3)_4$. Hydride sources for successful deallylation reaction included, but are not restricted to Et$_3$SiH, Ph$_3$SiH, nBu$_3$SnH, Ph$_3$SnH, catechol borane and the like, or alternatively and most preferably dimethyl barbituric acid. Starting compound 1 may have its C7- and C24-hydroxyl groups protected with silyl protecting groups. The newly formed mono- and unsubstituted 3"-amines of compounds of formula 33a may be acylated with suitable acylating agents including, but not restricted to, acid chlorides, carboxylic acids, carbamoyl chlorides, isocyanates, chloroformates, sulfonyl chlorides and the like under conditions described previously to form 3"-amides, ureas, carbamates and sulfonamides, respectively.

diimidazole, triphosgene, para-nitrophenyl chloroformate, methyl chloroformate and the like or most preferably 1,1-carbonyl-diimidazole. Similarly, treatment of compounds of formula 33a where NR$^c$R$^d$ is an 1,2-aminoethanol derivative (e.g. NHCRRCRROH) with a cyclizing agent yields compounds of formula 35. In addition, treatment of compounds of formula 33a where where NR$^c$R$^d$ is a glycine derivative (e.g. NHCRRCO$_2$R) with an isocyanate yields compounds of formula 36. Alternatively, the isocyanate may be replaced

SCHEME XIV

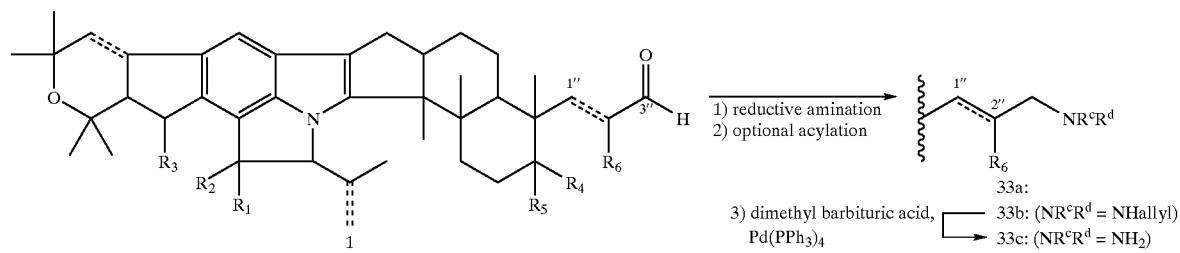

The compounds of formula 33a may be further elaborated as illustrated in Scheme XV to yield compounds of formula with a thiocyanate used to prepare the corresponding thiono derivatives of compounds of formula 36.

SCHEME XV

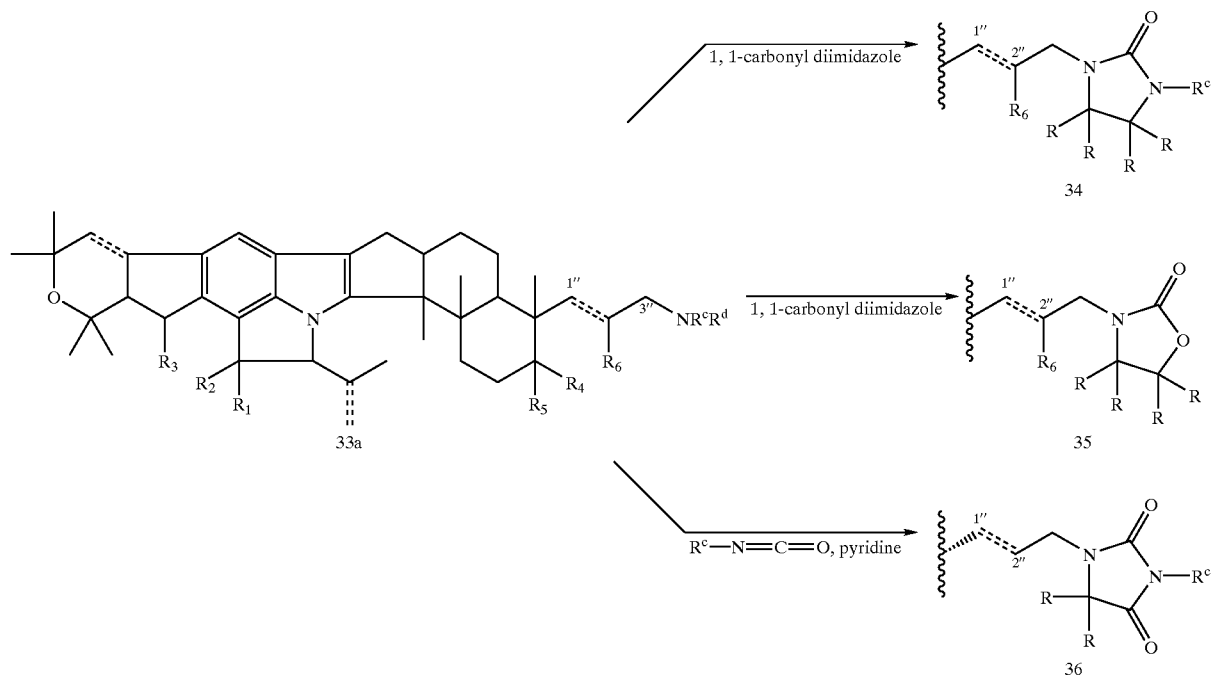

34, 35 and 36. Treatment of compounds of formula 33a where NR$^c$R$^d$ is an ethylenediamine derivative (e.g. NHCRRCRRNR$^c$) with a cyclizing agent yields compounds of formula 34. Suitable cyclization agents include but are not restricted to phosgene, thiophosgene, 1,1-thiocarbonyl- Compounds of formula 37 and 38 may be prepared as illustrated in Scheme XVI using olefination reactions described previously for compounds of formula 9 (Scheme V). The 2",3"-olefin of 37 and the 1",2"-olefin of 38 may be optionally reduced by hydrogenation using precious metal catalysts as described previously.

SCHEME XVI

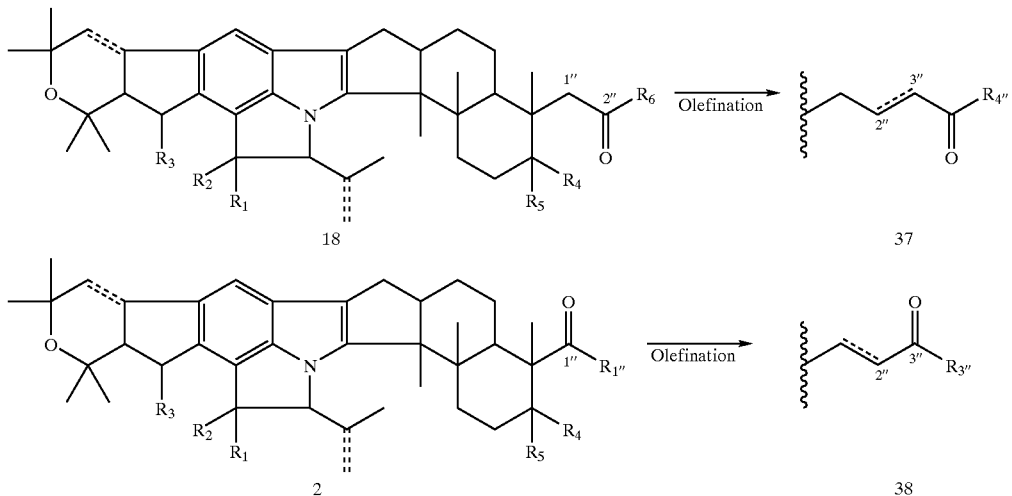

Compounds of formula 39a, 39b, 40a and 40b may be prepared as illustrated in Scheme XVII. Beginning with either compounds of formula 18 where $R_6$=H (2"-aldehyde) or compounds of formula 2 (1"-aldehyde), the C7 and C24 hydroxyls may be protected as described previously as the corresponding $R_3Si$ ethers. The 1"- or 2"-aldehydes may then be oxidized to the corresponding carboxylic acids as described for compounds of formula 5 (Scheme III) to yield the desired 2"- and 1"-carboxylic acids (39a and 40a, respectively where $R^b$=H). These carboxylic acids may be converted into the corresponding amides or esters as previously noted for compounds of formula 6 or 7.

SCHEME XVII

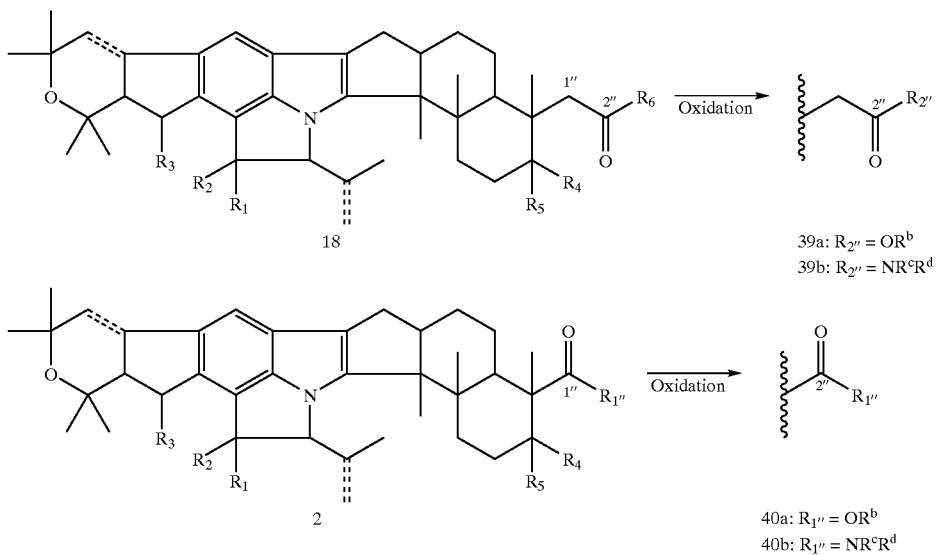

Compounds of formula 41 may be prepared as illustrated in Scheme XVIII beginning with compounds of formula 8. Treatment of the 3"-alcohol of 8 under Mitsunobu reaction conditions using a trisubstituted phosphine, a diazo reagent and an appropriate nucleophile will yield compounds of formula 41 where $R_3$" is halogen, azide, $OR^b$, $SR^b$ and the like. For a review of the Mitsunobu reaction see Hughes, D. L. *Organic Preparations and Procedures, Int.* 1996; 28, 127–164. Suitable phosphine reagents include, but are not restricted to, tri-n-butyl phosphine and most preferably triphenyl phosphine. Suitable diazo reagents include, but are not restricted to, dimethyl diazodicarboxylate, diisopropyl diazodicarboxylate, 1,1'-azobis(N,N-doimethylformamide) 1,1'-(azodicarbonyl)dipiperidine, azodicarboxylic dimorpholide or most preferably, diethyl diazodicarboxylate. Suitable nucleophile sources for this reaction include, but are not restricted to, methanol, 2,2,2-trifluoroethanol, acetic acid, benzoic acid, trimethylsilylazide, 2-mercaptopyridine, thiolacetic acid, phenol, 2-mercaptothiazole, carbon tetrachloride and the like. The reaction may be performed in solvents including, but not limited to, benzene, toluene, 1,2-dichloroethane, tetrahydrofuran, methanol, acetonitrile and the like or most preferably methylene chloride and the reactions are complete in from 15 min to 24 h at 0° C. to 120° C.

is an alkyl or aryl group. Following protection of the C7 and C24 hydroxyls of compound 16 with $R_3Si$ groups as described previously, the 4"-ketone is treated with a strong

SCHEME XVIII

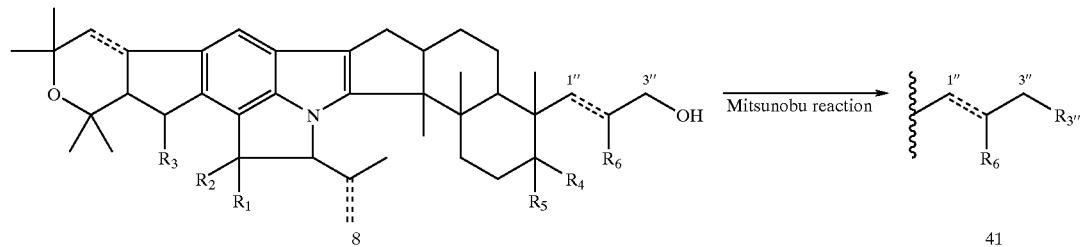

Compounds of formula 42 may be prepared as illustrated in Scheme XIV by the addition of an appropriate nucleophile to the 3"-aldehyde of compound 1. The C7 and C24 hydroxyls of compound 1 may be optionally protected with $R_3Si$ groups as previously described. The nucleophilic addition reaction may produce a mixture of stereoisomers at 3". Suitable nucleophiles include, but are not restricted to, Grignard reagents and organolithium, organocuprates organozinc reagents, organosodium reagents, organopotassium reagents and organocerium reagents and the like. These reagents include, but are not restricted to, MeMgBr, EtLi, PhMgCl, $(nPr)_2CuMgI$, $H_2C=CHMgBr$, 2-furfuryl lithium, $BrZnCH_2CO_2Me$, $NaCH_2C(O)Ph(4-Br)$ and the like. Suitable solvents, or mixtures of solvents for this reaction include, but are not restricted to, toluene, diethyl ether, hexanes, dioxane, 1,2-dimethoxyethane, DMSO, HMPA, DMPU and the like or most preferably, tetrahydrofuran. The reactions proceed at from −100° C. to 80° C. and are complete in from 5 min to 12 h. Replacement of compounds of formula 1 in the reaction illustrated in Scheme XIV with the 1"-aldehyde (compounds of formula 2) or the 2"-aldehyde (compounds of formula 18 where $R_6=H$) will yield the corresponding 1"- and 2"-hydroxy derivatives.

base to generate an intermediate enolate. Suitable bases for this reaction include, but are not limited to, lithium diisopropyl amine, potassium bis(trimethylsilyl)amide, sodium bis(trimethylsilyl)amide or most preferably lithium bis (trimethylsilyl)amide. Suitable electrophiles for this reaction include aldehydes, ketones or alkyl halides. Representative electrophiles include, but are not restricted to, formaldehyde, acetaldehyde, benzaldehyde, furfural, allyl bromide, bromoacetonitrile, alpha-bromo-tert-butyl acetate, benzyl bromide, and the like. Use of an alkyl halide (RX) in this reaction yields products of formula 43 where $R_3"=R$. Use of an aldehyde (RCHO) or a ketone (RC(O)R) as the electrophile in this reaction yields products of formula 43 where $R_3"=CH(OH)R$ or $C(OH)RR$, respectively. Suitable solvents, or mixtures of solvents for this reaction include, but are not restricted to, toluene, diethyl ether, hexanes, dioxane, 1,2-dimethoxyethane, DMSO, FMPA, DMPU and the like or most preferably, tetrahydrofuran. The reactions proceed at from −100° C. to 80° C. and are complete in from

SCHEME XIV

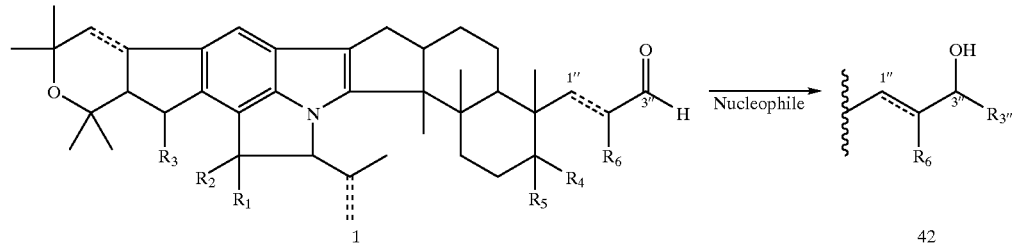

Compounds of formula 43 may be prepared as illustrated in Scheme XV from compounds of formula 16 where $R_4"$ a 5 min to 12 h. This reaction may yield a mixture of isomers at C3".

SCHEME XV

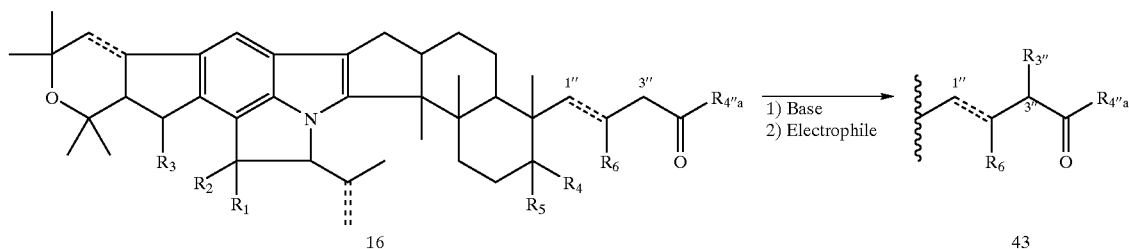

The instant compounds are potent endo- and ecto-antiparasitic agents, particularly against helminths, ectoparasites, insects, and acarids, infecting man, animals and plants, thus having utility in human and animal health, agriculture and pest control in household and commercial areas.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, fish, buffalo, camels, llamas, reindeer, laboratory animals, furbearing animals, zoo animals and exotic species and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Habronema, Druschia, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have activity against these parasites, and in addition are also active against Dirofilaria in dogs and cats, Nematospiroides, Syphacia, Aspiculuris in rodents, arthropod ectoparasites of animals and birds such as ticks, mites such as scabies lice, fleas, blowflies, and other biting insects in domesticated animals and poultry, such as Tenophalides, Ixodes, Psoroptes, and Hemotobia, in sheep Lucilia sp., biting insects and such migrating dipterous larvae as Hypoderma sp. in cattle, Gastrophilus in horses, and Cuterebra sp. in rodents and nuisance flies including blood feeding flies and filth flies.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., the housefly *Musca domestica* as well as fleas, house dust mites, termites and ants.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture. The compounds are also highly useful in treating acreage infested with fire ant nests. The compounds are scattered above the infested area in low levels in bait formulations which are brought back to the nest. In addition to a direct-but-slow onset toxic effect on the fire ants, the compound has a long-term effect on the nest by sterilizing the queen which effectively destroys the nest.

The compounds of this invention may be administered in formulations wherein the active compound is intimately admixed with one or more inert ingredients and optionally including one or more additional active ingredients. The compounds may be used in any composition known to those skilled in the art for administration to humans and animals, for application to plants and for premise and area application to control household pests in either a residential or commercial setting. For application to humans and animals to control internal and external parasites, oral formulations, in solid or liquid or parenteral liquid, implant or depot injection forms may be used. For topical application dip, spray, powder, dust, pour-on, spot-on, jetting fluid, shampoos, collar, tag or harness, may be used. For agricultural premise or area application, liquid spray, powders, dust, or bait forms may be used. In addition "feed-through" forms may be used to control nuisance flies that feed or breed in animal waste. The compounds are formulated, such as by encapsulation, to lease a residue of active agent in the animal waste which controls filth flies or other arthropod pests.

Accordingly, the present invention provides a method for the treatment or prevention of diseases caused by parasites which comprises administering to a host in need of such treatment or prevention an antiparasitic effective amount of a compound of Formula I. The parasites may be, for example, arthropod parasites such as ticks, lice, fleas, mites and other biting arthropods in domesticated animals and poultry. The parasites also include helminths such as those mentioned above.

Compounds of formula I are effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 500 mg per kg of animal body weight, such total dose being given at one time or in divided doses over a relatively short period of time such as 1–5 days. With the preferred compounds of the invention, excellent control of such parasites is obtained in animals by administering from about 0.025 to 100 mg per kg of body weight in a single dose. Repeat treatments are given as required to combat re-infections and are dependent upon the species of parasite and the husbandry techniques being employed. Repeat treatments may be given daily, weekly, biweekly, monthly, or longer for example up to six months, or any combination thereof, as required. The techniques for administering these materials to animals are known to those skilled in the veterinary field.

Compounds of formula I may be co-administered or used in combination with one or more other agents to the host. Co-administration or combination use includes administering all active ingredients in one formulation, for example a tablet, capsule, feed stuff, or liquid containing a compound of formula I and one or more said other agents; administering each ingredient in a separate formulation; and combinations thereof. When one or more of a compound of formula I or said other agent(s) is contained in a separate formulation, any order of administration as well as any interval between the administration of the active ingredients are within the meaning of co-administration or combination use.

Agents that may be co-administered or used in combination with compounds of formula I include any that are used in the treatment or prevention of human or animal diseases or conditions, or used in agricultural applications, or for. pest control. In a preferred embodiment, the co-administered agents are used in veterinary medicine, particularly those used in domesticated animals such as dogs and cats or other companion animals. Examples of other agents that may be co-administered with compounds of formula I are provided below. It is to be understood that the specific agents enumerated are illustrative only, and are not meant to be restrictive in any manner.

Accordingly, compounds of the present invention may be co-administered or used in combination with anthelmintic agents. These anthelmintic agents are meant to include, but not be restricted to, compounds selected from the avermectin and milbemycin class of compounds such as ivermectin, avermectin, abamectin, emamectin, eprinamectin, doramectin, milbemycin derivatives described in EPO 357460, EPO 444964 and EPO 594291, moxidectin, Interceptor™ and nemadectin. Additional anthelmintic agents include the benzimidazoles such as thiabendazole, cambendazole, parbendazole, oxibendazole, mebendazole, flubendazole, fenbendazole, oxfendazole, albendazole, cyclobendazole, febantel, thiophanate and the like. Additional anthelmintic agents include imidazothiazoles and tetrahydropyrimidines such as tetramisole-levamisole, butamisole, pyrantel, pamoate, oxantel or morantel.

Compounds of this invention may be co-administered or used in combination with fipronil (FRONTLINE™); or with an insect growth regulator with molt inhibiting activity such as lufenuron (PROGRAM™) and the like; or with ecdysone agonists such as tebufenozide and the like, which induces premature molt and causes feeding to cease; or with imidacloprid (ADVANTAGE™).

Compounds of this invention may be co-administered or used in combination with avermectin or milbemycin or doramectin derivatives including selamectin (Revolution™) such as those described in U.S. Pat. 5,015,630, WO 94/15944, WO95/22552.

Compounds of this invention may be co-administered or used in combination with cyclic depsipeptides that exhibit anthelmintic efficacy such as those described in WO96/11945, WO93/19053, WO 93/25543, EP 626375, EP 382173, WO 94/19334, EP 382173 and EP 503538.

Compounds of this invention may be used in combination or be co-administered with derivatives and analogs of the general class of dioxomorpholine antiparasitic and anthelmintic agents as illustrated by WO 9615121; or with pyrethroids or organophosphates or insecticidal carbamates, such as those described in "Chemotherapy of Parasitic Diseases", Campbell, W. C. and Rew, R. S, Eds., 1986; or with derivatives and analogs of the general class of paraherquamide and macfortine anthelmintic agents.

The co-administered compounds are given via routes, and in doses, that are customarily used for those compounds.

Compounds of formula I may be administered orally in a unit dosage form such as a capsule, bolus or tablet including chewable tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets or liquid which may then be added to the finished feed or optionally fed separately. Alternatively, feed based individual dosage forms may be used such as a chewable treat. Alternatively, the antiparasitic compounds of this invention may be administered to animals parenterally, for example, by intraruminal, intramuscular, intravascular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, propylene glycol, and aqueous parenteral formulations are also used. The active compound or compounds are dissolved or suspended in the parenteral formulation for administration; such formulations generally contain from 0.0005 to 5% by weight of the active compound.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 50% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 10% in the feed in order to achieve the desired anti-parasitic result.

In using the compounds of this invention, the individual compounds may be prepared and used in that form. Alternatively, mixtures of the individual compounds may be used, or they may be combined with other active compounds not related to the compounds of this invention.

Also included in the present invention are pharmaceutical compositions comprising a compound of formula I and a pharmaceutically acceptable carrier. The pharmaceutical compositions of the present invention may further comprise a second active ingredient such as those described above for co-administration. Preferred second ingredient is selected from an anthelmintic agent, fipronil, imidocloprid, an insect growth regulator, or a ecdysone agonist. Said second ingredient is preferably selected from the group consisting of: ivermectin, avermectin 5-oxime, abamectin, emamectin, eprinamectin, doramectin, doramectin monosaccharide 5-oximes, fulladectin, milbemycin, milbemycin 5-oxime, moxidectin, Interceptor™, nemadectin, imidacloprid, fipronil, lufenuron, tthiabendazole, cambendazole, parbendazole, oxibendazole, mebendazole, flubendazole, fenbendazole, oxfendazole, albendazole, cyclobendazole, febantel, thiophanate, tetramisole-levamisole, butamisole, pyrantel, pamoate, oxantel and morantel.

PREPARATION OF INTERMEDIATES

Intermediate I

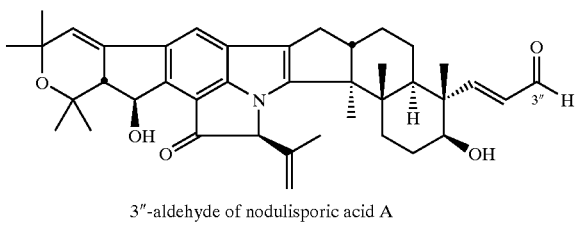

3″-aldehyde of nodulisporic acid A (a) Synthesis from Nodulisporic Acid A

To $KMnO_4$ (3 g) at 25° C. was added water (5 mL). The $KMnO_4$ solution was cooled to 0° C. and $Al_2O_3$ (weakly acidic, 10.8 g) was added and stirred for 5 min until thoroughly mixed. A solution of nodulisporic acid A (3 g) in $CH_2Cl_2$ (300 mL) was added dropwise via an addition funnel over 20 min. The solution was aged for an additional 20 min at 0° C. then at 25° C. for 90 min. The solution was filtered through a 3 inch pad of Celite using $CH_2Cl_2$ as eluant followed by EtOAc. The solvents were removed under reduced pressure at ambient temperature to yield pure title compound (2.234 g, 82%) without any additional purification.

(b) Synthesis from t-Butyl Nodulisporamide

To N-tert-butyl nodulisporamide A (50 mg) in $CH_2Cl_2$ (2 mL) at 25° C. was added N-methylmorpholine N-oxide (50 mg) followed by 0.024 M $OSO_4$ in water (0.31 mL). After aging the solution for 16 hr, TLC showed the presence of the desired compound and the R,R- and S,S-3″,4″-diols of N-tert-butyl nodulisporamide A. Intermediate I (10.5 mg) and the diols (36 mg) were isolated in pure form by PVLC on silica gel using 2:1 EtOAc:hexanes as eluant. The R,R- and S,S-diols were combined. To a mixture of diols (10 mg) in acetone (0.9 mL) at 25° C. was added $NaIO_4$ (25 mg) and the solution was allowed to age for 12 h. The solution was poured into saturated aqueous $NaHCO_3$, extracted with EtOAc and dried ($Na_2SO_4$). Pure Intermediate I (7 mg) was obtained following PTLC on silica gel using 1/1 hexanes/EtOAc as eluant.

Intermediate II

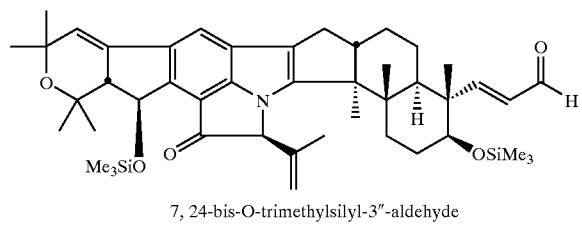

7, 24-bis-O-trimethylsilyl-3″-aldehyde

To Intermediate I (560 mg) in acetonitrile (10 mL) at 25° C. was added $(Me_3Si)_2NH$ (1.8 mL) and the the solution was aged for 12 h. Additional $(Me_3Si)_2NH$ (1.5 mL) and acetonitrile (3 mL) were then added. After 3 h, the solvent was removed under reduced pressure and the residue dried in vacuo for 1 h to yield pure title compound (870 mg, 100%) which required no purification. The product was characterized by proton NMR.

Intermediate III

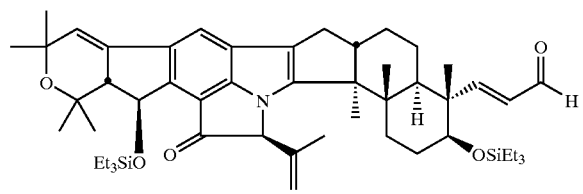

7, 24-bis-O-triethylsilyl-3″-aldehyde

To Intermediate I (750 mg) in pyridine/DMF (30 mL, 1/1) at room temperature was added $Et_3SiOSO_2CF_3$ (3.2 g) and aged for 20 min. The solution was diluted with ethyl acetate, washed with saturated $CuSO_4(aq)$ (4×), water (1×), brine (1×), and dried ($Na_2SO_4$). The solution was filtered, concentrated under reduced pressure and pure product was obtained following flash chromatography on silica gel using 7/93 acetone/hexanes as eluant. The title compound thus obtained was haracterized by $^1H$ NMR.

Intermediate IV

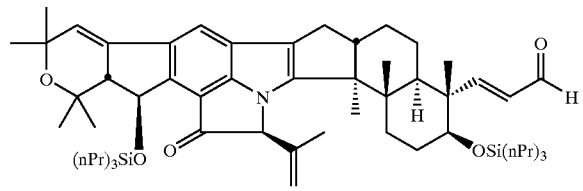

7, 24-bis-O-tri-n-propylsilyl-3″-aldehyde

To Intermediate I (420 mg) and imidazole (540 mg) in $CH_2Cl_2$ (15 mL) at 0° C. was added $(nPr)_3SiCl$ (1 mL) dropwise. After stirring for 30 min, the solution was warmed to room temperature for an additional 30 min and then quenched with ice-water. The organic phase was separated and washed with water, dried (NaSO₄), filtered and concentrated to give the pure product as a foam (620 mg). The product thus obtained was characterized by proton NMR.

Intermediates Va and Vb

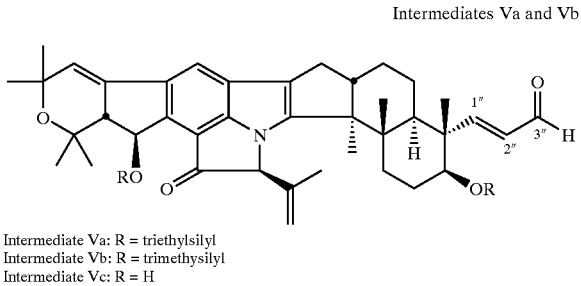

Intermediate Va: R = triethylsilyl
Intermediate Vb: R = trimethysilyl
Intermediate Vc: R = H Preparation of Intermediate Va Method A To Intermediate III (1 g) in tBuOH (25 mL) at 25° C. was added 2-methyl-2-butene (6 mL) and stirred for 5 min. A solution of NaOCl₂ (954 mg) and NaH₂PO₄·2H₂O (1.28 g) in water (10 mL) was then added. After 4 h, the solution was poured into saturated NH₄Cl(aq), extracted with CH₂Cl₂ (3×) and dried (Na₂SO₄). The solution was filtered and concentrated to dryness under reduced pressure. Pure title compound (725 mg) was obtained following flash chromatography on silica gel using gradient elution (5% to 25% EtOAc in hexanes).

Method B

A solution of KMnO₄ (1.3 g) in acetone (64 mL) and pH 7 phosphate buffer (21 mL) was prepared. To Intermediate III (3.63 g) in acetone (64 mL) was added the KMnO₄/buffer solution (~20 mL) and the solution was aged for 30 min. Additional KMnO₄ solution (~20 mL) was added every 30 min for 2 h. The solution was then cooled to 0° C. and 1M Na₂SO₃ was added until all of the KMnO₄ was reacted. The mixture was filtered and washed with 15/85 MeOH/acetone (2×). The filtrate was concentrated under reduced pressure to dryness and redissolved in water. The aqueous solution was extracted with 3/7 iPrOH/CHCl₃ (3×) and the organic layers were dried (Na₂SO₄). The solids were removed by filtration and the solution was evaporated to drynesss under reduced pressure. Pure title product (1.29 g) along with recovered starting aldehyde (~1.3 g) was obtained following flash chromatography on silica gel using 2/8 EtOAc/hexanes as eluant.

Preparation of Intermediate Vb

Following the procedure described for Intermediate Va and using Intermediate II, Intermediate Vb was prepared.

Intermediates VIa and VIb

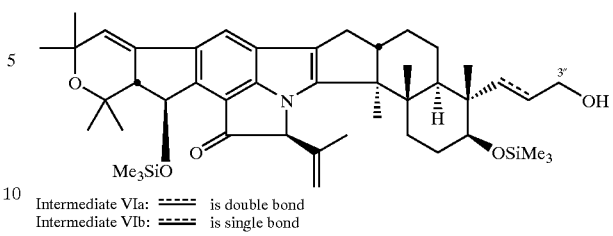

Intermediate VIa: ===== is double bond
Intermediate VIb: ===== is single bond

Method A

To Intermediate II (821 mg) in tetrahydrofuran (THF, 8 mL) at −78° C. was added L-Selectride® (Adrich, 1.07 mL, 1 M solution in THF) dropwise over 5 min. After 20 min, the solution was quenched by addition of saturated NH₄Cl(aq), extracted with CH₂Cl₂, washed with brine and dried (Na₂SO₄). The solution was filtered, concentrated under reduced pressure and purifed by flash chromatography on silica gel using 15/85 EtOAc/hexanes as eluant. The pure Intermediate VIa (571 mg) thus obtained was characterized by ¹H NMR.

Method B

To Intermediate II (1.0 g) in EtOAc (50 mL) at room temperature was added 10% Pd/C and a balloon atmosphere of hydrogen was established. After 5.5 h, the solution was filtered through Celite using EtOAc as eluant. The solution was concentrated under reduced pressure and purifed by MPLC chromatography on silica gel using 4/6 EtOAc/hexanes as eluant. The pure Intermediate VIa (726 mg, mobile product) and pure Intermediate VIb (70 mg, polar product) thus obtained were characterized by ¹H NMR.

Intermediate VII

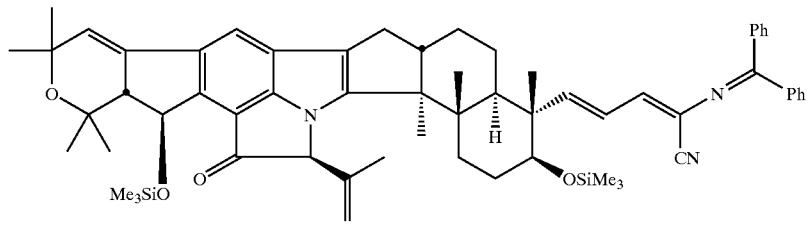

To (N-diphenylmethylene)amino acetonitrile (75 mg) in THF (0.5 mL) at −78° C. was added LiN(SiMe₃)₂ (340 μL, 1.0 M solution). The yellow solution was stirred at −78° C. for 5 min, placed in a 0° C. ice bath for 5 min and then recooled to −78° C. for 15 min. A solution of Intermediate II (65 mg in 0.8 mL THF) was added at −78° C. After 25 min, MeSO₂Cl (60 μL) was added. After 10 min, triethylamine (36 μL) was added and the reaction warmed first to 0° C. for 20 min and then room temperature of 2 h. The solution was rapidly filtered without workup through a 1 inch pad of silica gel using CH₂Cl₂ followed by 15/85 EtOAc/hexanes as eluant. The solution was concentrated to dryness under reduced pressure and used in the next step without any further manipulation or characterization.

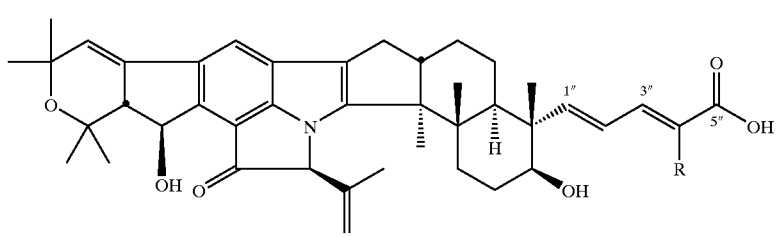

Intermediate VIII

VIIIa: R = Et
VIIIb: R = nPr
VIIIc: R = nBu

Step A.

To Intermediate I (128 mg) in CH$_2$Cl$_2$ (10 mL) at 25° C. was added Ph$_3$P=C(Et)CO$_2$CH$_2$CH=CH$_2$ (320 mg). The solution was aged for 2 days and then additional Ph$_3$P=C(Et)CO$_2$CH$_2$CH=CH$_2$ (320 mg) was added. After one additional hour, the solution was purified without workup by flash chromatography on silica gel using 6/4 EtOAc/hexanes as eluant to yield pure allyl ester of Intermediate VIIIb (124 mg, 84%). The purified allyl ester of Intermediate VIIIa was characterized by proton NMR and mass spectrometry [m/z: 734.1. (M$^+$+1)].

Step B.

To the 5"-allyl ester of Step A (160 mg) in 1/3 THF/CH$_2$Cl$_2$ (8 mL) at 25° C. was added (Ph$_3$P)$_4$Pd (13 mg) and morpholine (160 mg). The solution was aged for 6 h and the solution was purified without workup by flash chromatography on silica gel using 1/9 MeOH/CH$_2$Cl$_2$ as eluant to yield pure Intermediate VIIIa (112 mg, 74%). The purified Intermediate VIIIa was characterized by proton NMR and mass spectrometry [m/z: 693.4 (M$^+$+1)].

Intermediates VIIIb and VIIIc were similarly prepared following the procedure for Intermediate VIIIa and using Ph$_3$P=C(n-Pr)CO$_2$CH$_2$CH=CH$_2$ and Ph$_3$P=C(n-Bu)CO$_2$CH$_2$CH=CH$_2$, respectively.

The following examples are provided to illustrate the invention and are not to be construed as limiting the scope of the invention in any manner.

EXAMPLE 1

Step A.

To a solution of Intermediate I (70 mg) in CH$_2$Cl$_2$ (2 mL) at room temperature was added pyridine (0.2 mL) and N-methylhydoxylamine hydrochloride (30 mg). After aging for 1 h, the solution was diluted with CH$_2$Cl$_2$ (10 mL), and washed with 10% aqueous citric acid and water. The organic phase was dried (Na$_2$SO$_4$) and concentrated in vacuo to give the desired corresponding nitronate (66 mg). The product thus obtained was characterized by proton NMR and mass-spectral analysis [m/z: 826.3 (M$^+$+1)].

Step B.

A mixture of the 3"-nitronate from Step A (20 mg) and N-phenyl-maleimide (20 mg) was dissolved in dry CH$_3$CN (0.5 mL) and aged at room temperature for 18 h. The crude reaction mixture was then purified without workup by PTLC on silica gel (Analtech plates, 1×1000 μm plate) using EtOAc/hexane (1/1) as eluant. The pure product (14 mg) thus obtained was characterized by proton NMR and mass-spectral analysis [m/z: 826.3 (M$^+$+1)].

Examples 1a–1o

Following the general procedure described in Example 1 using the appropriate dipolarophiles, the following compounds were prepared:

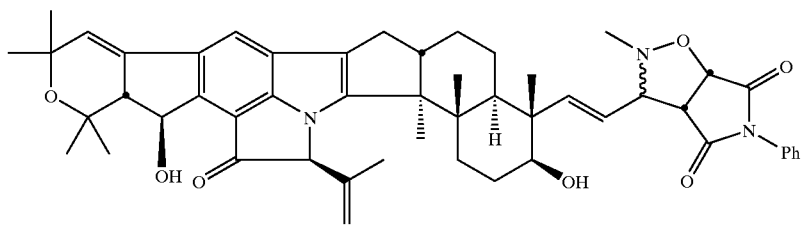

TABLE 1

| Ex. | Ring Group | 3"-Isomer | Mass Spec |
|---|---|---|---|
| 1a | | Is. A & B | |
| 1b | | Is. A | 854.3(M⁺ + 1) |
| 1c | | Is. B | |
| 1d | | Is. A & B | 855.2(M⁺ + 1) |
| 1e | | Is. A & B | 764.6(M⁺ + 1) |
| 1f | | Is. A & B | 778.6(M⁺ + 1) |

TABLE 1-continued
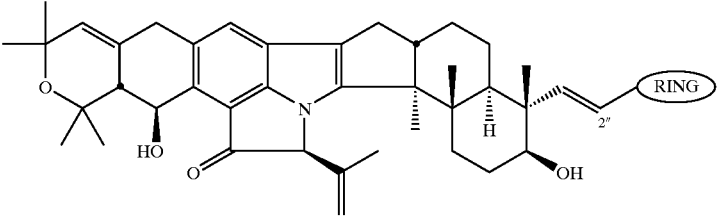
| Ex. | Ring Group | 3"-Isomer | Mass Spec |
|---|---|---|---|
| 1g | 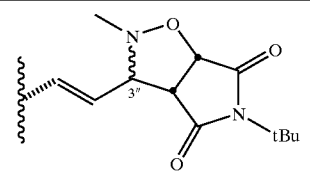 | Is. A & B | 806.2(M⁺ + 1) |
| 1h | 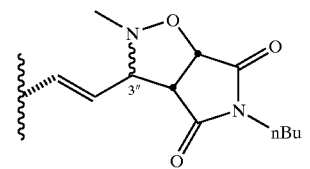 | Is. A & B | 806.3(M⁺ + 1) |
| 1i | 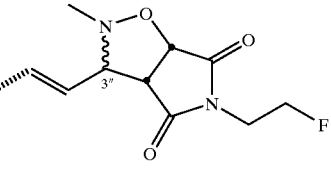 | Is. A & B | 796.7(M⁺ + 1) |
| 1j | 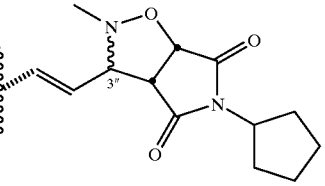 | Is. A & B | 818.6(M⁺ + 1) |
| 1k | 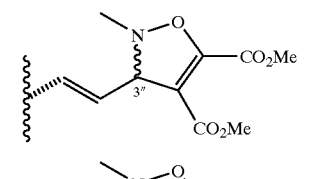 | Is. A & B | 795.3(M⁺ + 1) |
| 1l | 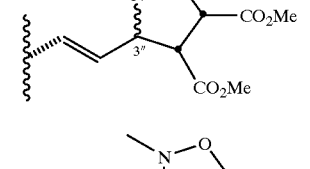 | Is. A & B | |
| 1m | 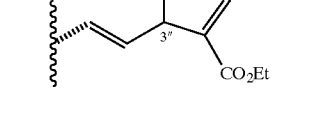 | Is. A | 751.2(M⁺ + 1) |
| 1n | 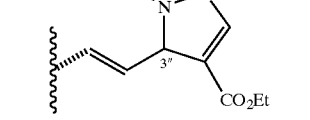 | Is. B | 751.4(M⁺ + 1) |

EXAMPLE 2

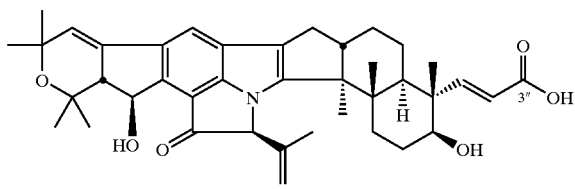

To a mixture of Intermediate I (140 mg), t-BuOH (3 mL), $NaH_2PO_4$ (90 mg), water (0.5 mL) and 2-methylbutene (1 mL) at rt, was added a solution of sodium chlorite (80 mg) in water (1 mL) dropwise. After aging for 4 h, the reaction mixture was diluted with water (10 mL), chilled in an ice-bath and acidified with 10% aqueous citric acid. The mixture was extracted with ethyl acetate, dried ($Na_2SO_4$), filtered and concentrated under reduced pressure. Pure title compound (120 mg) was obtained following PTLC on silica gel (Analtech plates, 2×1000 μm plates) using EtOAc/hexane (2/1) as eluant. The product thus obtained was characterized by proton NMR and mass-spectral analysis [m/z: 640.5 (M−75)].

EXAMPLE 3

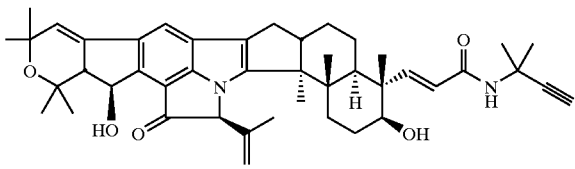

To compound of Example 2 (10 mg), HOBT (5 mg), 1,1-dimethyl-propargylamine (0.025 mL) and BOP (15 mg) in $CH_2Cl_2$ (1 mL) at 0° C. was added triethylamine (0.025 mL). The solution was aged for 18 h at room temperature and then diluted with ethyl acetate (10 mL), washed with saturated $NaHCO_3$, 10% citric acid and water. The crude product isolated from the organic phase was purified on by PTLC on silica gel (Analtech plates, 1×1000 μm) using EtOAc/hexane (1/1) as eluant to give the desired product. The pure title compound (7.5 mg) thus obtained was characterized by proton NMR and mass-spectral analysis [m/z: 705.5 ($M^+$+1)].

EXAMPLE 4

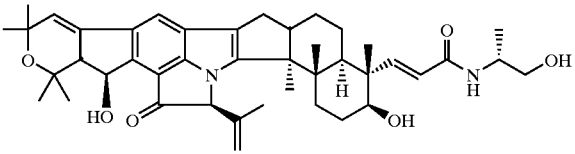

To Intermediate Vb (70 mg) in $CH_2Cl_2$ (5 mL) at room temperature was added sequentially HOBT (24 mg), (R)-2-amino-1-propanol (70 μL) and BOP (44 mg) and the solution was aged for 45 min. The volatiles were removed under reduced pressure and pure product (88 mg) was obtained following PTLC on silica gel (1×1500 μm plate) using 3/7 acetone/hexanes as eluant. The 7,24-bis-O-TMS protected title compound thus obtained was characterized by $^1H$ NMR.

To the 7,24-bis-O-TMS protected title compound (25 mg) in EtOH (3 mL) at room temperature was added PPTS (17 mg) and the solution was aged for 2 h. The volatiles were removed under reduced pressure and pure product (18.3 mg) was obtained following PTLC on silica gel (1×1000 μm plate) using 1/9/90 $NH_4OH/MeOH/CHCl_3$ as eluant. The title product thus obtained was characterized by $^1H$ NMR and MS [m/z: 697.0 ($M^+$+1)].

EXAMPLE 5

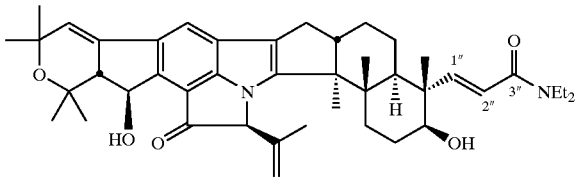

To Intermediate Va (150 mg) in $CH_2Cl_2$ (5 mL) at 0° C. was added sequentially diethylamine (90 μL), BOP (84 mg), HOBT (47 mg). The solution was slowly warmed to room temperature over 2.5 h. The solution was poured into saturated $NaHCO_3$(aq), extracted with $CH_2Cl_2$ and dried ($Na_2SO_4$). The solution was filtered and concentrated under reduced pressure and purifed by MPLC on silica gel using EtOAc/hexanes as eluant. The pure 7,24-bis-O-triethylsilyl protected title compound thus obtained (155 mg) was characterized by $^1H$ NMR.

The title compound was obtained following removal of the triethylsilyl protecting group using the general procedure described in Example 4 for the removal of trimethylsilyl protecting group and the product thus obtained was characterized by proton NMR.

EXAMPLES 5A–5VV

Following the general procedures described in Examples 3–5 and using the appropriate amines, the following 3″-amides were prepared:

TABLE 2

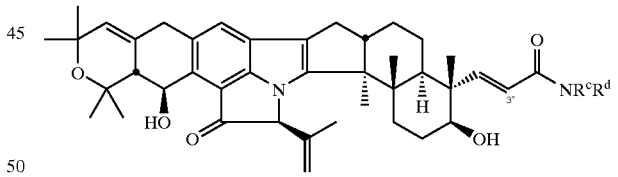

| Ex | $R^c$ Group | $R^d$ Group | Mass Spec |
|---|---|---|---|
| 5a | 1-($CH_2OH$)(c-$C_5H_8$) | H | 737.0($M^+$ + 1) |
| 5b | 2-(HO)(c-$C_6H_{10}$) | H | 737.0($M^+$ + 1) |
| 5c | c-$C_3H_5$ | H | 679.3($M^+$ + 1) |
| 5d | Me | H | 653.7($M^+$ + 1) |
| 5e | Me | Me | 667.4($M^+$ + 1) |
| 5f | Et | H | 667.3($M^+$ + 1) |
| 5g | Et | Me | 681.7($M^+$ + 1) |
| 5h | Et | iPr | 709.5($M^+$ + 1) |
| 5i | iPr | H | 681.3($M^+$ + 1) |
| 5j | nPr | H | 681.5($M^+$ + 1) |
| 5k | tBu | H | 694.8($M^+$ + 1) |
| 5l | allyl | Me | 693.4($M^+$ + 1) |
| 5m | $C(Me)_2$(2-pyridyl) | H | 758.5($M^+$ + 1) |
| 5n | $C(Me)_2$(3-pyridyl) | H | 758.5($M^+$ + 1) |
| 5o | $C(Me)_2$(4-pyridyl) | H | 758.4($M^+$ + 1) |
| 5p | $C(Me)_2CH_2OH$ | H | 711.0($M^+$ + 1) |
| 5q | $C(Me)_2CO_2Me$ | H | 739.3($M^+$ + 1) |

TABLE 2-continued

| Ex | R$^c$ Group | R$^d$ Group | Mass Spec |
|---|---|---|---|
| 5r | CH(CH(Me)OH)CO$_2$CH$_2$CH=CH$_2$ | H | |
| 5s | CH$_2$CF$_3$ | H | 645.1(M − 75) |
| 5t | CH(CH$_2$F)$_2$ | H | 717.3(M$^+$ + 1) |
| 5u | CH$_2$CH$_2$F | H | 609.3(M − 75) |
| 5v | CH(CH$_2$OH)C(O)NHC(Me)=CH$_2$ | H | |
| 5w | CH$_2$CH(OH)Ph | H | 759.0(M$^+$ + 1) |
| 5x | CH$_2$CH$_2$CH(OMe)$_2$ | H | 741.0(M$^+$ + 1) |
| 5y | CH$_2$CH$_2$CH$_2$OH | H | 697.0(M$^+$ + 1) |
| 5z | CH$_2$CH$_2$CH$_2$OMe | H | 711.3(M$^+$ + 1) |
| 5aa | CH$_2$CH$_2$OH | H | 683.0(M$^+$ + 1) |
| 5bb | CH$_2$Ph | Me | 744.6(M$^+$ + 1) |
| 5cc | L-CH(CH$_2$OH)CO$_2$CH$_2$Ph | H | 817.0(M$^+$ + 1) |
| 5dd | L-CH(CH$_2$OH)CO$_2$Et | H | 755.0(M$^+$ + 1) |
| 5ee | L-CH(CH$_2$OH)CO$_2$Me | H | 741.0(M$^+$ + 1) |
| 5ff | L-CH(CH$_2$OH)C(O)NH—Me | H | 740.0(M$^+$ + 1) |
| 5gg | L-CH(CH$_2$OH)C(O)NH—tBu | H | 782.0(M$^+$ + 1) |
| 5hh | D-CH(CH$_2$OH)C(O)NH—Et | H | 754.0(M$^+$ + 1) |
| 5ii | L-CH(CH$_2$OH)C(O)NH—Et | H | 754.0(M$^+$ + 1) |
| 5jj | D-CH(CH$_2$OH)C(O)N(Me)$_2$ | H | 754.0(M$^+$ + 1) |
| 5kk | L-CH(CH$_2$OH)C(O)N(Me)$_2$ | H | 754.0(M$^+$ + 1) |
| 5ll | D-CH(CH$_2$Ph)CH$_2$OH | H | 773.0(M$^+$ + 1) |
| 5mm | L-CH(CH$_2$Ph)CH$_2$OH | H | 773.0(M$^+$ + 1) |
| 5nn | D-CH(iPr)CH$_2$OH | H | 725.0(M$^+$ + 1) |
| 5oo | L-CH(iPr)CH$_2$OH | H | 725.0(M$^+$ + 1) |
| 5pp | D-CH(Me)CH$_2$OH | H | 697.0(M$^+$ + 1) |
| 5qq | L-CH(Me)CH$_2$OH | H | 697.0(M$^+$ + 1) |
| 5rr | D-CH(Ph)CH$_2$OH | H | 759.0(M$^+$ + 1) |
| 5ss | L-CH(Ph)CH$_2$OH | H | 759.0(M$^+$ + 1) |
| 5tt | D-CH$_2$CH(OH)Me | H | 697.0(M$^+$ + 1) |
| 5uu | L-CH$_2$CH(OH)Me | H | 697.0(M$^+$ + 1) |
| 5vv | | | 775.4(M$^+$ + 1) |

EXAMPLES 6a AND 6b

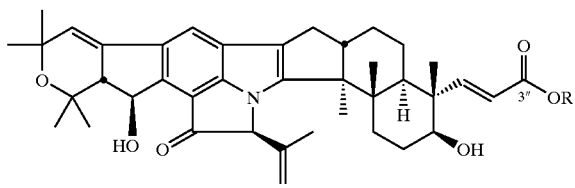

Example 6a: R = ethyl
Example 6b: R = methyl

Preparation of Compound of Example 6a

A mixture of Intermediate I (20 mg), AcOH (0.01 mL), NaCN (8 mg) and MnO$_2$ (300 mg) in EtOH (1.5 mL) was stirred at room temperature for 18 h. The solution was filtered through Celite, the filtrate was diluted with ethyl acetate, washed with water, dried (Na$_2$SO$_4$) and concentrated. The crude product thus obtained was purified by PTLC on silicagel (Analtech plates, 1×1000 μm) using EtOAc/hexane (1/1) as eluant. The pure title compound (10 mg) thus obtained was characterized by proton NMR and mass-spectral analysis [m/z: 668.4 (M$^+$+1)].

Preparation of Compound of Example 6b

Following the general procedure described in Example 6a and using methanol instead of ethanol, the 3"-methyl ester was obtained and characterized by $^1$H NMR and MS [m/z: 654.5 (M$^+$+1)].

EXAMPLE 7

To Intermediate I (623 mg) in methanol (40 mL) at 0° C. was added allyl amine (675 μL) followed by glacial acetic acid (291 μL). To this solution was added NaBH$_4$ (954 mg) in portions. The solution was stirred at 0° C. for 10 min, then warmed to 25° C. and aged for 2 h. The solution was poured into saturated brine, extracted with EtOAc and the organic layers were dried (Na$_2$SO$_4$). The organic layer was filtered and concentrated under reduced pressure. Pure title compound (551 mg) was obtained following PTLC purification (10×1000 μm silica gel plates) using 1/9 MeOH/CHCl$_3$ as eluant. The pure product was characterized by $^1$H NMR and mass spectrometry [m/z: 665.3 (M$^+$+1)].

EXAMPLE 8

Intermediate 8a: ===== is double bond
Intermediate 8b: ===== is single bond

To Intermediate I (400 mg) in methanol (3.6 mL) at 0° C. was added tert-butyl amine (545 μL) followed by glacial acetic acid (182 μL). After 5 min, a thick yellow slurry formed and the solution was warmed to rt. After 10 min, the solution became less viscous and was recooled to 0° C. To the cooled solution was added NaBH$_3$CN (182 mg) in one portion. The solution was stirred at 0° C. for 10 min, then warmed to 25° C. and aged for 1 h. The now homogenous solution was poured into saturated brine, extracted with EtOAc and the organic layers were dried (Na$_2$SO$_4$). The solution was filtered and concentrated under reduced pressure. Pure 3"-tert-butyl amine (Example 8a, 290 mg, polar product) and pure 1",2"-dihydro-3"-tert-butyl amine (Example 8b, 23 mg, mobile product) were obtained following PTLC on silica gel (10×1000 μm plates) using MeOH/CH$_2$Cl$_2$ (1/9, 2 developments) as eluant. The pure products were characterized by $^1$H NMR and mass spectrometry [m/z: 681.4 (M$^+$+1) for Example 8a and 683.3 (M$^+$+1) for Example 8b].

EXAMPLES 8c–8vv

Following the general description of Example 8 and using an appropriate amine, the following amine derivatives were prepared:

TABLE 3

| Ex | NR$^c$R$^d$ Group | 1"–2" | Mass Spec |
|---|---|---|---|
| 8c | NHMe | double | 639.3(M$^+$ + 1) |
| 8d | NHMe | single | |
| 8e | NHEt | double | 653.9(M$^+$ + 1) |
| 8f | NH(nPr) | double | 667.3(M$^+$ + 1) |
| 8g | NH(nPr) | single | |
| 8h | NH(n-hexyl) | double | 696.0(M$^+$ + 1) |
| 8i | NH(c-C$_3$H$_5$) | double | 665.4(M$^+$ + 1) |
| 8j | N(Me)Et | double | 667.7(M$^+$ + 1) |
| 8k | NH-[(1-CO$_2$Me)-c-pentyl] | double | 751.6(M$^+$ + 1) |
| 8l | NH-[(1-CO$_2$Me)-c-propyl] | double | 723.8(M$^+$ + 1) |
| 8m | NHPh(2-CO$_2$Et) | double | 759.7(M$^+$ + 1) |
| 8n | NHPh(2-OH) | double | 739.1(M + Na) |
| 8o | NHPh(2-OH, 4-Me) | double | 731.3(M$^+$ + 1) |
| 8p | NHPh(4-OMe) | double | 731.7(M$^+$ + 1) |
| 8q | NHCH$_2$CH$_2$OH | double | 670.2(M$^+$ + 1) |
| 8r | NHCH$_2$CH$_2$OCO$_2$-iBu | double | |
| 8s | NHCH$_2$Ph(3-OCF$_3$) | double | 779.3(M$^+$ + 1) |
| 8t | NHCH$_2$Ph(3-OCF$_3$) | single | |
| 8u | NHCH$_2$Ph(4-OCF$_3$) | double | |
| 8v | NHCH$_2$Ph(4-OMe) | double | |
| 8w | NHCH$_2$(2-pyridyl) | double | 716.4(M$^+$ + 1) |
| 8x | NHCH$_2$(4-pyridyl) | double | 716.4(M$^+$ + 1) |
| 8y | NHCH$_2$CH$_2$(2-pyridyl) | double | 730.6(M$^+$ + 1) |
| 8z | NHCH$_2$CH$_2$(2-(N—Me)pyrrolyl) | double | 732.5(M$^+$ + 1) |
| 8aa | NHCH$_2$(2-pyrrolidinyl) | double | 709.4(M$^+$ + 1) |
| 8bb | NHCH$_2$(2-(N—Et)pyrrolidinyl) | double | 736.8(M$^+$ + 1) |
| 8cc | NHCH$_2$CH$_2$(1-(N-piperidinyl)) | double | 730.6(M$^+$ + 1) |
| 8dd | NHCH$_2$CH$_2$(1-piperidyl) | double | |
| 8ee | NH(CH$_2$)$_3$(1-morpholinyl) | double | |
| 8ff | NHCH$_2$CH$_2$NH—Me | double | 606.4(M – 75) |
| 8gg | NHCH$_2$CF$_2$CF$_2$CF$_3$ | double | 807.8(M$^+$ + 1) |
| 8hh | N(CH$_2$CF$_3$)$_2$ | double | |
| 8ii | NHCH(Me)CH(OH)Ph | single | |
| 8jj | NHCH(Ph)CH$_2$OH | single | |
| 8kk | NHCH(CH$_2$Ph)CO$_2$Me | single | |
| 8ll | NHCH(s-Bu)CO$_2$Me | double | 717.3(M$^+$ + 1) |
| 8mm | NHC(Me)$_2$CO$_2$Me | double | |
| 8nn | NHC(Me)$_2$CO$_2$Me | single | |
| 8oo | NH—(D)—CH(Me)CO$_2$Me | double | 711.6(M$^+$ + 1) |
| 8pp | NHC(Me)$_2$CN | double | 890.7(M$^+$ + 1) |
| 8qq | NHCH$_2$CH=CH$_2$ | double | 665.3(M$^+$ + 1) |
| 8rr | N[CH(CH$_2$F)$_2$]CH$_2$Ph(4-OMe) | double | 823.3(M$^+$ + 1) |
| 8ss | NHO—tBu | double | 626.1(M$^+$ + 1) |
| 8tt | NHOMe | double | 655.6(M$^+$ + 1) |
| 8uu | 1-phthalimido | single | |
| 8vv | 4-morpholinyl | double | |

EXAMPLES 9a AND 9b

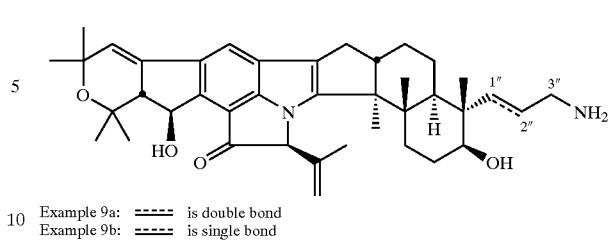

Example 9a: ===== is double bond
Example 9b: ----- is single bond

To compound of Example 7 (241 mg, containing approximately 10% 1",2"-dihydro-3"-allylamine) in CH$_2$Cl$_2$ (4 mL) at 25° C. was added N,N-dimethyl-barbituric acid (85 mg) followed by Pd(PPh$_3$)$_4$ (4 mg). The solution was heated to 35° C. for 48 h. The solvent was removed under reduced pressure and pure 3"-amine (Example 9a, 171 mg) and 1",2"-dihydro-3"-amine (Example 9b, 23 mg) were obtained following PTLC (8×1000 μm silica gel plates) using CH$_2$Cl$_2$ as eluant. Both products were characterized by $^1$H NMR and mass spectrometry [m/z: 625.6 (M$^+$+1) for Example 9a].

EXAMPLE 10

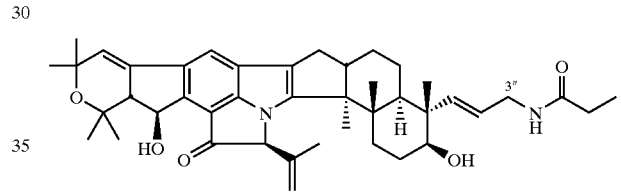

To compound of Example 9a (7.5 mg) in CH$_2$Cl$_2$ (0.5 ml) at 0° C. was added propionic anhydride (1.55 μL) followed by pyridine (9.71 μL) and then warmed to room temperature and aged for 16 h. The volatiles were removed under reduced pressure and pure 3"-amide [5.6 mg, R$_f$=0.58 (CH$_2$Cl$_2$/CH$_3$OH/NH$_4$OH; 9/1/0.01]. was obtained following PTLC on silica gel (1×500 μm plate) using CH$_2$Cl$_2$/CH$_3$OH/NH$_4$OH (9/1/0.01) as eluant. The title product thus obtained was characterized by $^1$H NMR and MS [m/z: 710.2 (M$^+$+1)].

EXAMPLE 11

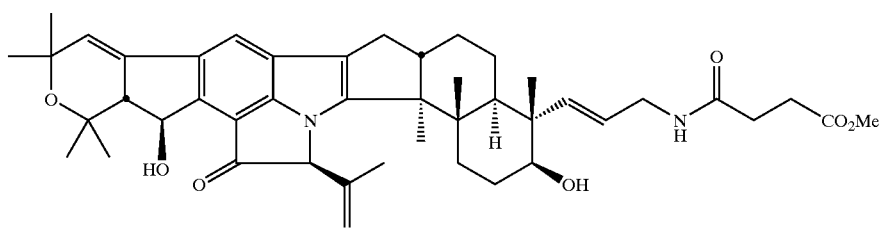

To compound of Example 9a (15.7 mg) in CH$_2$Cl$_2$ (0.8 mL) at 0° C. were added iPr$_2$NEt (4.38 μL) and DMAP (0.6 mg) followed by methyl 4-chloro-4-oxobutyrate (3.08 μL) dropwise. The solution was aged for 2 h and pure title compound (6.6 mg, R$_f$=0.72 (CH$_2$Cl$_2$/MeOH/NH$_4$OH; 9/1/0.01) was obtained following PTLC on silica gel (1×1000 μm plate) using CH$_2$Cl$_2$/MeOH/NH$_4$OH (9/1/0.01) as eluant. The product thus obtained was characterized by $^1$H NMR and MS [m/z: 739.2 (M$^+$+1)].

EXAMPLES 11a–11uuu

Following the general procedure described in Example 11 using a nodulisporic acid derivative containing either an unsubstituted or monosubstituted amine at 3″, the following compounds were prepared using the appropriate acylating agents:

TABLE 4

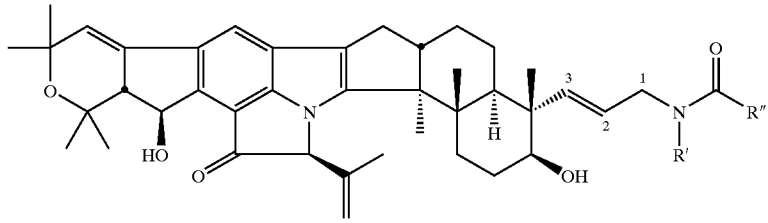

| Ex | R″ Group | R′ Group | Mass Spec |
|---|---|---|---|
| 11a | Me | C(Me)$_2$CN | |
| 11b | Me | CH$_2$CF$_2$CF$_2$CF$_3$ | 831.6(M − H$_2$O) |
| 11c | Et | C(Me)$_2$CN | |
| 11d | Et | H | 681.1(M$^+$ + 1) |
| 11e | Et | Me | 695.0(M$^+$ + 1) |
| 11f | CH(CH$_3$)$_2$ | C(Me)$_2$CN | |
| 11g | CH$_2$CH(CH$_3$)$_2$ | Me | 723.3(M$^+$ + 1) |
| 11h | CH$_2$CH(CH$_3$)$_2$, 13-O$_2$C(iBu) | Me | 807.3(M$^+$ + 1) |
| 11i | C(CH$_3$)$_3$ | H | 709.2(M$^+$ + 1) |
| 11j | C(CH$_3$)$_3$ | Me | 723.3(M$^+$ + 1) |
| 11k | CH$_2$C(CH$_3$)$_3$ | Me | 737.3(M$^+$ + 1) |
| 11l | Ph(2,4,6-F) | Me | 797.1(M$^+$ + 1) |
| 11m | Ph(2,5-CF$_3$) | Me | 879.1(M$^+$ + 1) |
| 11n | Ph(4-CN) | Me | 768.2(M$^+$ + 1) |
| 11o | Ph(4-F) | H | 747.1(M$^+$ + 1) |
| 11p | Ph(4-OMe) | Me | 773.3(M$^+$ + 1) |
| 11q | Ph(4-tBu) | Me | 799.3(M$^+$ + 1) |
| 11r | 2-furfuryl | Me | 733.2(M$^+$ + 1) |
| 11s | 2-furfuryl, 13-O$_2$C(2-furfuryl) | Me | 827.2(M$^+$ + 1) |
| 11t | 2-thienyl | H | 735.2(M$^+$ + 1) |
| 11u | 2-thienyl | Me | 749.1(M$^+$ + 1) |
| 11v | CF$_3$ | H | 721.0(M$^+$ + 1) |
| 11w | CH$_2$CH$_2$CO$_2$Me | H | 739.2(M$^+$ + 1) |
| 11x | CH$_2$CH$_2$CO$_2$Me | H[7-O$_2$CCH$_2$CH$_2$CO$_2$Me] | 853.3(M$^+$ + 1) |
| 11y | CH$_2$CH$_2$CH$_2$CO$_2$Me | H | 753.3(M$^+$ + 1) |
| 11z | CH$_2$CH$_2$CH$_2$CO$_2$Me [3-O$_2$C(CH$_2$)$_3$CO$_2$CH$_3$] | H | 881.3(M$^+$ + 1) |
| 11aa | CH$_2$CN | OMe | 722.8(M$^+$ + 1) |
| 11bb | CO$_2$Me | c-C$_3$H$_5$ | 751.0(M$^+$ + 1) |
| 11cc | CO$_2$Me | Me | 725.3(M$^+$ + 1) |
| 11dd | D-CH(Me)NHCO$_2$—tBu | nPr | 838.1(M$^+$ + 1) |

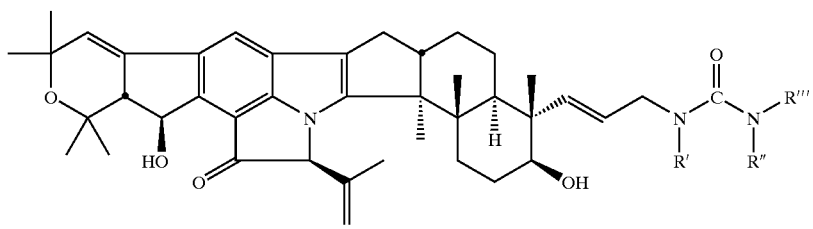

| Ex | NR″R‴ Group | R′ Group | Mass Spec |
|---|---|---|---|
| 11ee | NH—Me | c-C$_3$H$_5$ | 722.4(M$^+$ + 1) |
| 11ff | NH—Me | CH(CO$_2$Me)CH(Me)CH$_2$CH$_3$ | 810.7(M$^+$ + 1) |
| 11gg | NH—Me | Me | 696.2(M$^+$ + 1) |
| 11hh | NH—Et | Me | 710.2(M$^+$ + 1) |
| 11ii | NH—Et | nPr | 738.3(M$^+$ + 1) |
| 11jj | NH—Et | OMe | 726.4(M$^+$ + 1) |
| 11kk | NH—iPr | C(Me)$_2$CN | |
| 11ll | NH—tBu | c-C$_3$H$_5$ | 764.4(M$^+$ + 1) |

TABLE 4-continued

| | | | |
|---|---|---|---|
| 11mm | NH—tBu | H | 724.4(M+ + 1) |
| 11nn | NH—tBu | Me | 738.3(M+ + 1) |
| 11oo | NH—tBu | nPr | 766.4(M+ + 1) |
| 11pp | NH—tBu | OMe | 754.6(M+ + 1) |
| 11qq | NH(c-C$_6$H$_{11}$) | C(Me)$_2$CO$_2$Me | 850.7(M+ + 1) |
| 11rr | NHCH$_2$Ph | C(Me)$_2$CN | |
| 11ss | NHCH$_2$Ph | C(Me)$_2$CO$_2$Me | 858.9(M+ + 1) |
| 11tt | NHCH$_2$CH$_2$(2-thienyl) | CO$_2$Me | 851.2(M+ + 1) |
| 11uu | NHPh(4-F) | CH(s-Bu)CO$_2$Me | 890.4(M+ + 1) |
| 11vv | NH—Ph(4-F) | Me | 776.2(M+ + 1) |
| 11ww | NH—Ph(4-F) | nPr | 804.3(M+ + 1) |
| 11xx | NH—Ph(4-Me) | C(Me)$_2$CN | |
| 11yy | NH—Ph(4-OMe) | C(Me)$_2$CO$_2$Me | 874.5(M+ + 1) |
| 11zz | N(Me)Ph | Me | 772.3(M+ + 1) |
| 11aaa | (4-morpholinyl) | H | 738.3(M+ + 1) |
| 11bbb | (4-morpholinyl) | Me | 752.3(M+ + 1) |

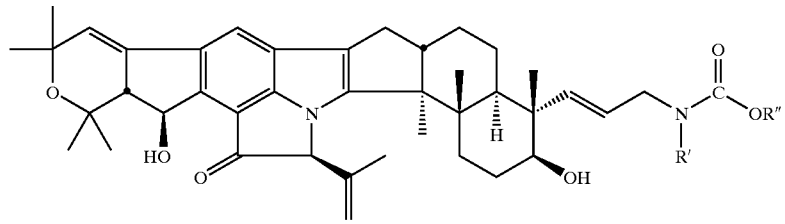

| Ex. | R″ Group | R′ Group | Mass Spec |
|---|---|---|---|
| 11ccc | Me | C(O)NH(CH$_2$)$_7$CH$_3$ | 852.4(M+ + 1) |
| 11ddd | Me | c-C$_3$H$_5$ | 723.0(M+ + 1) |
| 11eee | Me | H | 638.0(M+ + 1) |
| 11fff | Et | H | 697.1(M+ + 1) |
| 11ggg | Et | Me | 711.5(M+ + 1) |
| 11hhh | Et | NHCO$_2$Et | 783.0(M+ + 1) |
| 11iii | iBu | CH$_2$CH$_2$OCO$_2$—iBu | 869.1(M+ + 1) |
| 11jjj | iBu | Me | 739.3(M+ + 1) |
| 11kkk | sBu | H | 725.1(M+ + 1) |
| 11lll | tBu | H | 725.3(M+ + 1) |
| 11mmm | CH$_2$CH=CH$_2$ | H | 709.3(M+ + 1) |
| 11nnn | CH$_2$CH=CH$_2$ | Me | 723.1(M+ + 1) |
| 11ooo | CH$_2$Ph | Me | 773.5(M+ + 1) |
| 11ppp | Ph(4-NO$_2$) | Me | 804.0(M+ + 1) |
| 11qqq | | | 831.3(M+ + 1) |

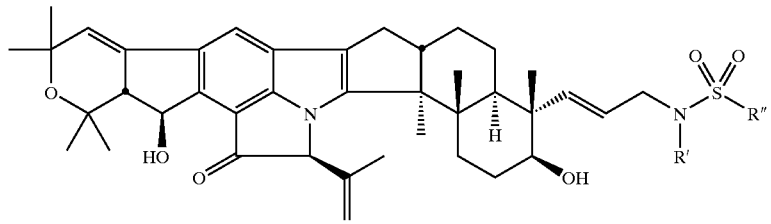

| Ex | R″ Group | R′ Group | Mass Spec |
|---|---|---|---|
| 11rrr | Me | C(Me)$_2$CN | |
| 11sss | 2-thienyl | C(Me)$_2$CN | |
| 11ttt | 2-thienyl | Me | 785.2(M+ + 1) |
| 11uuu | 5-(2-SMe)benzothiazolyl] | Me | 882.1(M+ + 1) |

EXAMPLE 12

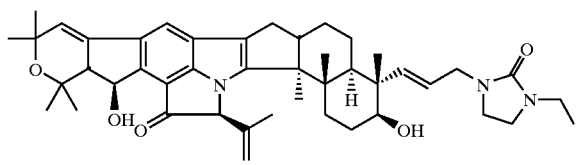

To a solution of Intermediate I (30 mg) in t-BuOH/THF (1/1) (2 ml), 4 Å molecular sieves were added and the solution was stirred for 2 minutes. N-ethylethylene-diamine (12 mg) and acetic acid (0.1 mL) were added to the solution and the reaction mixture was aged for 16 hours. It was then cooled to 0° C. and sodium triacetoxy-borohydride (30 mg, 0.144 mmol) was added to the solution in one portion. The reaction mixture was then stirred for 16 hours. It was partitioned between ethyl acetate (10 mL) and saturated NaHCO$_3$ (aq.) (10 mL), washed with brine, dried over sodium sulfate, filtered and concentrated. The crude product (33 mg) was used directly for the subsequent step.

To the above crude product in ethyl acetate (2 mL), 1,1-carbonyldiimidazole (11.5 mg) was added and the solution was stirred for 16 hours. It was then partitioned between ethyl acetate (10 mL) and water (5 mL), washed with saturated NaHCO3 (aq.) (7 mL), brine solution (5 mL), dried over sodium sulfate, filtered and concentrated. Purification by preparative chromatography (acetone/hexanes; 2/3) yielded 2.6 mg (7.3%) of the title product as a yellow solid which was characterized by $^1$H NMR and LC-MS [m/z: 722.3 (M+H)].

EXAMPLES 12a–12r

Following the general procedure of Example 12, the following compounds were prepared:

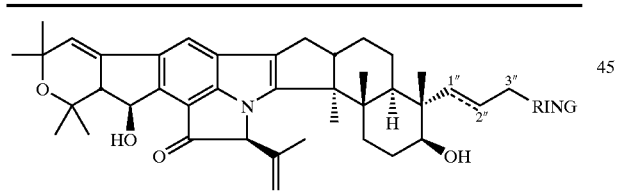

| Ex | Ring | 1″–2″ | Mass Spec |
|---|---|---|---|
| 12a | 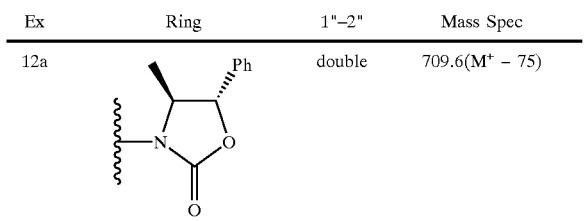 | double | 709.6(M$^+$ − 75) |
| 12b | 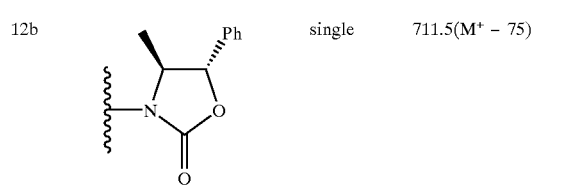 | single | 711.5(M$^+$ − 75) |

-continued

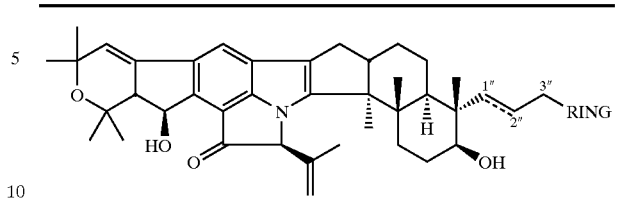

| Ex | Ring | 1″–2″ | Mass Spec |
|---|---|---|---|
| 12c | 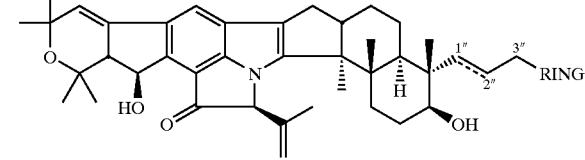 | double | 771.1(M$^+$ + 1) |
| 12d | 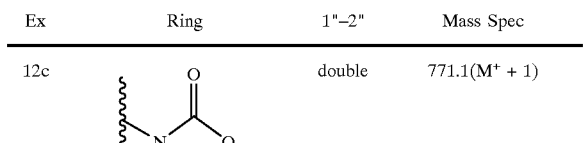 | double | 723.0(M$^+$ + 1) |
| 12e | 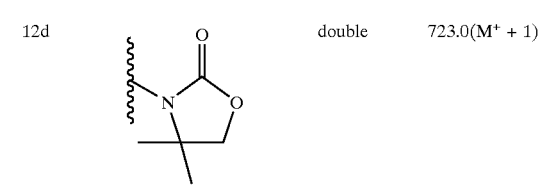 | double | 667.4(M$^+$ − 75) |
| 12f | 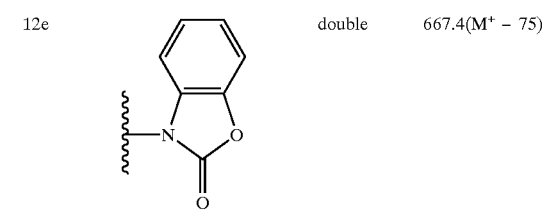 | double | 931.3(M$^+$ + TFA) |
| 12g | 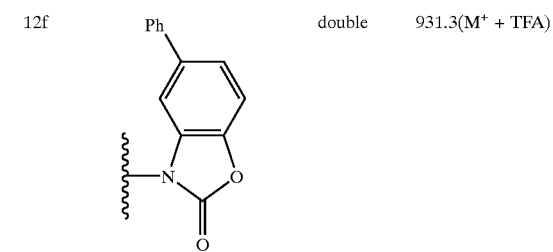 | double | 681.5(M$^+$ − 75) |
| 12h | 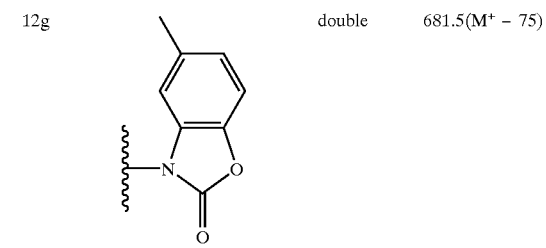 | double | 749.1(M$^+$ + 1) |

-continued

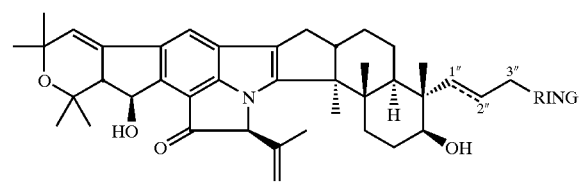

| Ex | Ring | 1"–2" | Mass Spec |
|---|---|---|---|
| 12i | 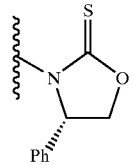 | single | 787.3(M⁺ + 1) |
| 12j | 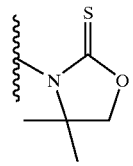 | double | 739.3(M⁺ + 1) |
| 12k | 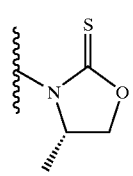 | double | 725.3(M⁺ + 1) |
| 12l | 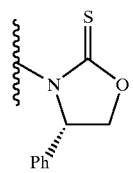 | double | 787.3(M⁺ + 1) |
| 12m | 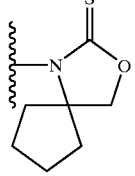 | double | 765.4(M⁺ + 1) |
| 12n | 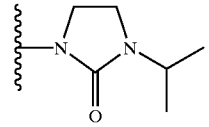 | double | 736.3(M⁺ + 1) |
| 12o | 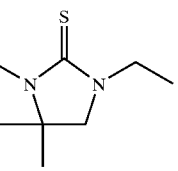 | single | 782.3(M⁺ + 1) |

-continued

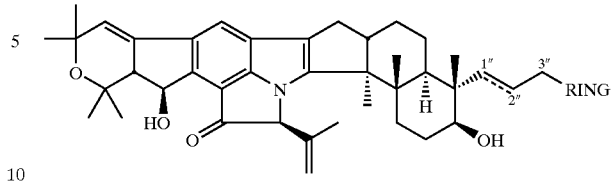

| Ex | Ring | 1"–2" | Mass Spec |
|---|---|---|---|
| 12p | 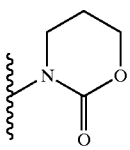 | double | 709.2(M⁺ + 1) |
| 12q | 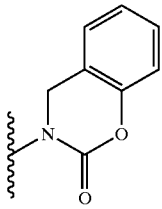 | double | 756.2(M⁺ + 1) |
| 12r | 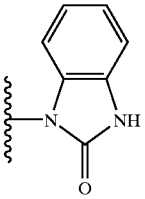 | double | 666.4(M⁺ − 75) |

*Compounds with single bond were obtained as a minor product of the reductive amination step.

EXAMPLE 13

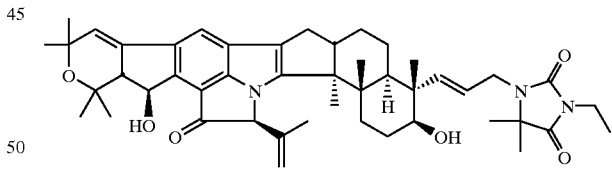

To a solution of the 3"-amine (Example 8 mm, 18 mg) in $CH_2Cl_2$ (0.3 mL) were added pyridine (0.3 mL) and ethyl isocyanate (0.025 mL) and the reaction was aged at room temperature for 24 h. The solution was diluted with ethyl acetate (10 mL), washed with 10% citric acid, water and dried ($Na_2SO_4$). The solution was filtered, concentrated under reduced pressure and purified by PTLC on silica gel (Analtech 1×1000 μm plate) using EtOAc/hexanes (1/1) as the eluant. The product (12 mg, 63%) thus obtained was characterized by proton NMR and mass spectrometry [m/z: 764.2 (M⁺+1)].

EXAMPLES 13a–13gg

Following the general procedure of Example 13, the following compounds were prepared:

| Ex | Ring | 1"–2" | Mass Spec |
|---|---|---|---|
| 13a | (1-methyl-5-methyl-hydantoin) | double | 736.5 (M+ + 1) |
| 13b | (1-ethyl-5-methyl-hydantoin) | double | 750.6 (M+ + 1) |
| 13c | (1-methyl-5-sec-butyl-hydantoin) | double | 778.5 (M+ + 1) |
| 13d | (3-methyl-cyclopentane-spiro-hydantoin) | double | 776.3 (M+ + 1) |
| 13e | (3-ethyl-cyclopentane-spiro-hydantoin) | double | 790.6 (M+ + 1) |
| 13f | (3-ethyl-5,5-dimethyl-2-thiohydantoin) | double | 780.6 (M+ + 1) |

-continued

| Ex | R^g Group | Mass Spec |
|---|---|---|
| 13g | (structure: N-propyl thiohydantoin) | double 752.4 (M+ + 1) |

| Ex | R^g Group | Mass Spec |
|---|---|---|
| 13h | H | 736.8 (M+ + 1) |
| 13i | Me | 750.6 (M+ + 1) |
| 13j | iPr | 778.6 (M+ + 1) |
| 13k | tBu | 792.6 (M+ + 1) |
| 13l | $(CH_2)_5CH_3$ | 820.5 (M+ + 1) |
| 13m | $(CH_2)_7CH_3$ | 848.3 (M+ + 1) |
| 13n | c-$C_6H_{11}$ | 817.8 (M+ + 1) |
| 13o | Ph | 812.3 (M+ + 1) |
| 13p | Ph(3,5-$CF_3$) | 948.2 (M+ + 1) |
| 13q | Ph(3-$CF_3$) | 880.6 (M+ + 1) |
| 13r | Ph(2,4-Cl) | 880.4 (M+ + 1) |
| 13s | Ph(4-Cl) | 846.6 (M+ + 1) |
| 13t | Ph(4-Cl) [13-$O_2$CPh Ph(4-Cl)] | 998.7 (M+ + 1) |
| 13u | Ph(4-$CO_2$Me) | 884.6 (M+ + 1) |
| 13v | Ph(4-F) | 830.7 (M+ + 1) |
| 13w | Ph(4-$NMe_2$) | 855.3 (M+ + 1) |
| 13x | Ph(4-$NMe_2$) [13-$O_2$CPh(4-$NMe_2$)] | 1017.6 (M+ + 1) |
| 13y | Ph(4-OMe) | 842.7 (M+ + 1) |
| 13z | 1-naphthyl | 862.6 (M+ + 1) |
| 13aa | $CH_2$Ph | 826.8 (M+ + 1) |
| 13bb | $C(Me)_2$(4-pyridyl) | 855.7 (M+ + 1) |
| 13cc | $CH_2CH_2$(2-thienyl) | 846.5 (M+ + 1) |
| 13dd | $CH_2CH_2CO_2$Et | 836.4 (M+ + 1) |
| 13ee | $CO_2$Et | 808.6 (M+ + 1) |
| 13ff | (cyclopropyl-phenyl structure) | 852.7 (M+ + 1) |

EXAMPLE 14

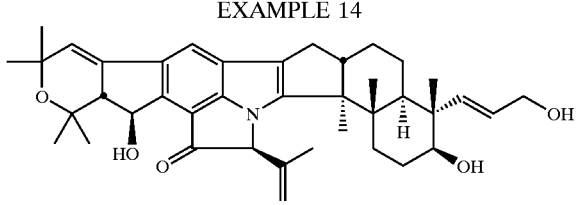

To Intermediate I (1.248 g) in THF (20 mL) at 0° C. was added 9-BBN (16 mL, 0.5M in THF) dropwise over 30 min. After an additional 20 min, the solution was warmed to 25° C. After aging for 4 h, the solution was cooled to 0° C. and $HOCH_2CH_2NH_2$ (0.48 mL) was added dropwise, the cooling bath was removed and the solution was stirred for 30 min at 25° C. Pure 3"-alcohol (1.149 g) was obtained following flash chromatography on silica gel without additional workup using 9/1 $CH_2Cl_2$/MeOH as eluant. The product was characterized by $^1$H NMR and MS [m/z: 626.3 M+ +1)].

EXAMPLE 15

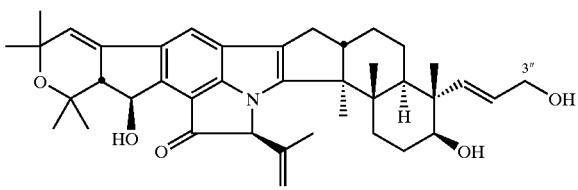

The procedure described in Example 4 was followed to remove the trimethylsilyl protecting group of Intermediate VIb to provide the title compound which was characterized by $^1$H NMR and MS [m/z: 628.0 (M$^+$+1)].

EXAMPLE 16

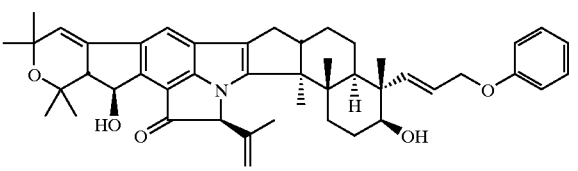

To a solution of Ph$_3$Bi (26 mg) in CH$_2$Cl$_2$ (0.9 mL) at room temperature was added 32% peracetic acid (15 μL). After 5 min, compound of Example 14 (30 mg) was added as a solution in CH$_2$Cl$_2$ (0.9 mL). After 1 min, Cu(OAc)$_2$ (4 mg) was added. The solution was aged for 1 hr at room temperature and for 6 h at 39° C. The reaction was quenched by the addition of saturated NaHCO$_3$(aq), extracted with CH$_2$Cl$_2$ and dried (Na$_2$SO$_4$). The solution was filtered, concentrated under reduced pressure and pure 3″-phenoxy ether (4 mg) was obtained following PTLC on silica gel (1×1000 μm plate) using 1/2 acetone/hexanes as eluant. The product thus obtained was characterized by $^1$H NMR and MS [m/z: 702.4 (M$^+$+1)].

EXAMPLE 17

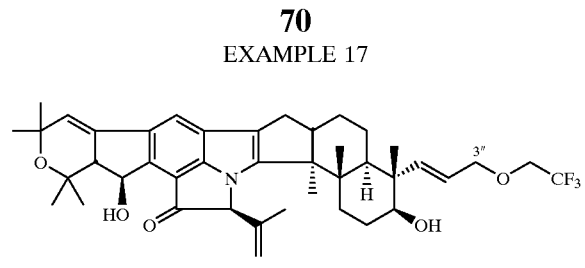

To Intermediate VIa (20 mg) in CH$_2$Cl$_2$ at room temperature was added 1,1'-(azodicarbonyl)dipiperidine (14 mg). After 5 min, (nBu)$_3$P (14 μL) followed by 2,2,2-trifluoroethanol (10 μL). After 30 min at rt, the volatiles were removed under reduced pressure and 7,24-bis-O-trimethylsilyl protected title compound (17.5 mg) was obtained following PTLC on silica gel (1×1000 μm plate) using 2/8 acetone/hexanes as eluant. The pure product thus obtained was deprotected using the procedure described in Example 4 to provide the title compound which was characterized by $^1$H NMR and MS [m/z: 690.1 (M$^+$+1-H$_2$O)].

EXAMPLES 17a–17j

Following the general procedure of Examples 16 or 17, the following compounds were prepared:

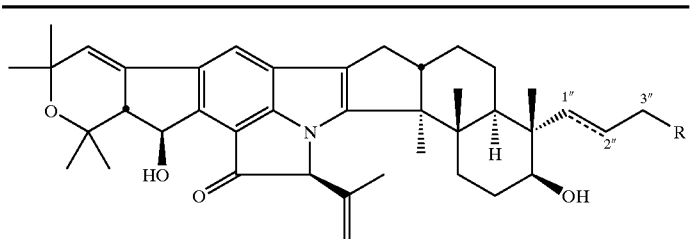

| Entry | R group | Mass Spec |
| --- | --- | --- |
| 17a | Cl (double) | |
| 17b | N$_3$ | 651.3 (M$^+$ + 1) |
| 17c | OMe | 640.0 (M$^+$ + 1) |
| 17e | OPh(2-NH$_2$) | 717.1 (M$^+$ + 1) |
| 17f | S-(2-pyridyl) | |
| 17g | S-(2-pyrimidinyl) | |
| 17h | S-(2-thiazolyl) | |
| 17i | S-(4-pyridyl) | |
| 17j | S-2-[(6-MeO)benzthiazolyl] | |
| 17k | SC(O)CH$_3$ | |

EXAMPLE 18

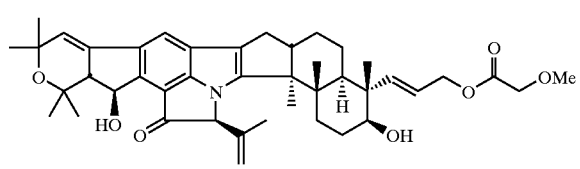

To compound of Example 14 (23 mg) in CH$_2$Cl$_2$ (1 mL) at 4° C. was added iPr$_2$NEt (125 μL), DMAP (7 mg), methoxyacetic acid (3.5 μL) followed by BOP (20 mg). The solution was aged for 2 h at 0° C. and 2 h at rt. Pure titleproduct (17.8 mg) was obtained following PTLC purification on silica gel (1×1000 μm plate) using 1/2 acetone/

EXAMPLE 19

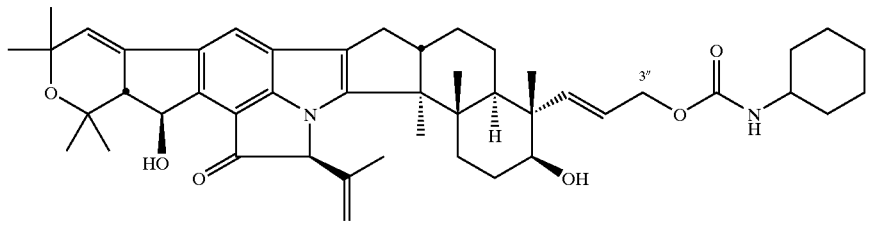

To compound of Example 14 (25 mg) in acetonitrile (0.8 mL) at room temperature was added Et$_3$N (20 μL) followed by cyclohexyl isocyanate (5 μL). After aging for 2 d, pure title product (25.8 mg) was obtained by PTLC on silica gel (1×1000 μm plate) without workup using 5/95 MeOH/CHCl$_3$ as eluant. The product thus obtained was characterized by $^1$H NMR and MS [m/z: 751.0 (M$^+$+1)].

EXAMPLE 20

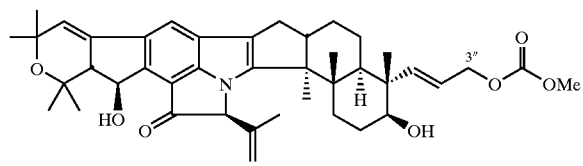

To Intermediate VIa (62 mg) in CH2Cl2 (0.5 mL) at 4° C. were added 4 Å molecular sieves followed by dimethyl pyrocarbonate (0.5 mL) and Et3N (10 μL). The solution was aged for 20 min at room temperature and then heated to 40° C. for 2.5 h. The volatiles were removed under reduced pressure and pure 7,24-bis-O-trimethylsilyl protected title product (27 mg) was obtained following PTLC on silica gel (1×1500 μm plate) using 2/8 EtOAc/hexanes as eluant. The product thus obtained was characterized by $^1$H NMR.

The trimethylsilyl protecting groups were removed using the general procedure described in Example 4 to provide the title compound characterized by NMR and MS [m/z: 684.2 (M++1)].

EXAMPLES 20a–20cc

Following the general procedure of Examples 18, 19 or 20, the following compounds were prepared:

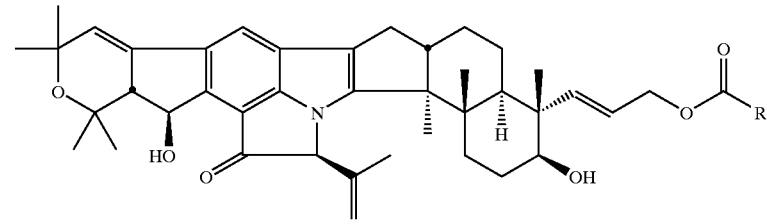

| Ex | R Group | Mass Spec |
|---|---|---|
| 20a | Me | 668.5 (M$^+$ + 1) |
| 20b | Et | 682.0 (M$^+$ + 1) |
| 20c | c-C$_3$H$_5$ | 694.0 (M$^+$ + 1) |
| 20d | CH$_2$CF$_3$ | 736.0 (M$^+$ + 1) |
| 20e | CH$_2$(2-thienyl) | 750.0 (M$^+$ + 1) |
| 20f | CH$_2$N(Me)$_2$ | 711.2 (M$^+$ + 1) |
| 20g | CH$_2$NHC(O)Me | 725.0 (M$^+$ + 1) |
| 20h | (2-pyrrolidinyl) | 736.1 (M + NH$_4$) |
| 20i | (2-pyridyl) | 731.0 (M$^+$ + 1) |
| 20j | (3-furyl) | 720.0 (M$^+$ + 1) |
| 20k | (3-thienyl) | 736.0 (M$^+$ + 1) |
| 20l | [2-((N—Ac)pyrrolidinyl)] | 765.1 (M$^+$ + 1) |

-continued

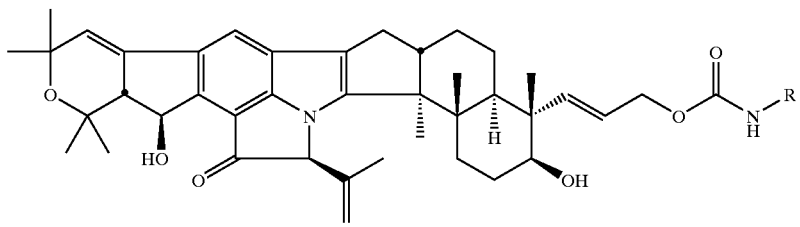

| Ex | R | Mass Spec |
|---|---|---|
| 20m | Me | 683.0 (M⁺ + 1) |
| 20n | Et | 697.5 (M⁺ + 1) |
| 20o | nPr | 711.0 (M⁺ + 1) |
| 20p | iPr | 711.5 (M⁺ + 1) |
| 20q | nBu | 725.0 (M⁺ + 1) |
| 20r | t-Bu | 725.0 (M⁺ + 1) |
| 20s | c-$C_5H_{11}$ | 751.0 (M⁺ + 1) |
| 20t | $CH_2CO_2Et$ | 755.0 (M⁺ + 1) |
| 20u | Ph(2-$OCF_3$) | 846.1 (M + $NH_4$) |
| 20v | Ph(3-OMe) | 775.0 (M⁺ + 1) |
| 20w | Ph(4-$CF_3$) | 813.0 (M⁺ + 1) |
| 20x | Ph(4-Cl) | 796.0 (M + $NH_4$) |
| 20y | Ph(4-CN) | 770.3 (M⁺ + 1) |
| 20z | Ph(4-$CO_2Et$) | 817.2 (M⁺ + 1) |
| 20aa | Ph[4-(6-methyl-benzothiazol-2-yl)] | 892.1 (M⁺ + 1) |
| 20bb | [tetrahydrofurfuryl] | 741.2 (M + $NH_4$) |

EXAMPLE 21

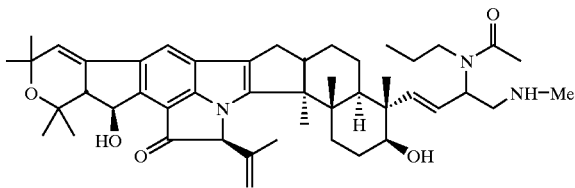

To Intermediate I (25 mg) in anhydrous MeOH (0.2 mL) at 25° C. was added acetic acid (2.9 μL) followed by n-propyl amine (4.1 μL) and 4 Å powdered molecular sieves (30 mg). After 10 min, methyl isonitrile (2.3 μL) was added and the mixture was aged for 36 h. By TLC, a separable mixture of 3"-diastereomers (~1:1) was formed. The entire reaction content was transferred to two 1000 μm silica gel PTLC plates using methylene chloride (2 mL) to ensure complete transfer. The preparative plates were focused using acetone as eluant and permitted to air dry (~15 min). The pure 3"-isomers were obtained (7.5 mg mobile isomer A and 9.3 mg polar isomer B) following PTLC using 1/6/93 $NH_4OH$/MeOH/$CHCl_3$ as eluant (three developments). Both products were characterized by ¹H NMR and mass spectrometry [m/z: 766.1 (M⁺+1)].

EXAMPLES 21a–21hh

The following compounds were prepared following the general procedure of Example 21 and using the appropriate amine, carboxylic acid and isonitrile:

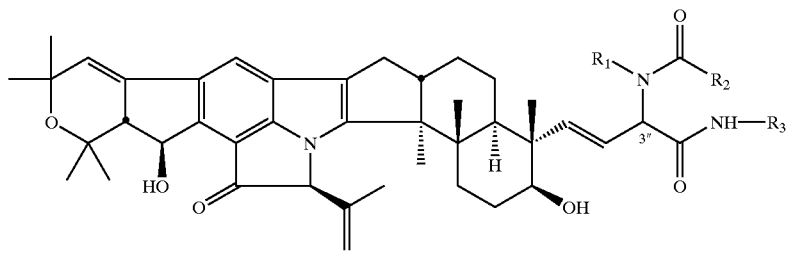

| Ex | $R_1$ | $R_2$ | $R_3$ | 3" Isomer* | Mass Spec |
|---|---|---|---|---|---|
| 21a | H | H | tBu | A & B | |
| 21b | H | Me | tBu | A & B | |
| 21c | H | Me | cHex | A & B | |
| 21d | H | Me | Me | A & B | |
| 21e | Me | Me | Me | A & B | 738.1 (M⁺ + 1) |
| 21f | Et | 2-pyridyl | Me | A | 815.2 (M⁺ + 1) |

-continued

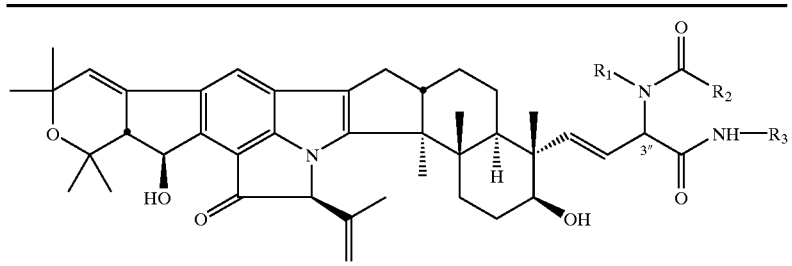

| Ex | R₁ | R₂ | R₃ | 3" Isomer* | Mass Spec |
|---|---|---|---|---|---|
| 21g | Et | 2-pyridyl | Me | B | 815.2 (M⁺ + 1) |
| 21h | Et | CH₂NHAc | Me | A & B | 838.2 (M⁺ + 1) |
| 21i | Et | CH₂NHAc | tBu | A | 838.2 (M⁺ + 1) |
| 21j | Et | CH₂NHAc | tBu | B | 838.2 (M⁺ + 1) |
| 21k | Et | Me | Me | A | 752.1 (M⁺ + 1) |
| 21l | Et | Me | Me | B | 752.1 (M⁺ + 1) |
| 21m | nPr | Et | Me | A | 780.1 (M⁺ + 1) |
| 21n | nPr | Et | Me | B | 780.1 (M⁺ + 1) |
| 21o | nPr | Me | Me | A | 766.1 (M⁺ + 1) |
| 21p | nPr | Me | Me | B | 766.1 (M⁺ + 1) |
| 21q | nPr | Me | tBu | A | 808.2 (M⁺ + 1) |
| 21r | nPr | Me | tBu | B | 808.2 (M⁺ + 1) |
| 21s | CH₂CH₂OH | Me | Me | A | 768.1 (M⁺ + 1) |
| 21t | CH₂CH₂OH | Me | Me | B | 768.1 (M⁺ + 1) |
| 21u | allyl | H | tBu | A & B | |
| 21v | allyl | Me | cC₆H₁₁ | A & B | 833.0 (M⁺ + 1) |
| 21w | allyl | Me | cC₆H₁₁ | A | 833.0 (M⁺ + 1) |
| 21x | allyl | Me | Me | A | 765.0 (M⁺ + 1) |
| 21y | allyl | Me | Me | B | 765.0 (M⁺ + 1) |
| 21z | allyl | Me | nBu | A & B | 807.0 (M⁺ + 1) |
| 21aa | 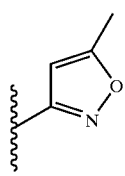 | Me | tBu | A | 847.5 (M⁺ + 1) |
| 21bb | 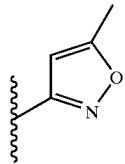 | Me | tBu | B | 847.5 (M⁺ + 1) |
| 21cc | 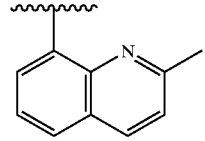 | Me | tBu | A | 907.5 (M⁺ + 1) |
| 21dd | 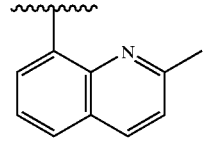 | Me | tBu | B | 907.5 (M⁺ + 1) |
| 21ee | 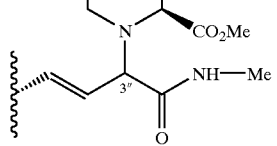 | Me | | A | |
| 21ff | | Me | | B | |

-continued

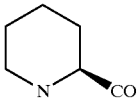

| Ex | $R_1$ | $R_2$ | $R_3$ | 3" Isomer* | Mass Spec |
|---|---|---|---|---|---|
| 21gg | 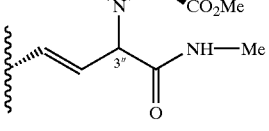 | Me | A | | |
| 21hh | | Me | B | | |

*A = mobile isomer by TLC on silica gel; B = polar isomer by TLC on silica gel. A & B = mixture not separated.
**2-Piperidinecarboxylic acid and L-proline were used; their caboxylic acids were transformed into the methyl esters under the standard reaction conditions.

EXAMPLE 22

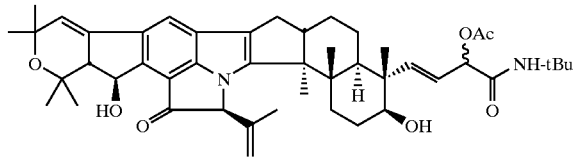

To Intermediate I (70 mg) in MeOH (460 μL) at 25° C. was added water (40 μL) followed by glacial acetic acid (90 μL) and t-BuNC (90 μL) and the solution was aged for 23 h. The solution was purified by PTLC without workup (3×1000 μm silica gel plates) in 3/1 hexanes/acetone (3 developments). The pure 3"-acetoxy isomers thus obtained (41 mg mobile isomer A and 21 mg polar isomer B) were characterized by $^1$H NMR and mass spectrometry [m/z: 691.4 (M-75) for Isomer A and 767.0 (M$^+$+1) for Isomer B].

EXAMPLE 23

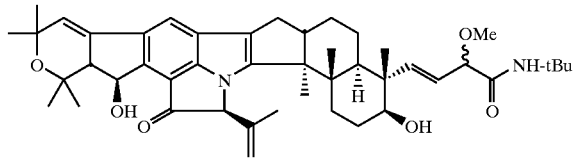

To a solution of Intermediate I (15 mg) in methanol (0.1 mL), t-butyl isonitrile (3.9 mg) was added followed by pyridinium p-toluenesulfonate (9 mg). After stirring at room temperature for 48 hrs, water was added to the reaction mixture and it was extracted into ethyl acetate (10 mL). The organic layer was washed with saturated NaHCO$_3$ (10 mL), brine (10 mL) and dried over sodium sulfate. It was then filtered, concentrated and purified by preparative chromatography (dichloromethane/acetone; 4/1) to yield 4.6 mg (26%) of the title compound (RS isomers) as a yellow solid and was characterized by $^1$H NMR and LC-MS [739.5 (M+H)].

EXAMPLE 24

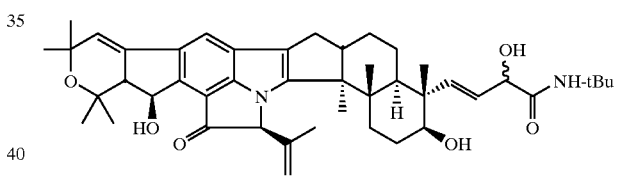

Method A

To compound of Example 22 (10 mg) in allyl alcohol (1 mL) at 25° C. in a 1 dram vial was added Ti(OiPr)4 (10 μL). The solution was heated to 130° C. in an oil bath for 4.5 h the cooled to 25° C. The solution was poured into water, extracted with EtOAc and dried (MgSO$_4$). The solution was filtered and concentrated to dryness under reduced pressure. Pure title compound (quant) was obtained following PTLC (1×1500 μm silica gel plate) using 2/1 hexanes/acetone as eluant. The pure product was characterized by $^1$H NMR and mass spectrometry [m/z: 725.3 (M$^+$+1)].

Method B

To compound of Example 22 (20 mg) in a 1 dram vial was added methanol (0.4 mL) and Otera's catalyst (20 mg) and the solution was heated to 62° C. for 6 h, then aged at 25° C. overnight. Partially purified product (14.5 mg) was obtained following PTLC without workup (1×500 μm silica gel plate) using 2/1 hexanes/acetone as eluant. Pure title compound (11.8 mg) was obtained following repurification by PTLC (1×500 μm silica gel plate) using 2/1 hexanes/acetone as eluant. The pure product was characterized by $^1$H NMR and mass spectrometry [m/z: 725.3 (M$^+$+1)].

EXAMPLES 24a–24aa

Following the general procedures of Examples 21 and 22 and 23 the following compounds were prepared:

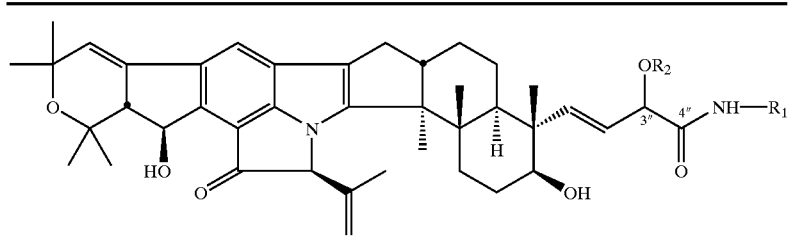

| Ex | R₁ Group | R₂ Group | 3" Isomer | Mass Spec |
|---|---|---|---|---|
| 24a | Me | C(O)CH₃ | A | 649.3 (M − 75) |
| 24b | Me | C(O)CH₃ | B | |
| 24c | iPr | H | A & B | 711.3 (M⁺ + 1) |
| 24d | iPr | Me | A & B | 725.3 (M⁺ + 1) |
| 24e | tBu | Me | A & B | 739.5 (M⁺ + 1) |
| 24f | tBu | Et | A & B | 753.5 (M⁺ + 1) |
| 24g | tBu | iPr | A & B | 767.5 (M⁺ + 1) |
| 24h | tBu | nPr | A & B | 767.5 (M⁺ + 1) |
| 24i | tBu | C(O)Et | A & B | 781.3 (M⁺ + 1) |
| 24j | tBu | C(O)tBu | A | 809.3 (M⁺ + 1) |
| 24k | tBu | C(O)tBu | B | 809.3 (M⁺ + 1) |
| 24l | tBu | C(O)Ph | A & B | 829.6 (M⁺ + 1) |
| 24m | tBu | C(O)(2-pyridyl) | A & B | 830.5 (M⁺ + 1) |
| 24n | tBu | C(O)(3-furyl) | A & B | 819.0 (M⁺ + 1) |
| 24o | tBu | C(O)(3-thienyl) | A & B | 835.3 (M⁺ + 1) |
| 24p | tBu | C(O)CH₂OMe | B | |
| 24q | tBu | C(O)CH₂OMe | A | |
| 24r | tBu | C(O)NHMe | A | |
| 24s | tBu | C(O)NHEt | A | |
| 24t | tBu | C(O)N-iPr | A | |
| 24u | tBu | C(O)N-nPr | A | |
| 24v | tBu | C(O)NH-tBu | A | |
| 24w | tBu | C(O)NH-allyl | A | |
| 24x | tBu | C(O)NHPh | A | |
| 24y | tBu | C(O)NHPh(4-F) | A | |
| 24z | tBu | CO₂Me | A | 783.5 (M⁺ + 1) |
| 24aa | tBu | CO₂Me | B | 783.2 (M⁺ + 1) |

EXAMPLE 25

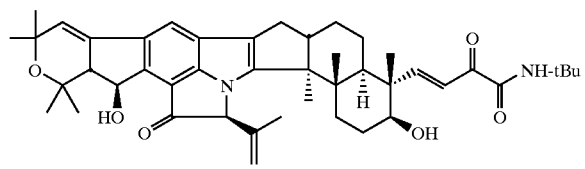

To a stirred solution of compound of Example 24 (88.5 mg) in CH₂Cl₂/hexanes (2/1, 1.75 ml) at 0° C. was added activated MnO₂ (106 mg). The mixture was allowed to warm up to room temperature and aged for 3.5 h. Excess MnO₂ was removed by filtration through Celite and the solvents were removed under reduced pressure. Pure title compound was isolated by preparative layer chromatography (EtOAc/hexanes, 2.5/1) giving (49.8 mg, 57%, R$_f$=0.73). The product thus obtained was characterized by ¹H NMR.

EXAMPLE 26

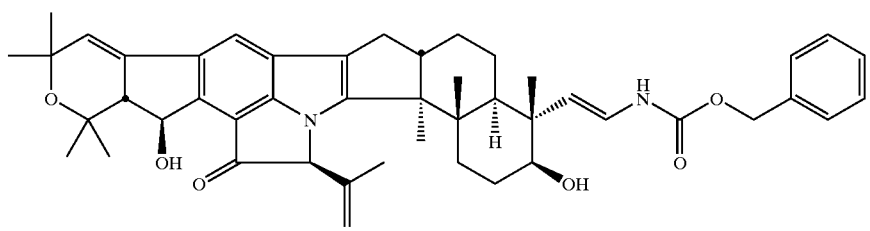

Step A. To Intermediate Va (50 mg) in CH$_2$Cl$_2$ (1.1 mL) at room temperature was added triethylamine (25 μL) followed by (PhO)2P(O)N3 (18 μL). After 18 h, the solution was purifed without workup by PTLC on silica gel (1×1000 μm plate) using 1/9 acetone/hexanes as eluant to give the corresponding 3"-acyl azide (46 mg) which was characterized by 1H NMR.

Step B. The product from Step A (46 mg) was dissolved in toluene (1 mL) and heated to 80° C. for 1.5 h. The solution was cooled to room temperature and the solvent was removed under reduced pressure to provide the corresponding 2"-isocyanate (44 mg) thus obtained was characterized by $^1$H NMR.

Step C. To a solution of product of Step B (15 mg) at room temperature was added benzyl alcohol (0.2 mL) and DMAP (2 mg). After aging for 18 h at rt, the volatiles were removed in vacuo. The residue thus obtained was purified on PTLC on silica gel (Analtech 1000 μm plates) using EtOAc/hexane (1/1) as the eluting solvent. The purified 7,24-bis-O-triethylsilyl protected title compound (10 mg) thus obtained was deprotected as described in Example 4 and the title compound was obtained and characterized by $^1$H NMR and mass-spectral analysis [m/z: 745.2 (M$^+$+1)].

EXAMPLE 26a

Following the general procedure of Example 26, Step C, the following compounds were prepared:

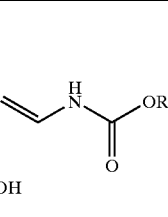

| Ex | R Group | Mass Spec |
|---|---|---|
| 26a | Me | 669.4 (M$^+$ + 1) |
| 26b | CH(Me)Ph (Isomer A) | 759.2 (M$^+$ + 1) |
| 26c | CH(Me)Ph (Isomer B) | 759.4 (M$^+$ + 1) |
| 26d | tBu | 711.6 (M$^+$ + 1) |

EXAMPLE 27

To a solution of Intermediate I (100 mg) and 2-aminopyrimidine (30 mg) in methanol (0.5 mL), isopropylisonitrile (22 mg) was added followed by acetic acid (18 mL). After stirring at room temperature for 48 hrs, water was added to the reaction mixture and it was extracted into ethyl acetate (20 mL). The organic layer was washed with saturated NaHCO$_3$ solution (10 mL), brine (10 mL) and dried over sodium sulfate. It was then filtered, concentrated, purified by preparative chromatography (dichloromethane/acetone; 3/2) and washed with ether to yield 85 mg (69%) of the product as a yellow solid and was characterized by $^1$H NMR and LC-MS [m/z: 770.7 (M+H)].

EXAMPLES 27a–27gg

Following the general procedure of Example 27 using the appropriate amino-substituted heteroaromatic compound and the appropriate isonitrile, the following compounds were prepared:

TABLE 12

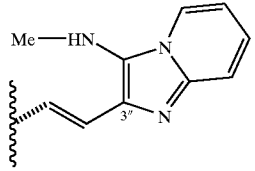

| Entry | R Group | Mass Spec |
|---|---|---|
| 27a | Me—HN— (imidazopyridine group) | 741.6 (M$^+$ + 1) |

TABLE 12-continued

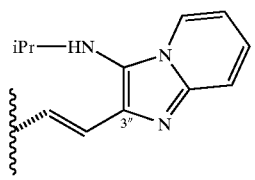

| Entry | R Group | Mass Spec |
|---|---|---|
| 27b | iPr—HN— (imidazopyridine group) | 769.7 (M$^+$ + 1) |

TABLE 12-continued
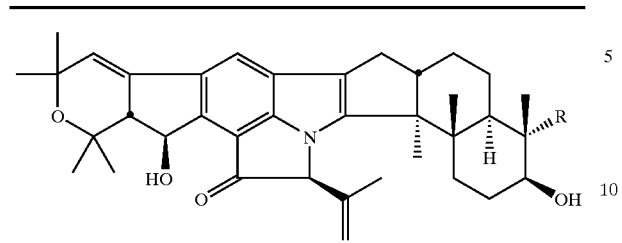
| Entry | R Group | Mass Spec |
|---|---|---|
| 27c | 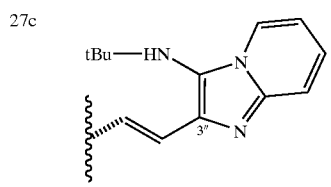 | 783.6 (M+ + 1) |
| 27d | 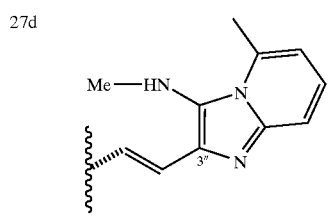 | 755.7 (M+ + 1) |
| 27e | 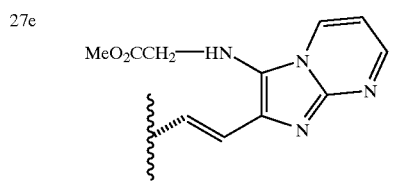 | 800.6 (M+ + 1) |
| 27f | 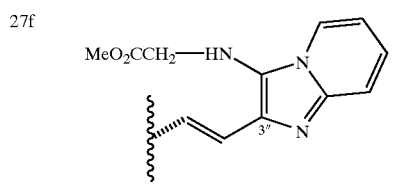 | 799.6 (M+ + 1) |
| 27g | 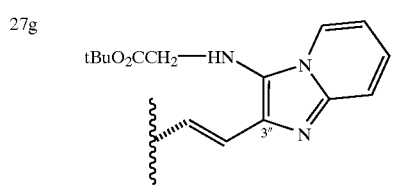 | 841.6 (M+ + 1) |
| 27h | 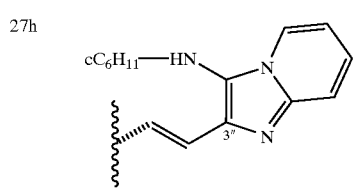 | 809.6 (M+ + 1) |
TABLE 12-continued
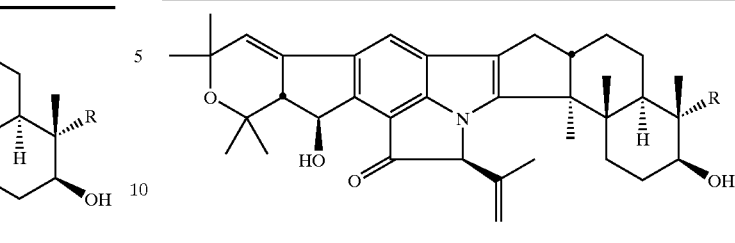
| Entry | R Group | Mass Spec |
|---|---|---|
| 27i | 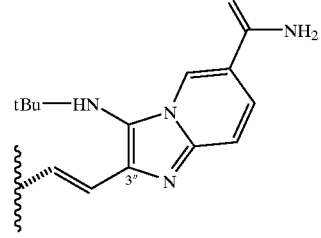 | 826.5 (M+ + 1) |
| 27j | 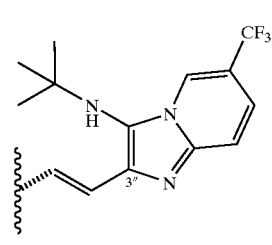 | 851.3 (M+ + 1) |
| 27k | 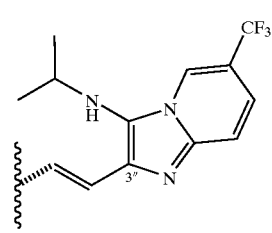 | 837.4 (M+ + 1) |
| 27l | 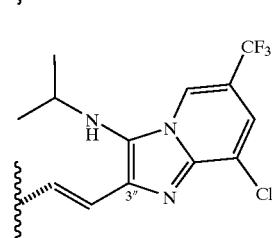 | 871.5 (M+ + 1) |
| 27m | 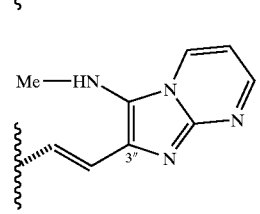 | 742.6 (M+ + 1) |
| 27n | 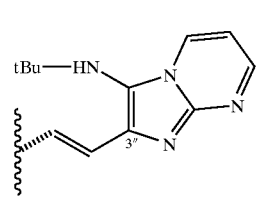 | 784.6 (M+ + 1) |

TABLE 12-continued
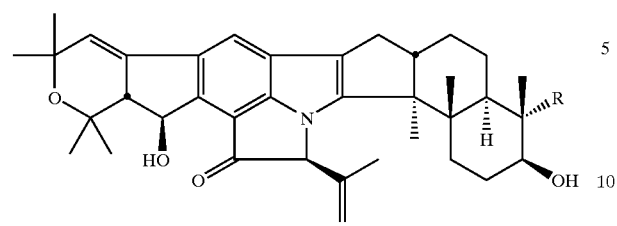
| Entry | R Group | Mass Spec |
|---|---|---|
| 27o | 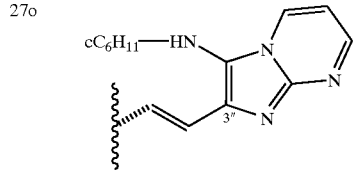 cC$_6$H$_{11}$—HN | 810.6 (M$^+$ + 1) |
| 27p | 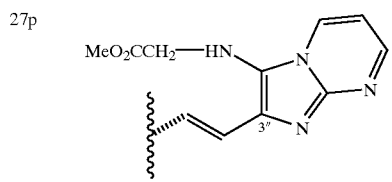 MeO$_2$CCH$_2$—HN | 800.6 (M$^+$ + 1) |
| 27q | 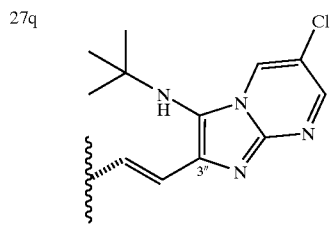 | 818.3 (M$^+$ + 1) |
| 27r | 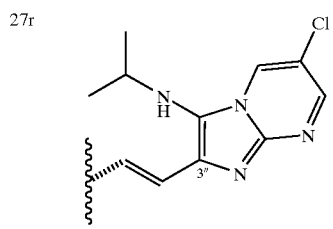 | 804.4 (M$^+$ + 1) |
| 27s | 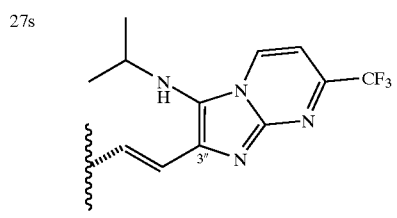 | 838.5 (M$^+$ + 1) |
| 27t | 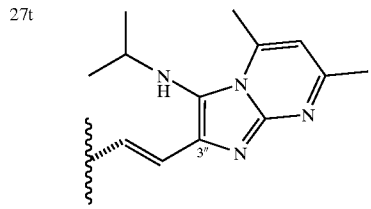 | |
TABLE 12-continued
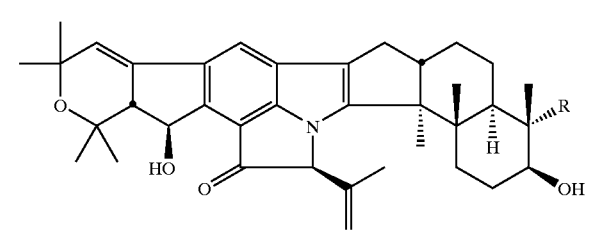
| Entry | R Group | Mass Spec |
|---|---|---|
| 27u | 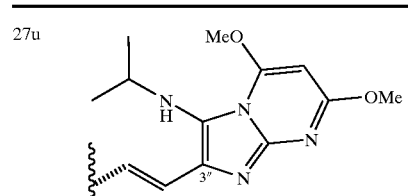 | |
| 27v | 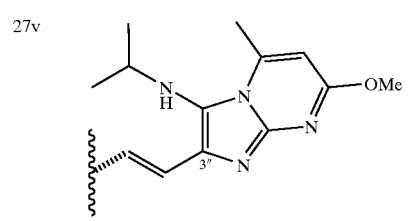 | |
| 27w | 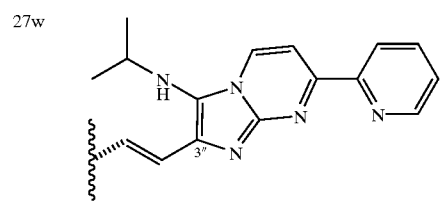 | |
| 27x | 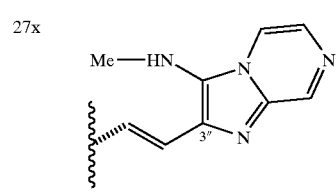 Me—HN | 742.4 (M$^+$ + 1) |
| 27y | 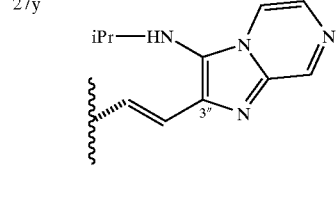 iPr—HN | 770.7 (M$^+$ + 1) |
| 27z | 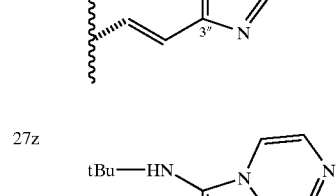 tBu—HN | 784.8 (M$^+$ + 1) |
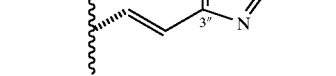

TABLE 12-continued

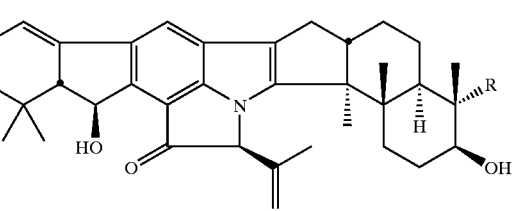

| Entry | R Group | Mass Spec |
|---|---|---|
| 27aa | 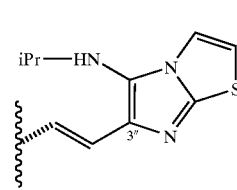 (tBu—HN, imidazothiazole) | 789.7 (M$^+$ + 1) |
| 27bb | (iPr—HN, imidazothiazole) | 775.3 (M$^+$ + 1) |
| 27cc | (tBu—HN, methyl-imidazothiazole) | 804.1 (M$^+$ + 1) |
| 27dd | (tBu—HN, imidazo-isoquinoline) | 833.3 (M$^+$ + 1) |
| 27ee | (tBu—NH, imidazo-quinoline) | 833.5 (M$^+$ + 1) |

EXAMPLE 28

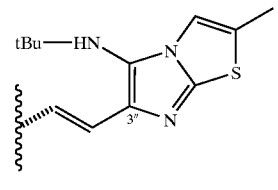

The procedure described in Example 4 was followed using Intermediate Va and L-serine allyl ester to provide the corresponding bis-protected amide. To this 7,24-bis-O-triethylsilyl-3"-amide (25 mg) at 25° C. in dioxane (1 mL) was added Burgess reagent (8 mg) and 4 Å powdered molecular sieves. The solution was aged for 2 h and then heated to 50° C. for 2 h. The solution was cooled to 25° C. and additional Burgess reagent (8 mg) was added. The solution was warmed to 50° C. for 4 h, then cooled to 0° C. and additional Burgess reagent (8 mg) was added and the solution was aged at 0° C. for 12 h. The solution was then heated to 50° C. for 4.5 h and again cooled to 25° C. The sieves were removed by filtration and the solution was concentrated to dryness under reduced pressure. Pure 7,24-bis-O-triethylsilyl protected title product (18 mg) was obtained following PTLC (1×1000 μm silica gel plate) using 2/8 acetone/hexanes as eluant. The product was characterized by $^1$H NMR.

Title compound is obtained following removal of the triethylsilyl protecting group per Example 4.

EXAMPLES 28a–28z

Following the general procedure of Example 28, the appropriate 3"-amides were converted into the corresponding 2"-oxazolines and deprotected as described in Example 4 to provide the following compounds:

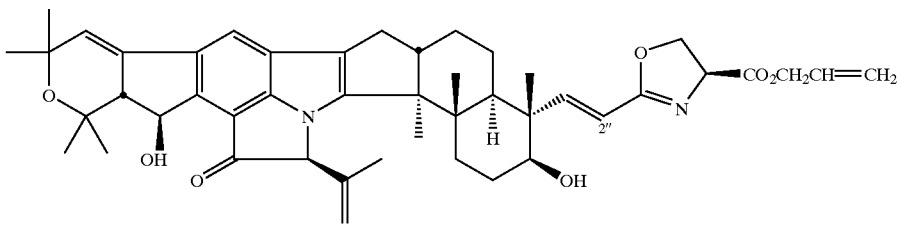

| Ex | R$_{1a}$ Group | R$_2$ Group | Mass Spec |
|---|---|---|---|
| 28a | H | H | 665.0 (M$^+$ + 1) |
| 28b | H | R—Me | 679.0 (M$^+$ + 1) |
| 28c | H | S—Me | 679.0 (M$^+$ + 1) |
| 28d | D-CH$_2$Ph | H | 755.0 (M$^+$ + 1) |
| 28e | L-CH$_2$Ph | H | 755.0 (M$^+$ + 1) |
| 28f | D-Me | H | 679.0 (M$^+$ + 1) |
| 28g | L-Me | H | 679.0 (M$^+$ + 1) |
| 28h | D-iPr | H | 707.0 (M$^+$ + 1) |
| 28i | L-iPr | H | 707.0 (M$^+$ + 1) |
| 28j | D-Ph | H | 741.0 (M$^+$ + 1) |
| 28k | L-Ph | H | 741.0 (M$^+$ + 1) |
| 28l | CO$_2$CH$_2$CH=CH$_2$ | Me | |
| 28m | D-CO$_2$CH$_2$Ph | H | 799.0 (M$^+$ + 1) |
| 28n | D-CO$_2$Et | H | 737.0 (M$^+$ + 1) |
| 28o | D-CO$_2$Me | H | 723.0 (M$^+$ + 1) |

-continued

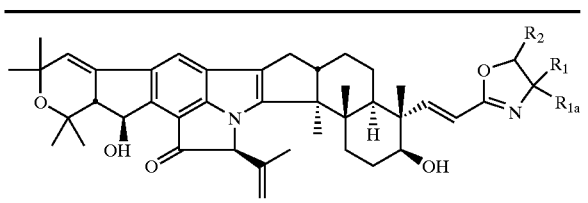

| Ex | $R_{1a}$ Group | $R_2$ Group | Mass Spec |
|---|---|---|---|
| 28p | C(O)NHCH$_2$C(Me)=CH$_2$ | H | |
| 28q | D-C(O)NH—Me | H | 722.0 (M$^+$ + 1) |
| 28r | D-C(O)NH—Et | H | 736.0 (M$^+$ + 1) |
| 28s | L-C(O)NH—Et | H | 736.0 (M$^+$ + 1) |
| 28t | D-C(O)NH-tBu | H | 764.0 (M$^+$ + 1) |
| 28u | D-C(O)NMe$_2$ | H | 736.0 (M$^+$ + 1) |
| 28v | L-C(O)NMe$_2$ | H | 736.0 (M$^+$ + 1) |
| 28w | $R_1$ + $R_2$ complete cyclohexyl, Isomer A | | 719.0 (M$^+$ + 1) |
| 28x | $R_1$ + $R_2$ complete cyclohexyl, Isomer B | | 719.0 (M$^+$ + 1) |
| 28y | $R_1$ = $R_{1a}$ = Me | H | 693.0 (M$^+$ + 1) |
| 28z | $R_1$ + $R_{1a}$ complete cyclopentyl | H | 719.0 (M$^+$ + 1) |

***$R_{1a}$ is H unless otherwise specified

EXAMPLE 29

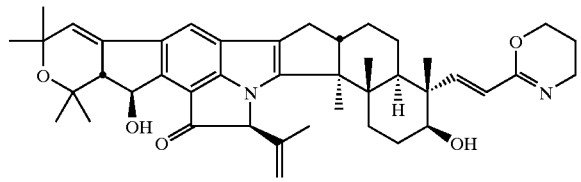

The 7,24-bis-OSiEt$_3$ protected compound 5z was cyclized as described in Example 28 and deprotected as described in Example 4 to generate the desired 2"-oxazine product which was characterized by $^1$H NMR and MS [m/z: 679.0 (M$^+$+1)].

EXAMPLE 30

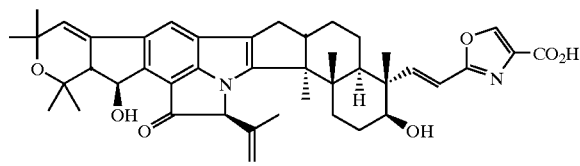

Step A. To 7,24-bis-O-triethylsilyl protected compound of Example 28 (17 mg) in CH2Cl2 (0.3 mL) at 0° C. was added BrCCl3 (3 μL) followed by DBU (3.6 μL) and aged for 12 h. The solution was poured into saturated NaHCO3(aq), extracted with CH2Cl2 and dried (Na2SO4). The solution was filtered, concentrated under reduced pressure and pure product was obtained following PTLC on silica gel (1×500 μm plate) using 25/75 acetone/hexanes as eluant to provide the corresponding 2"-oxazole compound (12.5 mg) which was characterized by 1H NMR.

Step B. To product of Step A (56 mg) in methylene chloride (3 mL) at 0° C. was added Pd(II)Cl2(PPh3)2 (1.2 mg) followed by nBu3SnH (22 μL). After 15 min, saturated NH4Cl(aq) was added and the solution was extracted with CH2Cl2 (3×). The organic extracts were dried, filtered and concentrated under reduced pressure. Flash chromatography on silica gel using gradient elution (1/1 EtOAc/hexanes, then 100% EtOAc, then 100% acetone, then 1/9 EtOH/CHCl3) gave pure 7,24-bis-O-triethylsilyl protected title compound (41 mg) was obtained following which was characterized by 1H NMR.

The title compound is obtained by removal of the triethylsilyl protecting groups in accordance with the general procedure described in Example 4.

EXAMPLES 30a–30j

The following compounds were prepared following the procedure described in Example 30, Step A and the deprotection procedure described in Example 4:

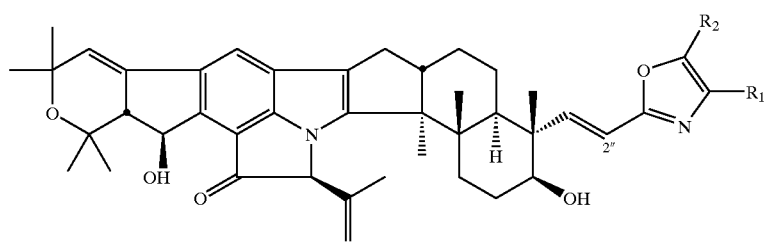

| Ex | $R_1$ Group | $R_2$ Group | Mass Spec |
|---|---|---|---|
| 30a | H | H | 663.0(M$^+$ + 1) |
| 30b | H | Me | 677.0(M$^+$ + 1) |
| 30c | H(1", 2"-dihydro) | Me | 679.0(M$^+$ + 1) |
| 30d | Me | H | 677.0(M$^+$ + 1) |
| 30e | iPr | H | 705.0(M$^+$ + 1) |
| 30f | Ph | H | — |
| 30g | CH$_2$Ph | H | 753.0(M$^+$ + 1) |
| 30h | C(O)NHCH$_2$C(Me)=CH$_2$ | H | 760.0(M$^+$ + 1) |
| 30i | CO$_2$CH$_2$CH=CH$_2$ | H | 747.0(M$^+$ + 1) |
| 30j | CO$_2$CH$_2$CH=CH$_2$ | Me | 761.0(M$^+$ + 1) |

EXAMPLE 31

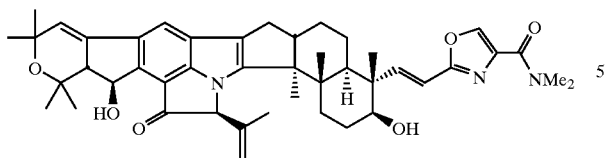

EXAMPLE 32

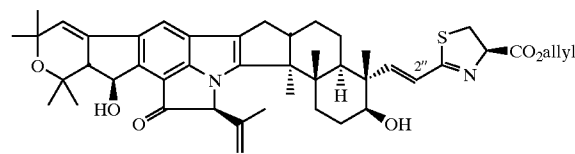

To the 7,24-bis-O-triethylsilyl protected compound of Example 30 (10 mg) in CH2Cl2 (0.3 mL) at 0° C. was added sequentially HOBT (2.9 mg), Me2NH (0.53 mL, 2M solution in THF) and BOP (5.5 mg). The solution was warmed to room temperature and aged for 2 h. The volatiles were removed under reduced pressure and pure product was obtained without workup following PTLC on silica gel (1×250 μm plate) using 35/65 EtOAc/hexanes as eluant to give 7,24-bis-OTES protected title compound (10 mg) which was characterized by $^1$H NMR.

Pure title product was deprotected as per Example 4 and the product was characterized by $^1$H NMR and MS [m/z: 734.0 (M$^+$+1)].

EXAMPLES 31a–31x

Following the general procedure of Examples 31, the following deprotected 2"-oxazoles were prepared:

The 3"-amide of L-Cys(Oallyl) was prepared following the general description of Example 5. To this 3"-amide (50 mg) and pyridine (44 μL) in CH$_2$Cl$_2$ (0.25 mL) at −50° C. was added neat (CF3SO2)2O(13 μL) dropwise down the side of the flask to pre-cool it. After the addition was complete, the solution was stirred at −78° C. for 10 min, then allowed to warm to 0° C. in an ice bath. The solution was aged for 7.5 h at 0° C. and L-cysteine ally ester (26 mg) in CH2Cl2 (0.1 mL) was added. The solution was allowed to warm to room temperature and was aged overnight. The solution was poured into saturated NaHCO3(aq), extracted with CH2Cl2 and dried (Na2SO4). The solution was filtered, concentrated under reduced pressure and pure 7,24-bis-O-triethylsilyl protected title compound was obtained following PTLC on silica gel (1×1000 μm plate) using 3/7 acetone/hexanes as eluant. The pure product thus obtained was characterized by 1H NMR.

The triethylsilyl protecting group was removed according to procedure described in Example 4 and the title compound was characterized by $^1$H NMR and MS [m/z: 765.0 (M$^+$+1)].

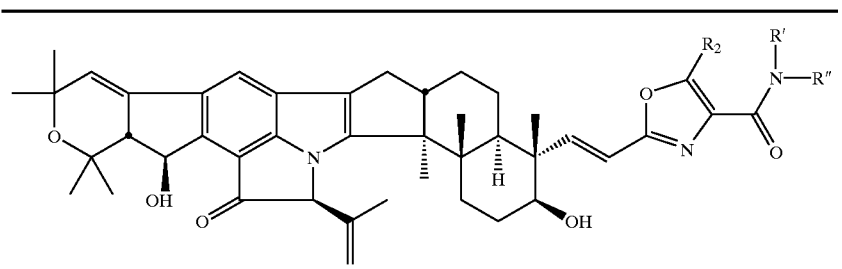

| Ex  | R'/R" Group              | R$_2$ Group | Mass Spec        |
|-----|--------------------------|-------------|------------------|
| 31a | NR'R" = 1-piperidinyl    | H           | 774.0(M$^+$ + 1) |
| 31b | NR'R" = 1-pyrrolidinyl   | H           | 760.4(M$^+$ + 1) |
| 31c | NR'R" = 4-morpholinyl    | H           | 776.0(M$^+$ + 1) |
| 31d | Et/iPr                   | H           | 776.0(M$^+$ + 1) |
| 31e | Me/Et                    | H           | 748.0(M$^+$ + 1) |
| 31f | Me/Et                    | H           | 762.0(M$^+$ + 1) |
| 31g | Me/iPr                   | H           | 762.0(M$^+$ + 1) |
| 31h | Et/Et                    | H           | 762.0(M$^+$ + 1) |
| 31i | H/cC$_3$H$_5$            | H           | 746.0(M$^+$ + 1) |
| 31j | H/Et                     | H           | 734.0(M$^+$ + 1) |
| 31k | H/iPr                    | H           | 748.0(M$^+$ + 1) |
| 31l | H/Me                     | H           | 720.0(M$^+$ + 1) |
| 31m | H/tBu                    | H           | 762.0(M$^+$ + 1) |
| 31n | H/H                      | H           | 706.0(M$^+$ + 1) |
| 31o | H/H                      | Me          | 721.0(M$^+$ + 1) |
| 31p | H/C(Me)$_2$C(O)NMe$_2$   | H           |                  |
| 31q | H/C(Me)$_2$C≡CH          | H           | 772.0(M$^+$ + 1) |
| 31r | H/CH$_2$CF$_3$           | H           | 788.0(M$^+$ + 1) |
| 31s | H/CH$_2$CH$_2$F          | H           | 752.0(M$^+$ + 1) |
| 31t | H/CH$_2$CH$_2$F          | Me          | 766.0(M$^+$ + 1) |
| 31u | H/CH$_2$CN               | H           | 669.0(M − 75)    |
| 31v | H/CH$_2$Ph(4-OMe)        | H           | 826.0(M$^+$ + 1) |
| 31w | Me/Me                    | H           | 734.0(M$^+$ + 1) |
| 31x | Me/Me (2'-epi/2'-nat, 1:1) | H         | 734.0(M$^+$ + 1) |

EXAMPLES 32a–32d

Following the general procedure of Example 32, the following deprotected 2″-thiazolines were prepared

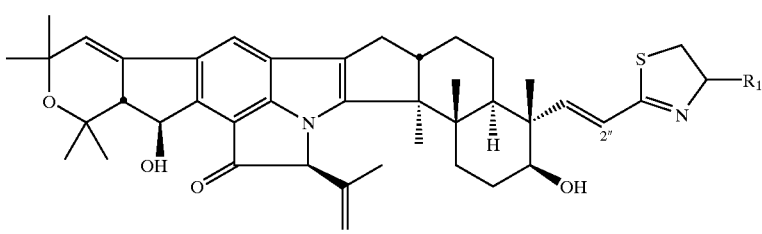

| Entry | $R_1$ | Mass Spec |
|---|---|---|
| 32a | H | 681.0($M^+$ + 1) |
| 32b | D—$CO_2$Me | 739.0($M^+$ + 1) |
| 32c | D—$CO_2$Et | 753.0($M^+$ + 1) |
| 32d | D—$CO_2CH_2CH=CH_2$ | 765.0($M^+$ + 1) |

EXAMPLE 33

Following the general procedure described in Example 30, Step B, the thiazoline-carboxylic acid allyl ester was converted to the corresponding thiazoline-carboxylic acid. The following amides were prepared using the resultant thiazoline-carboxylic acid and the appropriate amines following the general procedure described in Examples 3-5.

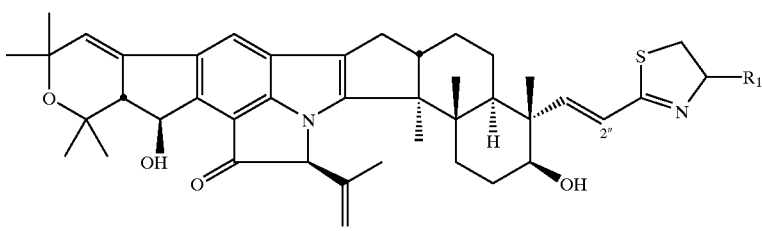

| Ex | $R_1$ Group | Mass Spec |
|---|---|---|
| 33a | D—C(O)NH—cPr | 764.0($M^+$ + 1) |
| 33b | D—C(O)NH—Et | 752.0($M^+$ + 1) |
| 33c | C(O)NHCH$_2$CH$_2$F | 770.0($M^+$ + 1) |
| 33d | C(O)NMe$_2$ | 752.0($M^+$ + 1) |

EXAMPLE 34

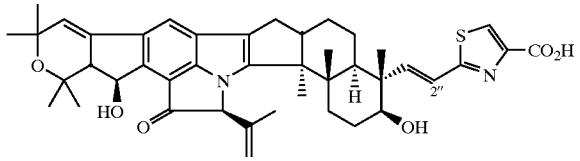

Following the procedures described in Example 30 using compound of Example 32d, the title compound was obtained, which was characterized by proton NMR and MS [m/z 763.0 (M⁺+1)].

EXAMPLES 35a–35m

Following the general procedure of Example 31 using the thiazole-carboxylic acid of Example 34 and an appropriate amine, the following 2"-thiazoles amides were prepared:

mg polar product B) thus obtained were characterized by $^1$H NMR.

EXAMPLES 35a–35j

The general procedure described in Example 35 was followed to provide the following compounds:

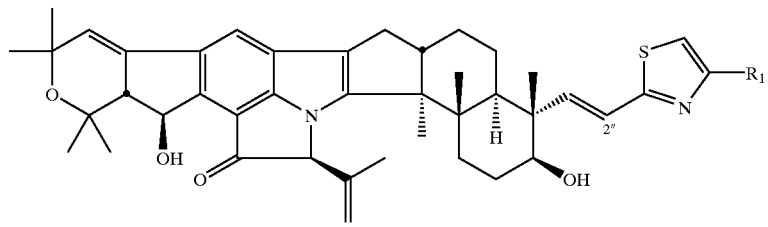

| Ex | R₁ | Mass Spec |
|---|---|---|
| 34a | C(O)NH—Et | 750.0(M⁺ + 1) |
| 34b | C(O)NH—Me | 736.0(M⁺ + 1) |
| 34c | C(O)NH—cPr | 762.0(M⁺ + 1) |
| 34d | C(O)NH—tBu | 778.0(M⁺ + 1) |
| 34e | C(O)NHC(Me)₂C≡CH | 788.0(M⁺ + 1) |
| 34f | C(O)(N-1-piperidinyl) | 790.0(M⁺ + 1) |
| 34g | C(O)(N-4-morpholinyl) | 792.0(M⁺ + 1) |
| 34h | C(O)N—Me₂ | 750.0(M⁺ + 1) |
| 34i | C(O)N(Me)Et | 764.0(M⁺ + 1) |
| 34j | C(O)N(Me)iPr | 778.0(M⁺ + 1) |
| 34k | C(O)N(Me)nPr | 778.0(M⁺ + 1) |
| 34l | C(O)N—Et₂ | 778.0(M⁺ + 1) |
| 34m | C(O)N(Et)iPr | 792.0(M⁺ + 1) |

EXAMPLE 35

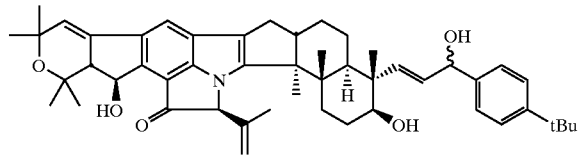

To Intermediate I (9.8 mg) in THF (0.2 mL) at −78° C. was added (4-tBu)PhMgBr (75 µL, 2M solution in THF). The solution was stirred for 10 min, then quenched by addition of saturated NH₄Cl(aq), diluted with water, extracted with EtOAc and dried (Na₂SO₄). The solution was filtered, concentrated under reduced pressure and pure product was obtained following PTLC on silica gel (1×500 µm plate) using 1/1 hexanes/EtOAc as eluant. The two diastereotopic 3"-alcohols (yield: 2 mg mobile product A and 3.2

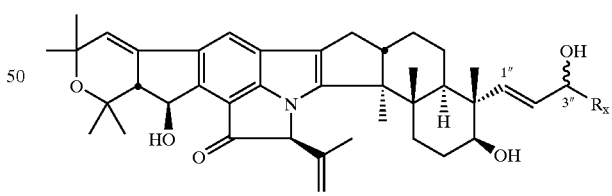

| Ex | Rˣ Group | Stereochem. |
|---|---|---|
| 35a | Me | A & B |
| 35b | iPr | Isomer A |
| 35c | iPr | Isomer B |
| 35d | nBu | Isomer A |
| 35e | nBu | Isomer B |
| 35f | Ph(4-F) | Isomer A |
| 35g | Ph(4-F) | Isomer B |
| 35h | CH₂C(O)Ph(4-Br) | A |
| 35i | CH₂C(O)Ph(4-Br) | B |
| 35j | CH₂CO₂Et | A & B |

EXAMPLE 36

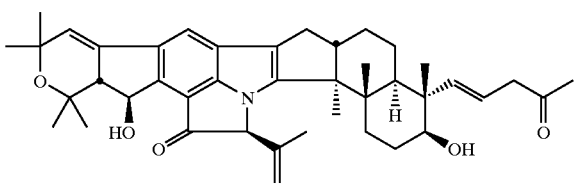

Nodulisporic acid A was converted into the 4"-vinyl isocyanate as per Example 26, Steps A and B. To the 4"-vinyl isocyanate (100 mg) thus prepared in MeOH (3 mL) at room temperature was added 6N HCl (0.5 mL). The solution was aged for 30 min, poured into saturated NaHCO$_3$(aq), extracted with EtOAc and dried (Na$_2$SO$_4$). The solution was filtered, concentrated under reduced pressure and pure product (78.4 mg) was obtained following PTLC on silica gel (2×1000 μm plates) using 3/2 hexanes/ EtOAc as eluant. The product thus obtained was characterized by $^1$H NMR and MS [m/z: 685.5 (M+NH$_4$)].

EXAMPLES 37a–37c

Following the general procedures of Example 26, Steps A and B and Example 36 and using Intermediates VIIIa, VIIIb, and VIIIc, the following 4"-ketones were prepared.

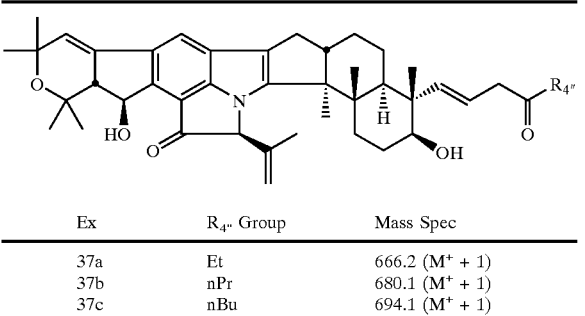

| Ex | R$_{4''}$ Group | Mass Spec |
|---|---|---|
| 37a | Et | 666.2 (M$^+$ + 1) |
| 37b | nPr | 680.1 (M$^+$ + 1) |
| 37c | nBu | 694.1 (M$^+$ + 1) |

EXAMPLE 38

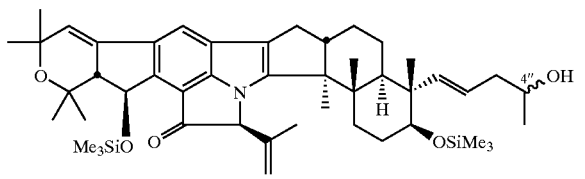

The 4"-methyl ketone prepared in Example 36 was bis-protected as per the general description for Intermediate II. To the 7,24-bis-O-trimethylsilyl-4"-ketone (200 mg) thus obtained in THF under argon atmosphere at −78° C. was added L-Selectride (251 μL). The solution was aged for 25 min, quenched with saturated NH$_4$Cl(aq) (2 mL), extracted with EtOAc and dried (Na$_2$SO$_4$). The solution was filtered and concentrated under reduced pressure. Pure 7,24-bis-O-trimethylsilyl-4"-alcohol (170 mg) was obtained following PTLC (2×1000 μm silica gel plates) using 4/1 hexanes/ EtOAc as eluant. The pure product was characterized by $^1$H NMR.

EXAMPLES 39a–39i

Following the general procedures of Examples 10–11 the following compounds were prepared and characterized by mass spectrometry and/or proton NMR:

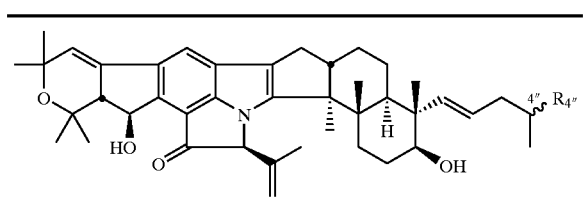

| Entry | R$_1$ Group | 4" Isomer | Mass Spec |
|---|---|---|---|
| 39a | OH | A & B | |
| 39b | O$_2$CPh | A & B | 1532 (2M$^+$ + NH$_4$) |
| 39c | OAc | A & B | |
| 39d | O$_2$C-tBu | A & B | 738.0 (M$^+$ + 1) |
| 39e | O$_2$C—Et | A & B | 692.1 (M$^+$ + 1-H$_2$O) |
| 39f | O$_2$C-iPr | A & B | 648.5 (M$^+$ − 75) |
| 39g | O$_2$C-nPr | A & B | |
| 39h | O$_2$CNHCH$_2$Ph | A & B | 769.5 (M$^+$ + 1-H$_2$O) |
| 39i | O$_2$CNH—Et | A & B | |

EXAMPLE 40

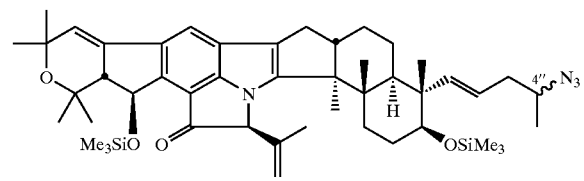

To the bis-protected-4"-alcohol (523 mg) product of Example 38 in THF (13 mL) at 0° C. under an atmosphere of argon was added PPh$_3$ (345 mg) followed by diethyl azodicarboxylate (245 μL) and diphenylphosphoryl azide (570 μL). The solution was aged at 0° C. for 40 min. The solvent was then removed under reduced pressure. The residue was filtered through a short pad of silica gel to remove baseline contaminants using 1/1 hexanes/EtOAc as eluant. By TLC, it was apparent that the product azide was partially deprotected so the entire crude was dissolved in acetonitrile (7.5 mL) at 25° C. to which was added HN(SIMe$_3$)$_2$ (2 mL) and aged for 2 h. The volatiles were removed under reduced pressure and pure 4"-azide (400 mg) was obtained following PTLC (5×1000 μm silica gel plates) using 9/1 hexanes/EtOAc as eluant. The product was characterized by $^1$H NMR.

EXAMPLE 41

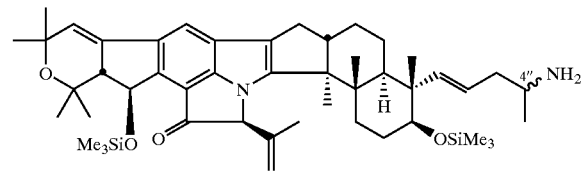

To the 4"-azide product of Example 40 (392 mg) in THF (7.7 mL) at 25° C. was added PPh$_3$ (150 mg) followed by water (160 μL). The solution was aged for 12 h and then the volatiles were removed under reduced pressure. Pure 4"-amine (168 mg) was obtained following PTLC (3×1000 μm silica gel plates) using 9/1 CH$_2$Cl$_2$/MeOH as eluant. The product was characterized by $^1$H NMR.

EXAMPLE 42

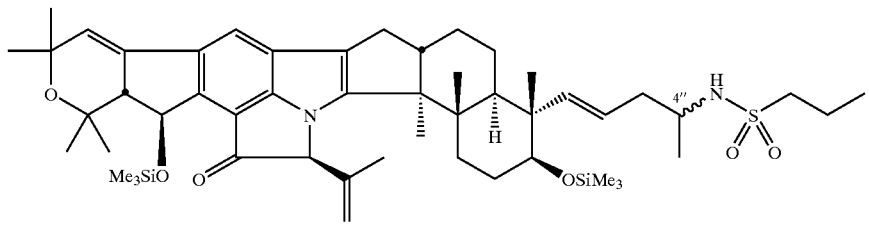

To the 4"-amine (35 mg) at 0° C. in CH$_2$Cl$_2$ (0.8 mL) was added triethylamine (75 μL) followed by 1-propylsulfonyl chloride (50 μL). After 15 min at 0° C., the crude was purified directly without workup by PTLC (1×1000 μm silica gel plate) using 2/1 hexanes/acetone as eluant. Pure 4"-n-propylsulfonamide (24 mg) was characterized by $^1$H NMR.

EXAMPLES 43A–43Z

Following the general procedures of Examples 10–11 the following compounds were prepared and characterized by mass spectrometry and/or proton NMR:

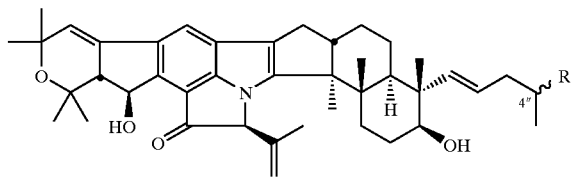

| Entry | R$_1$ Group | 4" Isomer | Mass Spec |
|---|---|---|---|
| 43a | N$_3$ | Is. A & B | 603.4 (M$^+$ − 75) |
| 43b | NHAc | Is. A & B | 695.1 (M$^+$ + 1) |
| 43c | NHC(O)Ph(4-Cl) | Is. A & B | 715.4 (M$^+$ − 75) |
| 43d | NHC(O)nBu | Is. A & B | 661.5 (M$^+$ − 75) |
| 43e | NHC(O)Et | Is. A & B | 631.5 (M$^+$ − 75) |
| 43f | NHC(O)Et | Is. A | 709.1 (M$^+$ + 1) |
| 43g | NHC(O)Et | Is. B | 709.2 (M$^+$ + 1) |
| 43h | NHC(O)nPr | Is. A | |
| 43I | NHC(O)nPr | Is. B | |
| 43j | NHC(O)tBu | Is. A & B | 737.2 (M$^+$ + 1) |
| 43k | NHC(O)iPr | Is. A & B | 723.3 (M$^+$ + 1) |
| 43l | NHC(O)(4-pyridyl) | Is. A & B | 758.3 (M$^+$ + 1) |
| 43m | NHC(O)NH-iPr | Is. A & B | 770.3 (M$^+$ + 1) |
| 43n | NHC(O)NH-tBu | Is. A & B | 752.3 (M$^+$ + 1) |
| 43o | NHC(O)NH—(Ph(4-F)) | Is. A & B | 790.2 (M$^+$ + 1) |
| 43p | NHC(O)NH-nPr | Is. A & B | 738.3 (M$^+$ + 1) |
| 43q | NHC(O)NHCH$_2$CH$_2$(2-thienyl) | Is. A & B | 806.3 (M$^+$ + 1) |
| 43r | NHSO$_2$Me | Is. A & B | 655.4 (M$^+$ − 75) |
| 43s | NHSO$_2$CH$_2$Ph | Is. A & B | 731.5 (M$^+$ − 75) |
| 43t | NHSO$_2$nPr | Is. A & B | 683.5 (M$^+$ − 75) |
| 43u | NHSO$_2$(2-thienyl) | Is. A & B | 781.3 (M$^+$ + 1-H$_2$O) |

EXAMPLE 44

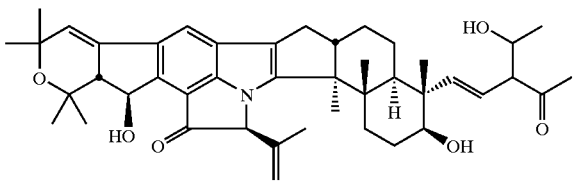

The product of Example 36 was bis-protected as per Intermediate II. To bis-protected-4"-methyl ketone (50 mg) thus obtained in THF (1.4 mL) at −78° C. was added LiN(SiMe$_3$)$_2$ (68 μL, 1M solution in THF) under at atmosphere of argon. The solution was aged for 15 min and then acetaldehyde (100 μL) was added dropwise. After 30 min at −78° C., saturated NH$_4$Cl(aq) was added, the solution was extracted with EtOAc, the organic layer was washed with water and dried (Na$_2$SO$_4$). The solution was filtered and the volatiles removed under reduced pressure. The silyl protecting groups were removed as per Example 4 to yield two diastereomeric products following PTLC on silica gel (2×500 μm plates) using 2/1 hexanes/acetone as eluant. Mobile product A (19.1 mg) and polar product B (14.5 mg) were characterized by $^1$H NMR and MS [m/z: 620.3 (M−75) for each].

EXAMPLES 45a–45w

Following the general procedures of Examples 44 using the appropriate electrophile, the following compounds were prepared:

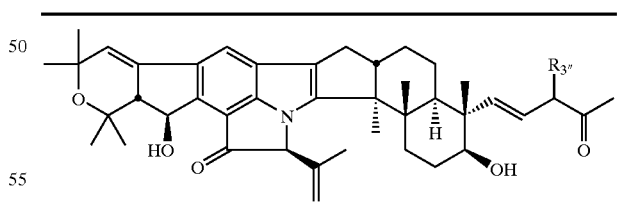

| Ex | R$_{3"}$ Group | Mass Spec |
|---|---|---|
| 45a | (CH$_2$CN)$_2$ | 730.4 (M$^+$ + 1) |
| 45b | CH(OH)(2-(3-Cl-5-CF$_3$-pyridyl)) | 861.1 (M$^+$ + 1) |
| 45c | CH(OH)(3-(N—Me-4-Cl-pyrazolyl)), Isomer A | 796.0 (M$^+$ + 1) |
| 45d | CH(OH)(3-(N—Me-4-Cl-pyrazolyl)), Isomer B | 796.0 (M$^+$ + 1) |
| 45e | CH(OH)(3-furyl) | 704.4 (M − 75) |
| 45f | CH(OH)(4-(3-CF$_3$-5-Cl—N—Me-pyrazolyl)) | 788.4 (M − 75) |
| 45g | CH(OH)Me, Isomer A | 620.3 (M − 75) |
| 45h | CH(OH)Me, Isomer B | 620.3 (M − 75) |
| 45i | CH(OH)Ph, Isomer A | 682.3 (M − 75) |
| 45j | CH(OH)Ph, Isomer B | 682.3 (M − 75) |

-continued

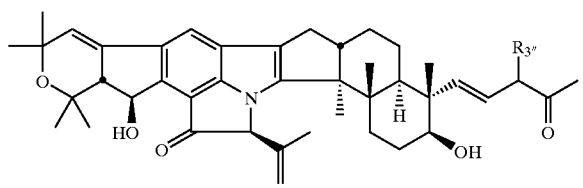

| Ex | R₃″ Group | Mass Spec |
|---|---|---|
| 45k | CH₂CH=C(Me)₂, Isomer A | 644.5 (M − 75) |
| 45l | CH₂CH=C(Me)₂, Isomer B | 644.5 (M − 75) |
| 45m | CH₂CH=CH₂, Isomer A | 616.9 (M − 75) |
| 45n | CH₂CH=CH₂, Isomer B | 616.4 (M − 75) |
| 45o | CH₂CN | 615.2 (M − 75) |
| 45p | CH₂CO₂-tBu, Isomer A | 690.3 (M − 75) |
| 45q | CH₂CO₂-tBu, Isomer B | 690.3 (M − 75) |
| 45r | CH₂CO₂CH₂CH=CH₂ | |
| 45s | CH₂CO₂H | |
| 45t | CH₂Ph | |
| 45u | F | |
| 45v | Me(2′-epi/2′-nat) | |
| 45w | Me | |

EXAMPLE 46

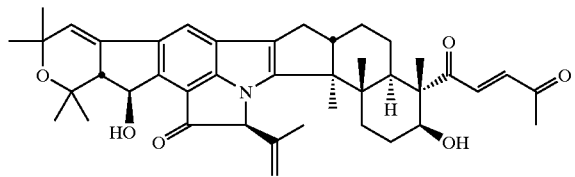

Nodulisporic Acid A was converted into the 4″-isocyanate as per Examples 26, steps A and B. To the 4″-isocyanate (1.2 g) thus prepared in acetone/water (9/1, 70 mL) was added silica gel (7 g) and the solution heated to 65° C. for 80 min. The solids were removed by filtration and the volatiles removed under reduced pressure. Partially purified product was obtained by flash chromatography using gradient elution using hexanes/acetone (3/1→7/3→1/1). The polar band was collected (fractions 5–8) and concentrated to dryness under reduced pressure. This residue (~70 mg) was repurified by PTLC on silica gel (3×500 μm plates) using hexanes/acetone (3/1, two developments) to yield two products with very similar TLC mobility: Intermediate I (29 mg) and the title product (18 mg). The purified title product was characterized by ¹H NMR.

EXAMPLE 47

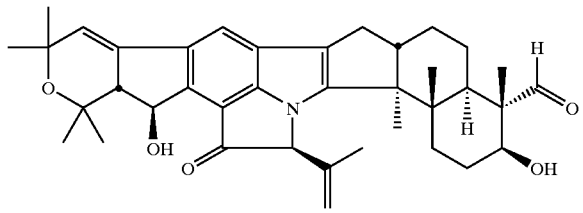

To a well stirred mixture of KMnO₄ (10 mg), Al₂O₃ (weakly acidic) (50 mg) and water (10 μL) was added a solution of compound of Example 2 (10 mg) in CH₂Cl₂ (1 mL) at room temperature. The mixture was stirred for 2 h and then filtered though a pad of Celite. The residue was washed with CH₂Cl₂ (10 ml), and the combined filtrate was concentrated in vacuo. The crude material, thus obtained, was purified by preparative thin-layer chromatography using EtOAc/Hexane (1/1) as the eluent. Yield: 2.5 mg (25%), ¹H NMR (400 MHz): consistent with the desired structure; MS: m/e 598.5 (M+H) and 522.5 (M−75).

EXAMPLE 48

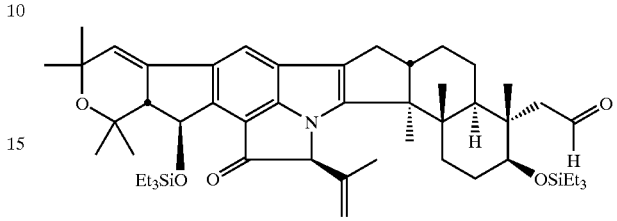

To compound of Example 26, Step B (140 mg) in dioxane/water (9/1, 8 mL) at room temperature was added PPTS (20 mg) and the solution aged for 4 h. The solution was poured into saturated NaHCO₃(aq), extracted with CH₂Cl₂, washed with brine and dried (Na₂SO₄). The solution was filtered and concentrated under reduced pressure. Pure product (70 mg) was obtained following chromatotron purification (2 mm plate) using gradient elution (hexanes to 2/8 EtOAc/hexanes). The product thus obtained was characterized by ¹H NMR.

EXAMPLE 49

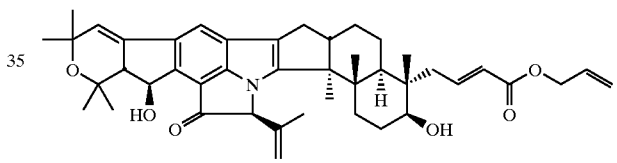

To the 7,24-bis-OSiEt₃-protected-2″-aldehyde (Example 48, 56 mg) in toluene (3.5 mL) at room temperature was added Ph₃P=CHCO₂CH₂CH=CH₂ (36 mg) and the solution was heated to reflux for 5.5 h and then aged at room temperature for 48 h. The volatiles were removed under reduced pressure and pure bis-protected product (55 mg, 90%) was obtained following PTLC on silica gel (1×1500 μm plate) using 1/9 EtOAc/hexanes as eluant. The product was characterized by ¹H NMR. The TES protecting groups were removed as per Example 4 to give the pure title compound was characterized by ¹H NMR and MS [m/z: 1404 (2M+NH₄)].

EXAMPLE 50

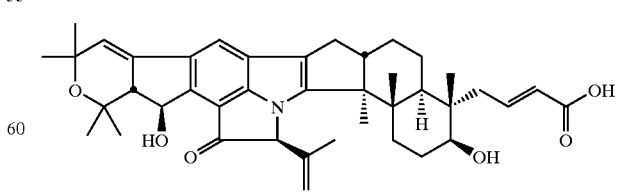

The title compound was obtained from the compound of Example 49 following the general deprotection procedure described for Example 30, step B.

EXAMPLE 51a–51i

Following the general procedure described in Example 49, the following compounds were prepared.

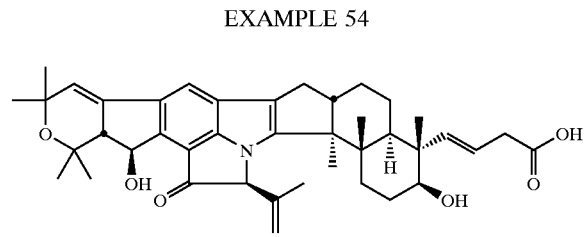

| Ex | $R_{4''}$ Group | Mass Spec |
|---|---|---|
| 51a | Me | 1320 (2M$^+$ + NH$_4$) |
| 51b | NH-cC$_3$H$_5$ | 693.0 (M$^+$ + 1) |
| 51c | NH—Et | 681.0 (M$^+$ + 1) |
| 51d | NH—Me | 667.0 (M$^+$ + 1) |
| 51e | NHC(Me)$_2$C≡CH | 719.0 (M$^+$ + 1) |
| 51f | NHCH$_2$CH$_2$F | 699.0 (M$^+$ + 1) |
| 51g | NMe$_2$ | 681.0 (M$^+$ + 1) |
| 51h | OH | — |
| 51i | OMe | 1352 (2M$^+$ + NH$_4$) |

EXAMPLE 52

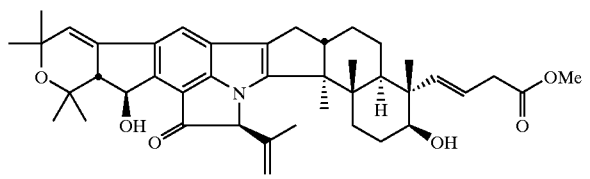

To a solution of Intermediate VII (126 mg crude weight, theoretical amount is 75 mg) in methanol (3 mL) at room temperature was added 2N HCl (0.2 mL) and aged for 7 h. The solution was poured into saturated NaHCO$_3$(aq), extracted with EtOAc, washed with brine and dried (Na$_2$SO$_4$). The solution was filtered and concentrated under reduced pressure to yield crude methyl ester (100 mg). Pure 4"-methyl ester was obtained following PTLC on silica gel (3×1000 μm plates) using 2/1 hexanes/acetone as eluant. Pure title product was characterized by $^1$H NMR and MS (m/z: 668.3 M$^+$+1)).

EXAMPLE 53

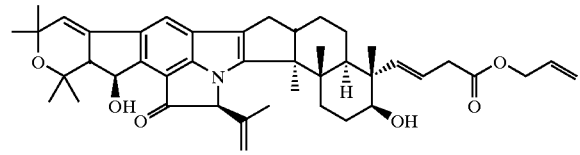

To the 4"-methyl ester product of Example 52 (40.5 mg) in allyl alcohol (2 mL) at room temperature was added Ti(OiPr)$_4$ (15 μL) and the solution was heated to 135° C. for 3.5 h. The solution was cooled to room temperature and the solvent removed under reduced pressure. The crude residue was filtered through a pad of silica gel using EtOAc as eluant and concencntrated to dryness. Proton NMR of the crude product indicated incomplete reaction so the material was redissolved in allyl alcohol (2 mL), Ti(OiPr)$_4$ (20 μL) was added and the solution was heated to 135° C. for 7 h and then aged at room temperature overnight. The solution was worked up as previously described. Pure 4"-allyl ester (27 mg) was obtained following PTLC on silica gel (2×500 μm plates) using 2/1 hexanes/acetone as eluant. The product thus obtained was characterized by $^1$H NMR.

EXAMPLE 54

To the 4"-allyl ester (Example 53, 43.9 mg) in CH$_2$Cl$_2$ (0.75 mL) and THF (0.25 mL) at room temperature was added morpholine (50 μL) followed by Pd(PPh$_3$)$_4$ (15 mg). After 30 min, the solution was poured into saturated NH$_4$Cl (aq) and water was added to the separatory funnel. The aqueous layer was extracted with CH$_2$Cl$_2$, dried (Na$_2$SO$_4$), filtered and concentrated to dryness under reduced pressure. Pure product (31.5 mg) was obtained following PTLC on silica gel (1×1000 μm plate) using 90/9/1CHCl$_3$/MeOH/AcOH as eluant and lyophilization from benzene. The 4"-carboxylic acid thus obtained was characterized by $^1$H NMR.

EXAMPLES 55a–55n

Following the general procedure of Example 3, using the carboxylic acid of Example 46 and the appropriate amines, the following compounds were prepared:

| Entry | R$^c$/R$^d$ Group | Mass Spec |
|---|---|---|
| 55a | H/(1-adamantyl) | |
| 55b | H/cC$_3$H$_5$ | |
| 55c | H/iBu | 709.5 (M$^+$ + 1) |
| 55d | H/tBu | |
| 55e | H/C(Me)$_2$C≡CH | |
| 55f | H/CH$_2$(2-furyl) | |
| 55g | H/CH$_2$C(Me)$_3$ | 723.5 (M$^+$ + 1) |
| 55h | H/CH$_2$CH$_2$CH$_3$ | |
| 55I | H/CH$_2$CH$_3$ | 664.2 (M$^+$ + 1) |
| 55j | H/CH$_2$Ph | 743.5 (M$^+$ + 1) |
| 55k | H/Ph | |
| 55l | Me/Me | |
| 55m | Et/Et | |
| 55n | NR'R" = 4-morpholinyl | |

EXAMPLE 56

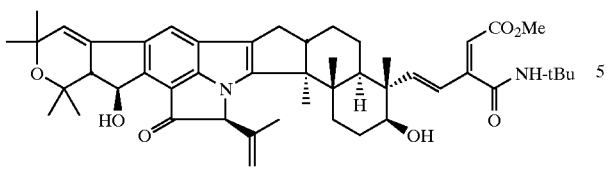

To compound of Example 25 (14.3 mg) in THF (0.4 mL) at room temperature was add Ph$_3$P=CHCO$_2$Me (7.2 mg). The solution was aged for 1 h and then heated to 45° C. for 3 h. The solution was cooled to room temperature and purified by PTLC on silica gel (2×500 μm plates) without workup using hexanes/EtOAc (1/1) as eluant. The pure product (2.2 mg) thus obtained was characterized by $^1$H NMR and MS [m/z: 780.4 (M$^+$+1)].

EXAMPLES 57a–57b

Following the general procedure of Example 56, the following compounds were prepared using the compound of Example 25 and the appropriate Wittig reagents as indicated below:

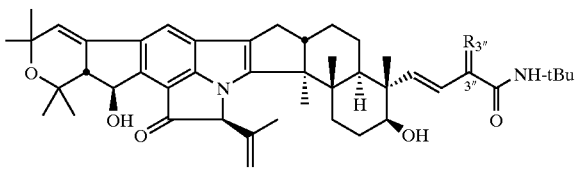

| Entry | Wittig Reagent | R$^{3''}$ Group |
|---|---|---|
| 57a | Ph$_3$P=CHOMe | CHOMe |
| 57b | Ph$_3$P=CH$_2$ | CH$_2$ |

EXAMPLE 58

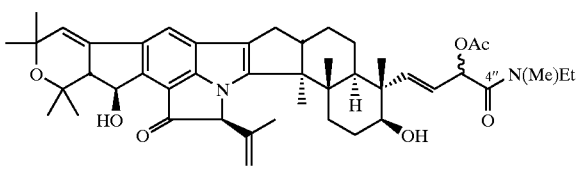

To a solution of the 4"-N-methyl amide product of Example 24a (40 mg) in dioxane (0.5 mL) at –60° C. add iBuONO (20 μL). Warm the solution slowly to –20° C., age for 30 min and recool to –60° C. Add a solution iPr$_2$NEt (20 μL) and HN(Me)Et (40 μL) in DMF (0.5 mL), warm to –20° C. and age for 12 h. Evaporate the solvent under reduced pressure and the pure 4"-N-methyl-N-ethyl amide may be obtained following PTLC on silica gel using acetone/hexanes as eluant. The product thus obtained may be characterized by $^1$H NMR and MS.

EXAMPLE 59

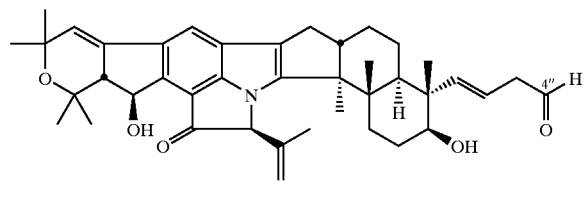

Following the general procedure of Example 3 for the preparation of 3"-amides, the 4"-carboxylic acid (product of Example 46) was converted into the corresponding 4"-thioester. The intermediate 4"-thioester (20 mg) was placed in acetone (3 mL) with Et$_3$SiH (100 mg) and 10% Pd/C at RT. After 2 h, the catalyst was removed by filteration and pure product was obtained following flash chromatography on silica gel. The 4"-aldehyde thus obtained was characterized by $^1$H NMR.

EXAMPLE 60

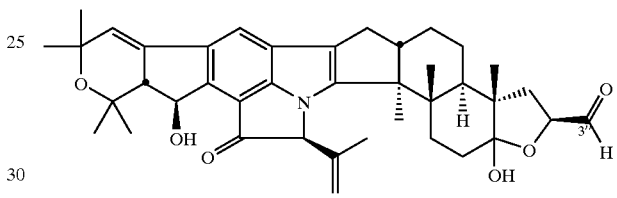

Nodulisporic acid A1 (Compound B) was converted into the corresponding 3"-aldehyde following the general procedure as described for Intermediate I. The product thus obtained was characterized by $^1$H NMR and MS [m/z: 654.2 (M$^+$+1)].

EXAMPLES 61a–61d

Following the general procedure described in previous examples, the following compounds were prepared using appropriate olefinating agents:

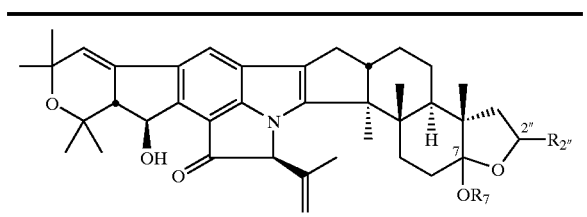

| Entry | R$_7$ Group | R$_{2''}$ Group | Mass Spec |
|---|---|---|---|
| 61a | Me | CH(OAc)C(O)NH-tBu (Isomer B at 3") | 797.3 (M$^+$ + 1) |
| 61b | Me | Me—HN (imidazopyridine) 3" | 771.4 (M$^+$ + 1) |
| 61c | H | CH(OAc)C(O)NH—Me (Isomers A and B at 3") | 741.5 (M$^+$ + 1) |

-continued

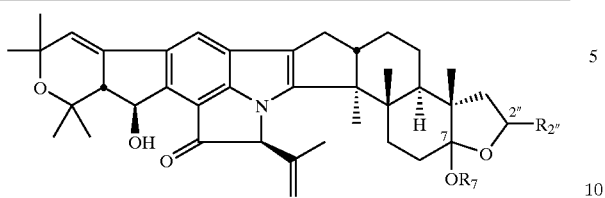

| Entry | R₇ Group | R₂„ Group | Mass Spec |
|---|---|---|---|
| 61d | H | CH(OAc)C(O)NH-tBu (Isomer A at 3") | 797.5 (M⁺ + 1) |

EXAMPLE 62

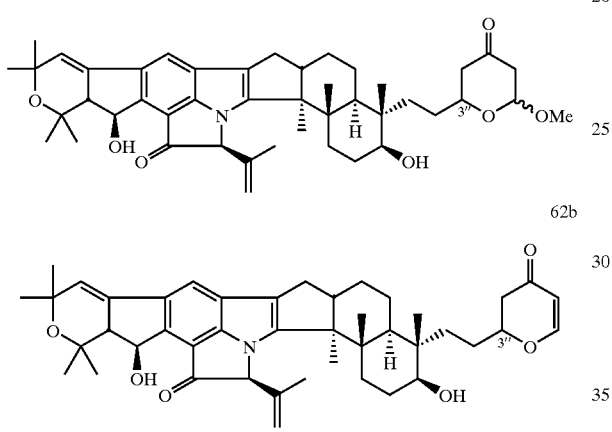

To the 7,24-bis-OSiMe₃-protected 1",2"-dihydro-3"-aldehyde (1",2"-dihydro-Intermediate II, 30 mg) in THF (0.8 μL) at rt was added 1-methoxy-3-trimethylsilyloxy-butadiene (50 μL) followed by ZnCl₂ (80 μL, 1M solution in Et₂O) After 2 h at rt and 12 h at 0° C., bis-protected Diels-Alder adducts were obtained without workup by PTLC on silica gel (1×1000 μm plate) using 2/8 acetone/hexanes as eluant. The pure products (7 mg methoxy-substituted pyranone and 10 mg pyrenone) thus obtained were characterized by ¹H NMR. Both products were deprotected separately as described previously (10 mg pyrenone yielded 9 mg deprotected product and 7 mg methoxypyranone yielded 6 mg deprotected product). The deprotected products were characterized by ¹H NMR.

What is claimed is:

1. A compound having the formula I:

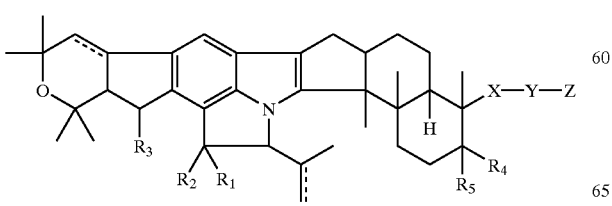

wherein

═══ represents a single or a double bond;

X—Y—Z is selected from the group:

(1) 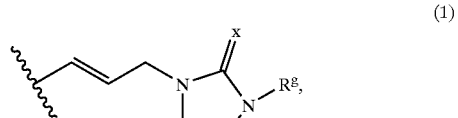

(2) 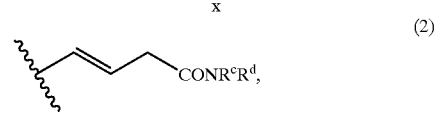

(3) 

(4) 

(5)  and (6) 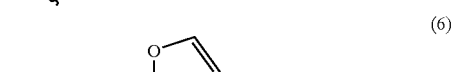 and each ring optionally substituted with 1 to 2 groups independently selected from C₁–C₄alkyl, phenyl, benzyl, CONR^cR^d and CO2R^b;

x is independently O or S;

the two R groups are independently H or C₁–C₅alkyl, or together complete a C₃–C₆ ring;

R₁ is (1) hydrogen,
  (2) optionally substituted C₁–C₁₀ alkyl,
  (3) optionally substituted C₂–C₁₀ alkenyl,
  (4) optionally substituted C₂–C₁₀ alkynyl,
  (5) optionally substituted C₃–C₈ cycloalkyl,
  (6) optionally substituted C₅–C₈ cycloalkenyl,
  (7) optionally substituted aryl,
  (8) 5- or 6-membered heterocycle containing from 1 to 4 heteroatoms independently selected from O, S and NR^c,
    where the substitutents on the alkyl, alkenyl, alkynyl are 1 to 3 groups selected from R', the substituents on aryl is 1 to 3 groups selected from R", and the substituents on cycloalkyl and cycloalkenyl are 1 to 3 groups independently selected from R", oxo and thiono;

R₂, R₃, and R₄ are independently OR^a, OCO₂R^b, OC(O)NR^cR^d; or

R₁+R₂ represent ═O, ═NOR^a, ═N—NR^cR^d, ═CR^aCO₂R^a, ═CR^aC(O)NR^cR^d, ═CR^aCN, ═CR^aC(O)R^a, or ═CR^aR^a;

$R_5$ is (1) hydrogen,
  (2) $OR^a$ or
$R_4+R_5$ represent =O, =$NOR^a$, =N—$NR^cR^d$ or =$CR^aR^a$;
$R^a$ is (1) H,
  (2) optionally substituted $C_1$–$C_{10}$ alkyl,
  (3) optionally substituted $C_3$–$C_{10}$ alkenyl,
  (4) optionally substituted $C_3$–$C_{10}$ alkynyl,
  (5) optionally substituted $C_3$–$C_{15}$ cycloalkyl,
  (6) optionally substituted $C_5$–$C_{10}$ cycloalkenyl,
  (7) optionally substituted aryl,
  (8) optionally substituted heteroaryl,
  (9) optionally substituted 3- to 10-membered heterocycle containing 1 to 4 heteroatoms selected from O, S and $NR^g$,
  (10) a benzene ring fused to a 4- to 8-membered heterocyclic ring with from 1 to 4 heteroatoms selected from oxygen, sulfur and $NR^g$,
  (11) a 4- or 8-membered heterocyclic ring with from 1 to 4 heteroatoms selected from O, S and $NR^g$ fused to a 4- or 8-membered heterocyclic ring with from 1 to 4 heteroatoms selected from O, S and $NR^g$, and
where the substituents on the aryl, alkyl, alkenyl, alkynyl groups are 1 to 10 groups selected from R'; the substituents on aryl, heteroaryl and benzene are 1 to 5 groups selected from R"; and the substituents on cycloalkyl, cycloalkenyl and heterocycle are 1 to 10 groups selected from R", oxo and thiono;
$R^b$ is (1) a group selected from $R^a$,
  (2) $C_2$–$C_6$ alkanoyl,
$R^c$ and $R^d$ are independently selected from $R^b$, hydroxy, $C_1$–$C_5$ alkoxy, $C_1$–$C_5$ alkoxycarbonyl, aminocarbonyl, $C_1$–$C_5$ alkylaminocarbonyl and $C_1$–$C_5$ dialkylaminocarbonyl; or
$R^c$ and $R^d$ together with the N to which they are both attached form a 3- to 10-membered ring containing 0 to 2 additional heteroatoms selected from O, $S(O)_m$, and $NR^g$, said ring is optionally substituted with 1 to 5 groups independently selected from R", thiono and oxo; said ring is further optionally fused to a benzene ring optionally substituted with 1 to 3 groups selected from $R^e$; said ring is further optionally spiro fused to a $C_3$–$C_7$ cycloalkyl ring;
$R^e$ is (1) halogen,
  (2) $C_1$–$C_7$ alkyl,
  (3) $C_1$–$C_3$ perfluoroalkyl,
  (4) $S(O)_mR^i$,
  (5) cyano,
  (6) nitro,
  (7) $R^iO(CH_2)_v$—,
  (8) $R^iCO_2(CH_2)_v$—,
  (9) $R^iOCO(CH_2)_v$,
  (10) optionally substituted aryl where the substituents are from 1 to 3 of halogen, $C_1$–$C_6$ alkyl, $C_1$–$C_6$ alkoxy, or hydroxy,
  (11) $SO_2NR^iR^i$, or
  (12) amino;
$R^f$ is (1) H,
  (2) $C_1$–$C_5$ alkyl optionally substituted with 1 to 5 groups selected from halogen, cyano, hydroxy, $C_1$–$C_3$ alkoxy, $NR^gR^h$, $CO_2R^i$ and $CONR^gR^h$,
  (3) $C_{2-6}$ alkenyl,
  (4) $C_{2-6}$ alkynyl,
  (5) $C_3$–$C_6$ cycloalkyl,
  (6) aryl optionally substituted with 1 to 4 groups independently selected from $R^e$, or 2 adjacent substituents together form methylenedioxy, or
  (7) aryl-$C_1$–$C_3$ alkyl optionally substituted with 1 to 4 groups independently selected from $R^e$, or 2 adjacent substituents together form methylenedioxy, or
two Rf groups together with the nitrogen atom to which they are attached form a a 3- to 10-membered ring containing 0 to 2 additional heteroatoms selected from O, $S(O)_m$, and $NR^g$, said ring is optionally substituted with 1 to 5 groups independently selected from R", thiono and oxo; said ring is further optionally fused to a benzene ring optionally substituted with 1 to 3 groups selected from $R^e$; said ring is further optionally spirofused to a $C_3$–$C_7$ cycloalkyl ring; $R^g$ and $R^h$ are independently
  (1) hydrogen,
  (2) $C_1$–$C_{10}$ alkyl optionally substituted with 1 to 10 groups selected from hydroxy, amino, $C(O)R^i$, and $CO_2R^i$,
  (3) aryl optionally substituted with 1 to 5 groups selected from halogen, amino, 1,2-methylenedioxy, $C_1$–$C_7$ alkoxy, $C_1$–$C_7$ alkyl and $C_1$–$C_3$ perfluoroalkyl,
  (4) aryl $C_1$–$C_6$ alkyl, wherein the aryl is optionally substituted with 1 to 5 groups selected from halogen, amino, 1,2-methylenedioxy, $C_1$–$C_7$ alkoxy, $C_1$–$C_7$ alkyl and $C_1$–$C_3$ perfluoroalkyl,
  (5) $C_3$–$C_7$ cycloalkyl optionally substituted with phenyl,
  (6) $C_1$–$C_5$ alkanoyl,
  (7) $C_1$–$C_5$ alkoxycarbonyl,
  (8) aryl $C_1$–$C_5$ alkoxycarbonyl,
  (9) aminocarbonyl,
  (10) $C_1$–$C_5$ monoalkylaminocarbonyl
  (11) $C_1$–$C_5$ dialkylaminocarbonyl; or
$R^g$ and $R^h$ together with the N to which they are attached form a 3- to 7-membered ring containing 0 to 2 additional heteroatoms selected from O, $S(O)_m$, and $NR^i$, optionally substituted with 1 to 3 groups independently selected from $R^e$ and oxo;
$R^i$ is (1) hydrogen,
  (2) $C_1$–$C_3$ perfluoroalkyl,
  (3) $C_1$–$C_6$ alkyl,
  (4) optionally substituted aryl or optionally substituted aryl $C_1$–$C_6$ alkyl, where the aryl substituents are from 1 to 3 groups independently selected from halogen, $C_1$–$C_6$ alkyl, $C_1$–$C_6$ alkoxy, and hydroxy;
$R^z$ is $OR^a$, $OC(O)R^a$, $OC(O)OR^b$, $OC(O)NR^cR^d$, $NR^cC(O)R^a$, $NR^cC(O)OR^a$, $NR^cC(O)NR^cR^d$, $NR^cSO_2R^a$;
R' is (1) halogen,
  (2) cyano,
  (3) nitro,
  (4) $C(O)R^f$,
  (5) $CO_2R^f$,
  (6) $C(O)NR^gR^h$,
  (7) $OR^f$,
  (8) $OC(O)R^f$,
  (9) $OC(O)NR^gR^h$,
  (10) $OC(O)OR^f$,
  (11) $SR^f$,
  (12) $S(O)_mR^f$,
  (13) $SO_2NR^gR^h$,
  (14) $NR^gR^h$,
  (15) $NR^gC(O)R^f$,
  (16) $NR^gCO_2R^f$,
  (17) $NR^gC(S)OR^f$,
  (18) $NR^gC(O)NR^gR^h$,

(19) $C_3$–$C_7$ cycloalkyl optionally substituted with 1 to 4 groups independently selected from $R^e$,
(20) $C_5$–$C_7$ cycloalkenyl optionally substituted with 1 to 4 groups independently selected from $R^e$,
(21) aryl optionally substituted with 1 to 4 groups independently selected from $R^e$, or 2 adjacent substituents together form methylenedioxy,
(22) heteroaryl optionally substituted with 1 to 4 groups independently selected from $R^e$,
(23) 5 to 9-membered heterocycle containing from 1 to 4 heteroatoms independently selected from O, S and $NR^g$, and optionally substituted with 1 to 4 groups independently selected from $R^e$, R' is (1) a group selected from R',
(2) $C_1$–$C_6$ alkyl, optionally substituted with halogen, aryl, $OR^f$ and $NR^gR^h$,
(3) $C_{2-6}$alkenyl,
(4) $C_{2-6}$alkynyl;

m is 0 to 2;
n is 0 or 1; and
v is 0 to 3; or
a pharmaceutically acceptable salt thereof.

2. A compound of claim 1 wherein X—Y—Z is

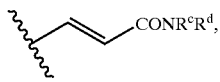

wherein one of $R^c$ and $R^d$ is H or $C_1$–$C_{10}$alkyl, and the other is $C_1$–$C_{10}$alkyl optionally substituted with 1–10 groups selected from halogen, $OR^f$, $CO_2R^f$, $CONR^gR^h$ and aryl, or $C_3$–$C_{10}$alkenyl.

3. A compound of claim 1 wherein X—Y—Z is

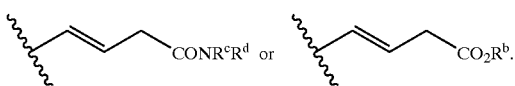

4. A compound of claim 1 wherein X—Y—Z is 2-oxazolyl substituted with 1 to 2 groups independently selected from $C_1$–$C_4$alkyl, phenyl, benzyl, $CONR^cR^d$ and $CO_2R^b$.

5. A compound of claim 1 having the stereoconfiguration:

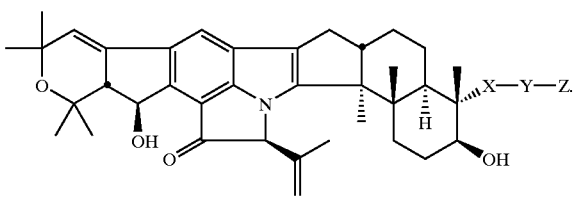

6. A compound of claim 1 wherein X—Y—Z is.

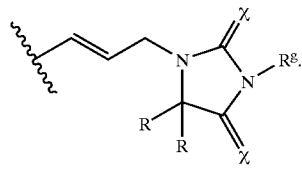

7. A compound of claim 1 having the formula:

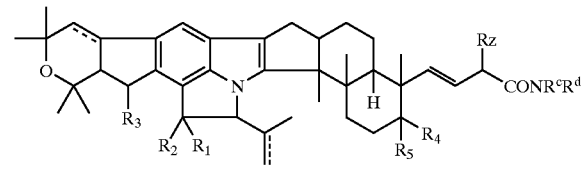

wherein $R^z$ is $OR^a$, $OC(O)R^a$, $OC(O)OR^b$, $OC(O)NR^cR^d$, $NR^cC(O)R^a$, $NR^cC(O)OR^a$, $NR^cC(O)NR^cR^d$, $NR^cSO_2R^a$.

8. A pharmaceutical composition comprising a compound of claim 1 and a pharmaceutically acceptable carrier.

9. A compound of claim 6 wherein x is O; and $R^g$ is selected from H, $C_1$–$C_{10}$alkyl optionally substituted with $CO_2R^i$; $C_3$–$C_7$cycloalkyl; naphthyl; phenyl optionally substituted with 1 or 2 groups independently selected from halogen and $C_1$–$C_3$perfluoroalkyl; and aryl $C_1$–$C_6$alkyl wherein aryl is phenyl, pyridyl or thienyl.

10. A compound of claim 7 wherein $R^z$ is $OR^a$, $OC(O)R^a$, $OC(O)OR^b$, and $OC(O)NR^cR^d$.

* * * * *